United States Patent
Mujica-Fernaud et al.

(10) Patent No.: US 10,497,877 B2
(45) Date of Patent: *Dec. 3, 2019

(54) COMPOUNDS AND ORGANIC ELECTRONIC DEVICES

(71) Applicant: Merck Patent GmbH, Darmstadt (DE)

(72) Inventors: Teresa Mujica-Fernaud, Darmstadt (DE); Elvira Montenegro, Weinheim (DE); Amir Hossain Parham, Frankfurt am Main (DE); Arne Buesing, Frankfurt am Main (DE); Frank Voges, Bad Duerkheim (DE)

(73) Assignee: Merck Patent GmbH (DE)

( * ) Notice: Subject to any disclaimer, the term of this patent is extended or adjusted under 35 U.S.C. 154(b) by 64 days.

This patent is subject to a terminal disclaimer.

(21) Appl. No.: 15/650,363

(22) Filed: Jul. 14, 2017

(65) Prior Publication Data

US 2017/0317285 A1 Nov. 2, 2017

Related U.S. Application Data

(63) Continuation of application No. 14/416,863, filed as application No. PCT/EP2013/001892 on Jun. 27, 2013.

(30) Foreign Application Priority Data

Jul. 23, 2012 (EP) ..................... 12005370

(51) Int. Cl.
| | |
|---|---|
| H01L 51/50 | (2006.01) |
| H01L 51/00 | (2006.01) |
| C09K 11/06 | (2006.01) |
| H05B 33/20 | (2006.01) |
| C07C 211/61 | (2006.01) |
| C07D 307/91 | (2006.01) |

(52) U.S. Cl.
CPC .......... *H01L 51/006* (2013.01); *C07C 211/61* (2013.01); *C07D 307/91* (2013.01); *C09K 11/06* (2013.01); *H01L 51/0039* (2013.01); *H01L 51/0052* (2013.01); *H01L 51/0059* (2013.01); *H01L 51/0061* (2013.01); *H05B 33/20* (2013.01); C07C 2603/18 (2017.05); C09K 2211/1011 (2013.01); C09K 2211/1014 (2013.01); C09K 2211/1029 (2013.01); C09K 2211/1088 (2013.01); C09K 2211/1433 (2013.01); C09K 2211/185 (2013.01); H01L 51/0058 (2013.01); H01L 51/0073 (2013.01); H01L 51/5012 (2013.01); H01L 51/5056 (2013.01); H01L 51/5088 (2013.01); H01L 51/5096 (2013.01); Y02E 10/549 (2013.01)

(58) Field of Classification Search
None
See application file for complete search history.

(56) References Cited

U.S. PATENT DOCUMENTS

| | | | |
|---|---|---|---|
| 8,691,398 B2 | 4/2014 | Yamada et al. | |
| 9,278,926 B2 | 3/2016 | Kato | |
| 2004/0042171 A1 | 3/2004 | Takamatsu et al. | |
| 2005/0221124 A1 | 10/2005 | Hwang | |
| 2006/0166034 A1 | 7/2006 | Saitoh et al. | |
| 2009/0066227 A1 | 3/2009 | Okinaka et al. | |
| 2009/0066235 A1 | 3/2009 | Yabunouchi et al. | |
| 2011/0198581 A1 | 8/2011 | Yabunouchi et al. | |
| 2012/0012832 A1 | 1/2012 | Yabunouchi et al. | |
| 2012/0161615 A1 | 6/2012 | Hong et al. | |
| 2013/0207046 A1 | 8/2013 | Pflumm et al. | |
| 2015/0287921 A1 | 10/2015 | Kato et al. | |

FOREIGN PATENT DOCUMENTS

| | | | |
|---|---|---|---|
| DE | 102010045405 A1 | 3/2012 | |
| EP | 2314565 A1 | 4/2011 | |
| EP | 2415752 A1 | 2/2012 | |
| JP | H05303221 A | 11/1993 | |
| JP | 10-95972 * | 4/1998 | ............ C09K 11/06 |
| JP | H1095972 | 4/1998 | |
| JP | H11219787 A | 8/1999 | |
| JP | 2001010996 A | 1/2001 | |
| JP | 2003324174 A | 11/2003 | |
| JP | 2004091350 A | 3/2004 | |
| JP | 03824385 B2 | 9/2006 | |
| JP | 04125076 B2 | 7/2008 | |
| JP | 04276398 B2 | 6/2009 | |
| JP | 2010222268 A | 10/2010 | |
| JP | 2013234169 A | 11/2013 | |
| KR | 20080080383 A | 9/2008 | |
| KR | 20110069077 A | 6/2011 | |
| KR | 101049328 B1 | 7/2011 | |

(Continued)

OTHER PUBLICATIONS

International Search Report for PCT/EP2013/001892 dated Nov. 28, 2013.

(Continued)

*Primary Examiner* — Gregory D Clark
(74) *Attorney, Agent, or Firm* — Drinker Biddle & Reath LLP

(57) ABSTRACT

The present invention relates to certain fluorenes, to the use of the compounds in an electronic device, and to an electronic device comprising at least one of these compounds. The present invention furthermore relates to a process for the preparation of the compounds and to a formulation and composition comprising one or more of the compounds.

22 Claims, No Drawings

(56) References Cited

FOREIGN PATENT DOCUMENTS

| KR | 20110117716 A | 10/2011 |
|---|---|---|
| KR | 20120066076 A | 6/2012 |
| WO | WO-2004020387 A1 | 3/2004 |
| WO | WO-2007/072838 A1 | 6/2007 |
| WO | WO-200786701 A1 | 8/2007 |
| WO | WO-2012091471 A2 | 7/2012 |

OTHER PUBLICATIONS

Buchwald (J. Am. Chem. Soc, 1994, 116, 7901-7902) and Hartwig (J. Am. Chem. Soc, 1994, 116, 5969-5970) [NPL one page citation only].

English Translation of Japanese Office Action for Japanese Application No. 2015-523437, dated Apr. 3, 2018.

English Translation of Japanese Office Action for Japanese Application No. 2015-523437, dated Jul. 4, 2017.

\* cited by examiner

COMPOUNDS AND ORGANIC ELECTRONIC DEVICES

CROSS-REFERENCE TO RELATED APPLICATIONS

This application is a continuation of U.S. application Ser. No. 14/416,863 which is incorporated by reference. U.S. application Ser. No. 14/416,863 is a national stage application (under 35 U.S.C. § 371) of PCT/EP2013/001892, filed Jun. 27, 2013, which claims benefit of European Application No. 12005370.7, filed Jul. 23, 2012, both of which are incorporated herein by reference in their entirety.

The present invention relates to novel organic compounds, to the use of the compounds in an electroluminescent device, and to an electroluminescent device comprising at least one of the compounds. The present invention furthermore relates to a process for the preparation of the compounds and to compositions and formulations comprising at least one of the compounds.

The development of functional compounds for use in electronic devices is currently the subject of intensive research. The aim here is, in particular, the development of compounds with which improved properties of electroluminescent devices in one or more relevant points can be achieved, such as, for example, power efficiency, lifetime or colour coordinates of the emitted light.

In accordance with the present invention, the term electroluminescent device is taken to mean, inter alia, organic light-emitting transistors (OLETs), organic field-quench devices (OFQDs), organic light-emitting electrochemical cells (OLECs, LECs or LEECs), organic laser diodes (O-lasers) and organic light-emitting diodes (OLEDs).

Of particular interest is the provision of compounds for use in the last-mentioned electronic devices called OLEDs. The general structure and the functional principle of OLEDs are known to the person skilled in the art and are disclosed, inter alia, in U.S. Pat. Nos. 4,539,507, 5,151,629, EP 0676461 and WO 1998/27136.

Further improvements are still necessary with respect to the performance data of OLEDs, in particular with a view to broad commercial use, for example in display devices or as light sources. Of particular importance in this connection are the lifetime, the efficiency and the operating voltage of the OLEDs and the colour values achieved. In addition, it is desirable, for use as functional materials in electronic devices, for the compounds to have high thermal stability and a high glass-transition temperature and to be sublimable without decomposition.

In this connection, there is, in particular, a need for alternative hole-transport materials. In hole-transport materials in accordance with the prior art, the voltage generally increases with the layer thickness of the hole-transport layer. In practice, a greater layer thickness of the hole-transport layer would frequently be desirable, but this often has the consequence of a higher operating voltage and worse performance data. In this connection, there is a need for novel hole-transport materials which have high charge-carrier mobility, enabling thicker hole-transport layers to be achieved with an only slight increase in the operating voltage.

The prior art describes the use of various fluorenes as charge-transport material in electronic and electroluminescent devices.

JP 3824385 B2 discloses 2- and 7-substituted fluorenes which are substituted by dibenzofurans or carbazoles.

US 2012/20012832 discloses fluorenes which are substituted by condensed aromatic groups.

WO 2004/020387 discloses fluorenes which are substituted in position 2 by an amino group, where the amino group is itself disubstituted by in each case one phenyl group.

JP 05-303221 discloses the use of 2- and 4-substituted fluorenes as photo-sensitive compound. The use in electroluminescent devices, such as OLEDs or OLECs, is not described herein.

In spite of the compounds already known, there continues to be a need for novel hole-transport and hole-injection materials for use in OLEDs. In particular, there is a need for materials with which the above-mentioned, highly desired improvements in the performance data and properties of OLEDs can be achieved.

There is likewise a need for novel matrix materials for use in OLEDs and in other electronic devices. In particular, there is a need for matrix materials for phosphorescent dopants and for matrix materials for mixed-matrix systems, which preferably result in good efficiency, a long lifetime and a low operating voltage of the electronic devices.

The present invention is thus based on the object of providing electroluminescent devices and compounds which are suitable for use in electroluminescent devices, such as, for example, OLEDs, and which can be employed, in particular, as hole-transport materials and/or as hole-injection materials and/or as matrix materials.

As part of the present invention, it has been found, surprisingly, that compounds of the formula (1) indicated below are highly suitable for the above-mentioned uses in electroluminescent devices.

The invention thus relates to an electroluminescent device comprising at least one compound of the formula (1)

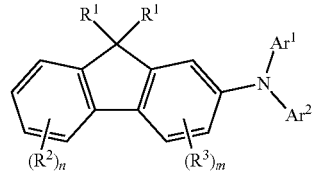

formula (1)

where the following applies to the symbols and indices used:

$Ar^1$, $Ar^2$
are on each occurrence, identically or differently, an aromatic or heteroaromatic group having 10 to 60 aromatic ring atoms, which may be substituted by one or more radicals $R^4$, which are identical to or different from one another, where the two groups $Ar^1$ and $Ar^2$ each contain at least two or more aromatic or heteroaromatic rings;

$R^1$
is on each occurrence, identically or differently, H, D, F, Cl, Br, I, C(=O)$R^5$, CN, Si($R^5$)$_3$, NO$_2$, P(=O)($R^5$)$_2$, S(=O)$R^5$, S(=O)$_2R^5$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^5$ and where one or more CH$_2$ groups in the above-mentioned groups may be replaced by —$R^5$C=C$R^5$—, Si($R^5$)$_2$, C=O, C=S, C=N$R^5$, —C(=O)O—, —C(=O)N$R^5$—, P(=O)($R^5$), —O—, —S—, SO or SO$_2$ and where one or more H atoms in the above-mentioned groups may be replaced by D, F, Cl, Br, I, CN or NO$_2$, or an aromatic or heteroaromatic ring system having 6 to 30 ring atoms, which may in each case be substituted by one or more radicals R$^5$, or a condensed ring system having 9 to 30 ring atoms, which may in each case be substituted by one or more radicals R$^5$, where, in the case of aromatic or heteroaromatic condensed rings, not more than 10 ring atoms may be present; the two radicals R$^1$ may also form a ring closure with one another, so that a Spiro compound forms, where no aromatic or heteroaromatic rings are condensed onto the ring formed by the two radicals R$^1$;

R$^2$, R$^3$ and R$^4$ are on each occurrence, identically or differently, H, D, F, Cl, Br, I, C(=O)R$^5$, CN, Si(R$^5$)$_3$, NO$_2$, P(=O)(R$^5$)$_2$, S(=O)R$^5$, S(=O)$_2$R$^5$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals R$^5$ and where one or more CH$_2$ groups in the above-mentioned groups may be replaced by —R$^5$C=CR$^5$—, —C≡C—, Si(R$^5$)$_2$, C=O, C=S, C=NR$^5$, —C(=O)O—, —C(=O)NR$^5$—, P(=O)(R$^5$), —O—, —S—, SO or SO$_2$ and where one or more H atoms in the above-mentioned groups may be replaced by D, F, Cl, Br, I, CN or NO$_2$, or an aromatic or heteroaromatic ring system having 6 to 30 ring atoms, which may in each case be substituted by one or more radicals R$^5$;

R$^5$ is on each occurrence, identically or differently, H, D, F, Cl, Br, I, C(=O)R$^6$, CN, Si(R$^6$)$_3$, NO$_2$, P(=O)(R$^6$)$_2$, S(=O)R$^6$, S(=O)$_2$R$^6$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals R$^6$ and where one or more CH$_2$ groups in the above-mentioned groups may be replaced by —R$^6$C=CR$^6$—, —C≡C—, Si(R$^6$)$_2$, C=O, C=S, C=NR$^6$, —C(=O)O—, —C(=O)NR$^6$—, P(=O)(R$^6$), —O—, —S—, SO or SO$_2$ and where one or more H atoms in the above-mentioned groups may be replaced by D, F, Cl, Br, I, CN or NO$_2$, or an aromatic or heteroaromatic ring system having 5 to 30 aromatic ring atoms, which may in each case be substituted by one or more radicals R$^6$, or an aryloxy or heteroaryloxy group having 5 to 30 aromatic ring atoms, which may be substituted by one or more radicals R$^6$;

R$^6$ is on each occurrence, identically or differently, H, D, F or an aliphatic, aromatic or heteroaromatic organic radical having 1 to 20 C atoms, in which, in addition, one or more H atoms may be replaced by D or F;

n is 0, 1, 2, 3 or 4;

m is 0, 1, 2 or 3;

with the proviso that the compound of the formula (1), besides the one fluorene group and besides the possible condensed or polycyclic groups in position 9 of the fluorene, contains no further polycyclic or condensed groups.

The numbering on the fluorene is defined as follows.

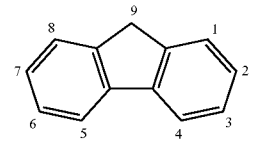

Preference is given to an electroluminescent device which comprises at least one compound of the formula (1) in which the two radicals R$^1$ are identical.

It is preferred for the electroluminescent device to comprise at least one compound of the formula (1) which is characterised in that m is equal to 1 or 0, very preferably m is equal to 0.

It is furthermore preferred for the electroluminescent device to comprise at least one compound of the formula (1) which is characterised in that n is equal to 2, 1 or 0, very preferably n is equal to 0 or 1.

The compound of the formula (1) is preferably selected from a compound of the formula (2),

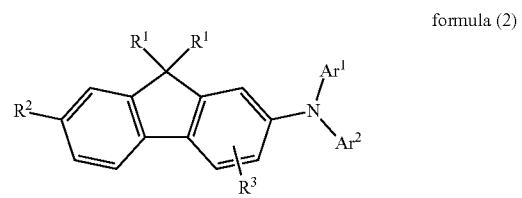

formula (2)

where the symbols are defined as indicated above.

Most preference is given to a compound of the formula (2) in which the two radicals R$^1$ are identical.

In a furthermore preferred embodiment of the present invention, the electroluminescent device comprises at least one compound of the formula (3), where preference is furthermore given to a compound of the formula (3) in which the radicals R$^1$ are identical.

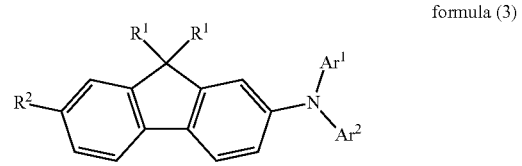

formula (3)

In a very preferred embodiment of the present invention, R$^2$ is equal to H or a straight-chain alkyl group having 1 to 20 C atoms or a branched or cyclic alkyl group having 3 to 20 C atoms, where the above-mentioned groups may each be substituted by one or more radicals R$^5$ and where one or more H atoms in the above-mentioned groups may be replaced by D, F, Cl, Br, I, CN or NO$_2$, or an aromatic ring system having 6 to 30 aromatic ring atoms, which may in each case be substituted by one or more radicals R$^5$.

R$^2$ is particularly preferably equal to H or an aromatic ring system having 6 to 30 aromatic ring atoms, which may in each case be substituted by one or more radicals R$^5$.

In a very particularly preferred embodiment, the electroluminescent device comprises at least one compound of the formula (3) in which R$^2$ is equal to H and the two R$^1$ are, identically to or differently from one another, preferably identically, an aromatic or heteroaromatic ring system having 6 to 30 aromatic ring atoms, which may in each case be substituted by one or more radicals $R^5$.

$R^2$ in the formulae (1) to (3) is especially preferably equal to phenyl, biphenyl, terphenyl or quaterphenyl, each of which may be substituted by one or more radicals $R^5$, where it is furthermore preferred for these to be unsubstituted, or H.

In a further very particularly preferred embodiment, the electroluminescent device comprises at least one compound of the formula (3) in which $R^2$ is an aromatic ring system having 6 to 30 aromatic ring atoms, which may in each case be substituted by one or more radicals $R^5$, and $R^1$ is, identically to or differently from one another, preferably identically, a straight-chain alkyl group having 1 to 20 C atoms or a branched or cyclic alkyl group having 3 to 20 C atoms, where the above-mentioned groups may each be substituted by one or more radicals $R^5$ and where one or more H atoms in the above-mentioned groups may be replaced by D, F, Cl, Br, I, CN or $NO_2$.

It is furthermore preferred for the electroluminescent device to comprise at least one compound of the formula (4),

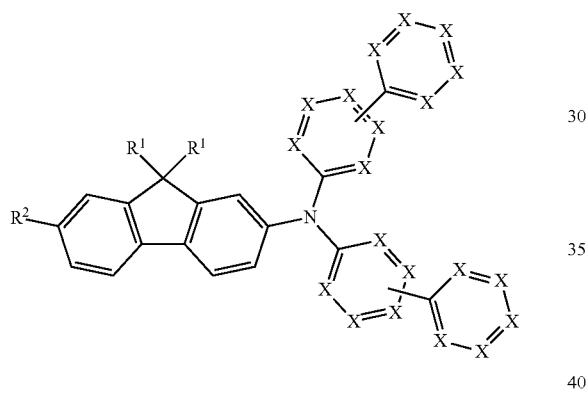

formula (4)

in which X is, identically or differently on each occurrence, N or $CR^4$, where only 3 of the groups X per ring may be N. It is very preferred for X in formula (4) to be equal to $CR^4$, where the above definitions apply to the radicals $R^1$, $R^2$ and $R^4$.

Preferred radicals $Ar^1$ and $Ar^2$ are selected from the radicals having the formulae (5) to (60) shown in the following table, where the radicals may be substituted, as already indicated above, by one or more radicals $R^4$, which are identical to or different from one another;

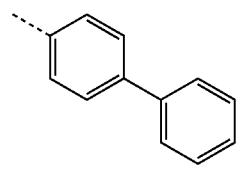

formula (5)

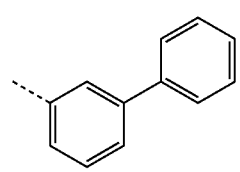

formula (6)

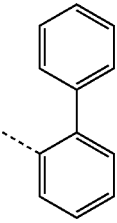

formula (7)

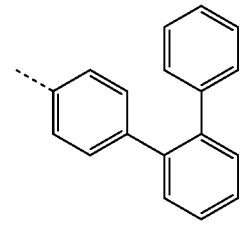

formula (8)

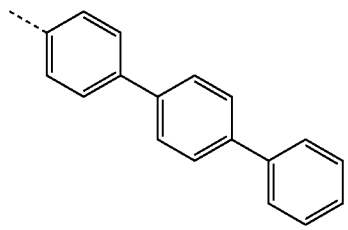

formula (9)

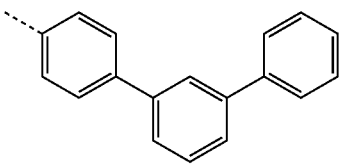

formula (10)

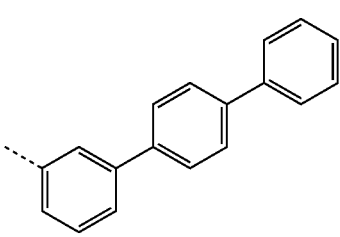

formula (11)

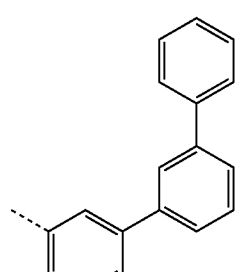

formula (12)

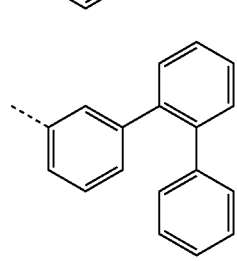

formula (13)

formula (14)
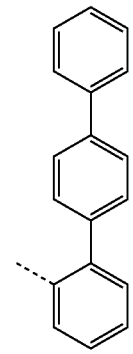
formula (15)
formula (16)
formula (17)
formula (18)
formula (19)
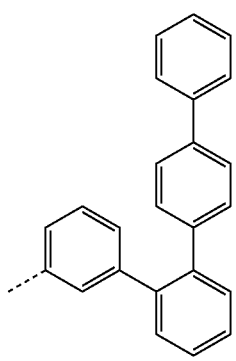
formula (20)
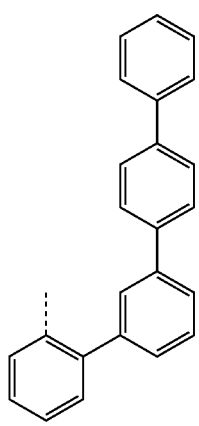
formula (21)
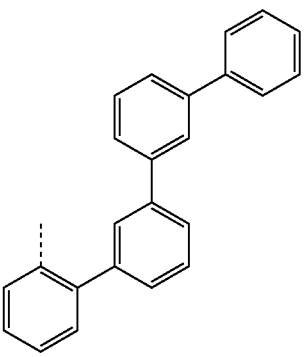
formula (22)
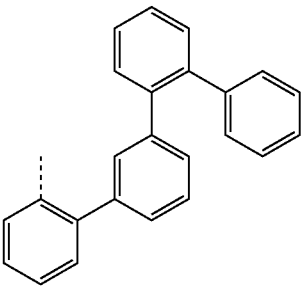

formula (23)
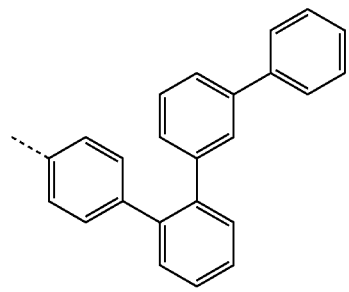
formula (24)
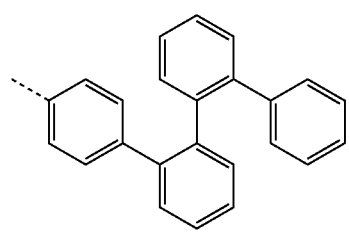
formula (25)
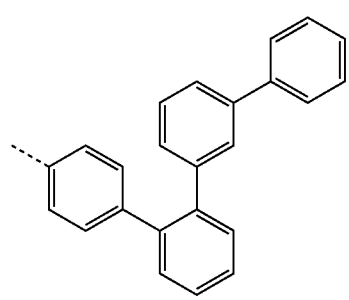
formula (26)
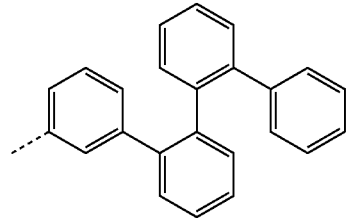
formula (27)
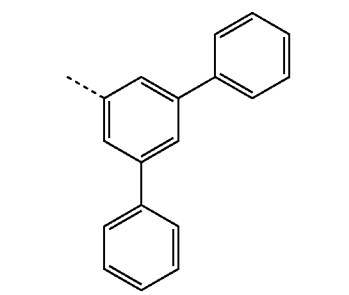
formula (29)
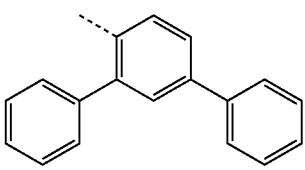
formula (30)
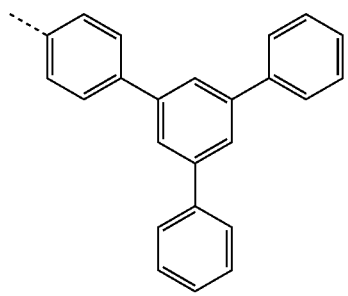
formula (31)
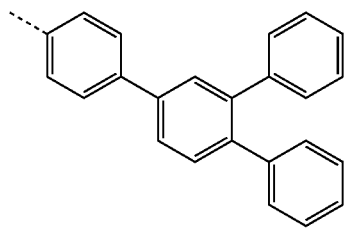
formula (32)
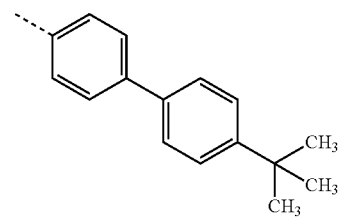
formula (33)
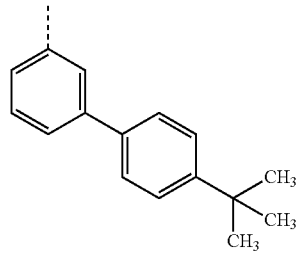
formula (34)
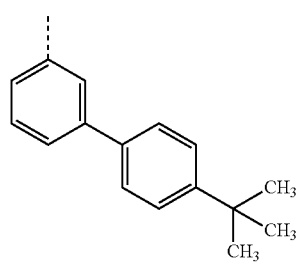

formula (35)
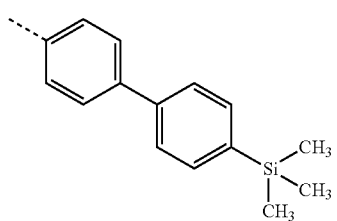
formula (36)
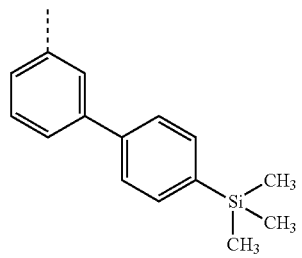
formula (37)
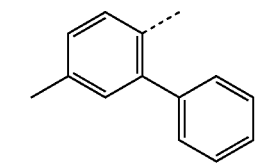
formula (38)
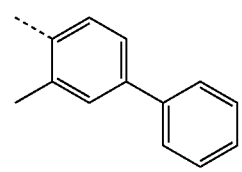
formula (39)
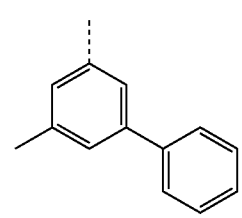
formula (40)
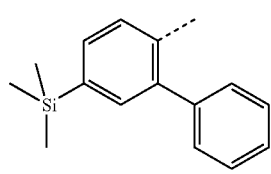
formula (41)
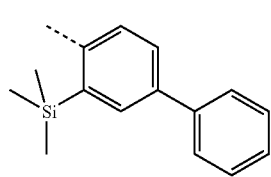
formula (42)
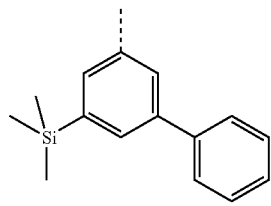
formula (43)
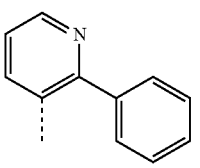
formula (44)
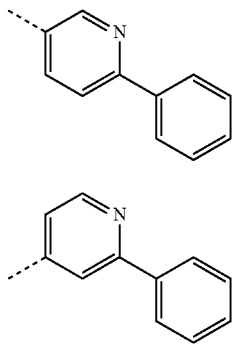
formula (45)
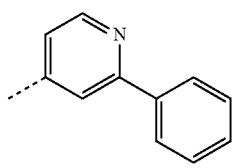
formula (46)
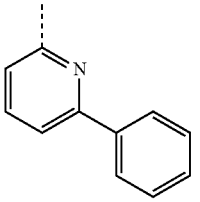
formula (47)
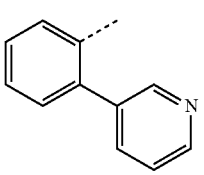
formula (48)
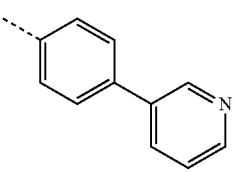
formula (49)
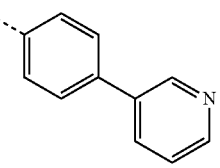
formula (50)
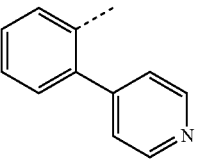
formula (51)
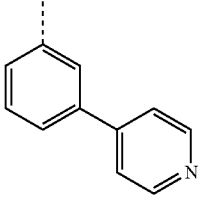

formula (52)

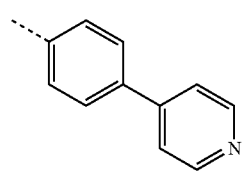

formula (53)

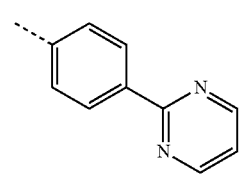

formula (54)

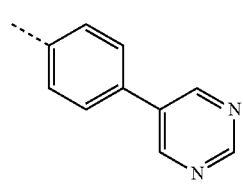

formula (55)

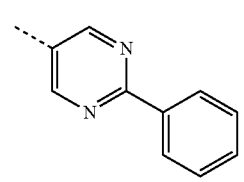

formula (56)

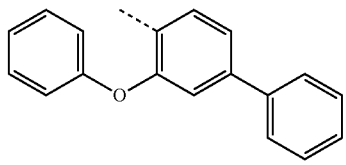

formula (57)

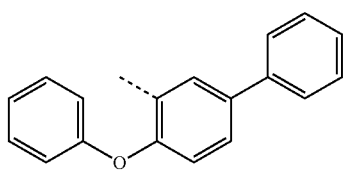

formula (58)

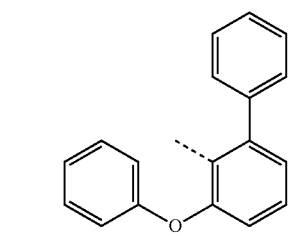

formula (59)

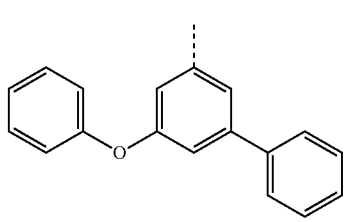

formula (60)

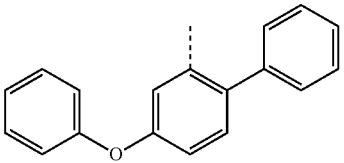

Preference is given in the sense of the present invention to an electroluminescent device which comprises at least one compound of the formula (1) in which $Ar^1$ and $Ar^2$ contain only aromatic rings, but not heteroaromatic rings.

$Ar^1$ and $Ar^2$ are especially preferably, identically or differently, biphenyl, terphenyl or quaterphenyl, each of which may be substituted by one or more radicals $R^4$, where it is furthermore preferred for these to be unsubstituted.

In a furthermore very preferred embodiment of the present invention, in the compound of the formula (1), the two radicals $R^1$
are identical and are selected from a straight-chain alkyl, alkoxy or thioalkyl group having 1 to 20 C atoms or a branched or cyclic alkyl, alkoxy or thioalkyl group having 3 to 20 C atoms, where the above-mentioned groups may each be substituted by one or more radicals $R^5$ and where one or more H atoms in the above-mentioned groups may be replaced by D, F, Cl, Br, I, CN or $NO_2$, or an aromatic or heteroaromatic ring system having 6 to 30 ring atoms, which may in each case be substituted by one or more radicals $R^5$, or a condensed ring system having 9 to 30 ring atoms, which may in each case be substituted by one or more radicals $R^5$, where, in the case of aromatic or heteroaromatic condensed rings, not more than 10 ring atoms may be present; the two radicals $R^1$ may also form a ring closure with one another, so that a Spiro compound forms, where no aromatic or heteroaromatic rings are condensed onto the ring formed by the two radicals $R^1$;
is equal to 1 and the radical $R^2$ is in position 7 of the fluorene;
m is equal to 0;
$R^2$ is equal to an alkyl group having 1 to 20 C atoms or a branched or cyclic alkyl group having 3 to 20 C atoms, a pyridyl, phenyl, biphenyl, terphenyl or quaterphenyl group, where the groups may be substituted by one or more radicals $R^5$, where it is furthermore preferred for the aromatic or heteroaromatic group to be unsubstituted, or is equal to H;
$Ar^1$ and $Ar^2$
are identical or different and are selected from biphenyl, terphenyl and quaterphenyl, each of which may be substituted by one or more radicals $R^4$, where it is furthermore preferred for these to be unsubstituted.

In a furthermore very preferred embodiment of the present invention, in the compound of the formula (1), the two radicals $R^1$
are identical and are selected from a straight-chain alkyl group having 1 to 20 C atoms or a branched or cyclic alkyl group having 3 to 20 C atoms, where the groups may each be substituted by one or more radicals $R^5$ and where one or more H atoms in the above-mentioned groups may be replaced by D, F, Cl, Br, I, CN or $NO_2$;
n is equal to 1 and the radical $R^2$ is in position 7 of the fluorene;
m is equal to 0;

$R^2$ is equal to H or an alkyl group having 1 to 20 C atoms or a branched or cyclic alkyl group having 3 to 20 C atoms, where the groups may be substituted by one or more radicals $R^5$, where $R^2$ is preferably equal to H;

$Ar^1$ and $Ar^2$
are identical or different and are selected from biphenyl, terphenyl and quaterphenyl, each of which may be substituted by one or more radicals $R^4$, where it is furthermore preferred for these to be unsubstituted.

In a furthermore very preferred embodiment of the present invention, in the compound of the formula (1),
the two radicals $R^1$
are identical and are selected from a straight-chain alkyl group having 1 to 20 C atoms or a branched or cyclic alkyl group having 3 to 20 C atoms, where the groups may each be substituted by one or more radicals $R^5$ and where one or more H atoms in the above-mentioned groups may be replaced by D, F, Cl, Br, I, CN or $NO_2$;

n is equal to 1 and the radical $R^2$ is in position 7 of the fluorene;

is equal to 0;

$R^2$ is equal to a pyridyl, phenyl, biphenyl, terphenyl or quaterphenyl group, where the groups may be substituted by one or more radicals $R^5$, where it is furthermore preferred for the aromatic or hetero-aromatic group to be unsubstituted;

$Ar^1$ and $Ar^2$
are identical or different and are selected from biphenyl, terphenyl and quaterphenyl, each of which may be substituted by one or more radicals $R^4$, where it is furthermore preferred for these to be unsubstituted.

In a furthermore very preferred embodiment of the present invention, in the compound of the formula (1),
the two radicals $R^1$
are identical and are selected from an aromatic or heteroaromatic ring system having 6 to 30 ring atoms, which may in each case be substituted by one or more radicals $R^5$, or a condensed ring system having 9 to 30 ring atoms, which may in each case be substituted by one or more radicals $R^5$, where, in the case of aromatic or heteroaromatic condensed rings, not more than 10 ring atoms may be present;

n is equal to 1 and the radical $R^2$ is in position 7 of the fluorene;

is equal to 0;

$R^2$ is equal to an alkyl group having 1 to 20 C atoms or a branched or cyclic alkyl group having 3 to 20 C atoms, a pyridyl, phenyl, biphenyl, terphenyl or quaterphenyl group, where the groups may be substituted by one or more radicals $R^5$, where it is furthermore preferred for the aromatic or heteroaromatic group to be unsubstituted, or is equal to H, where $R^2$ is preferably equal to H;

$Ar^1$ and $Ar^2$
are identical or different and are selected from biphenyl, terphenyl and quaterphenyl, each of which may be substituted by one or more radicals $R^4$, where it is furthermore preferred for these to be unsubstituted.

Preference is furthermore given in the sense of the present invention to an electroluminescent device which comprises at least one compound of the formula (1) which, besides the one fluorene group, contains no further polycyclic or condensed groups.

The compounds according to the invention can be synthesised by processes which are known to the person skilled in the art from the prior art. The preparation can be carried out, for example, by means of halogenation, Buchwald coupling and Suzuki coupling.

The following scheme shows a preferred synthetic route for the preparation of the compounds of the formula (1) according to the invention. For the synthesis of the compounds according to the invention, the fluorene compound A is reacted with an amine B of the formula $Ar^1$—NH—$Ar^2$ in a Buchwald coupling

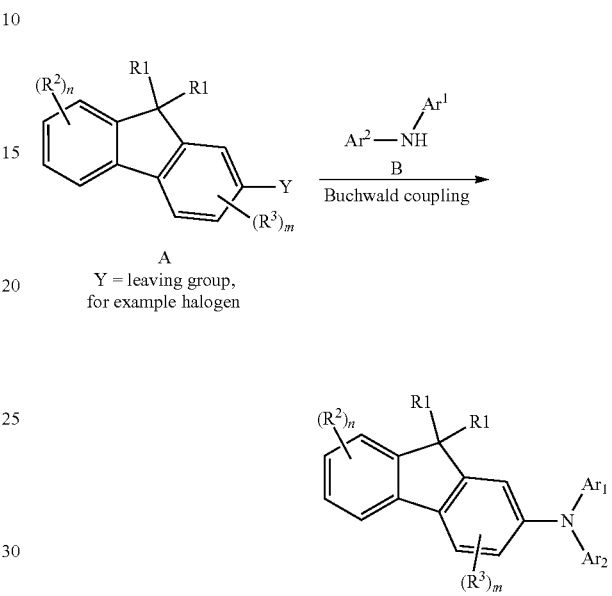

Y = leaving group, for example halogen

Another preferred synthetic route for the preparation of the compounds according to the invention is depicted in the following scheme. The carboxylate groups in compound C are converted into the corresponding alcohol D by the addition reaction of an alkyl- or aryl-metal compound, for example an alkyl- or aryllithium compound or an alkyl- or aryl-Grignard compound. This alcohol can be cyclised under acidic conditions to give compound E. Finally, a Buchwald coupling to an amine B of the formula $Ar^1$—NH—$Ar^2$ is carried out

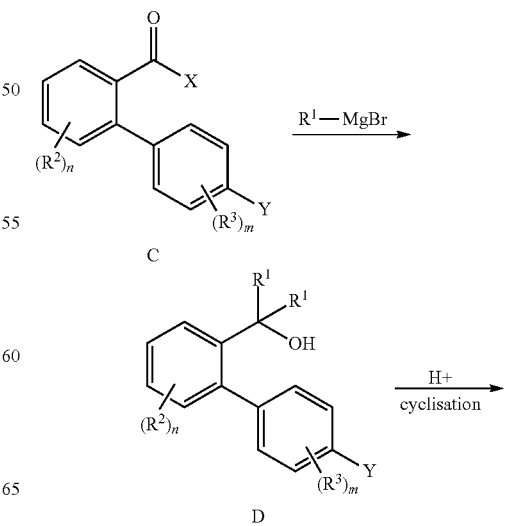

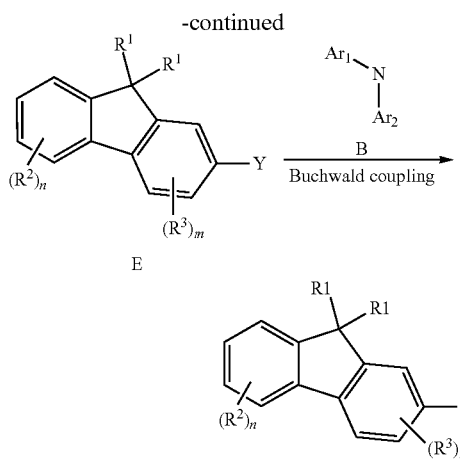

Y = leaving group, for example halogen
X = Cl, OR

The following scheme shows a further preferred synthetic route for the preparation of compounds according to the invention. For this purpose, the fluorene A is reacted with a boronic acid F of the formula $Ar^3$—$B(OH)_2$ in a Suzuki coupling. Bromination of the resultant compounds using, for example, bromine followed by a Buchwald coupling to an amine of the formula $Ar^1$—NH—$Ar^2$ gives the corresponding compounds according to the invention.

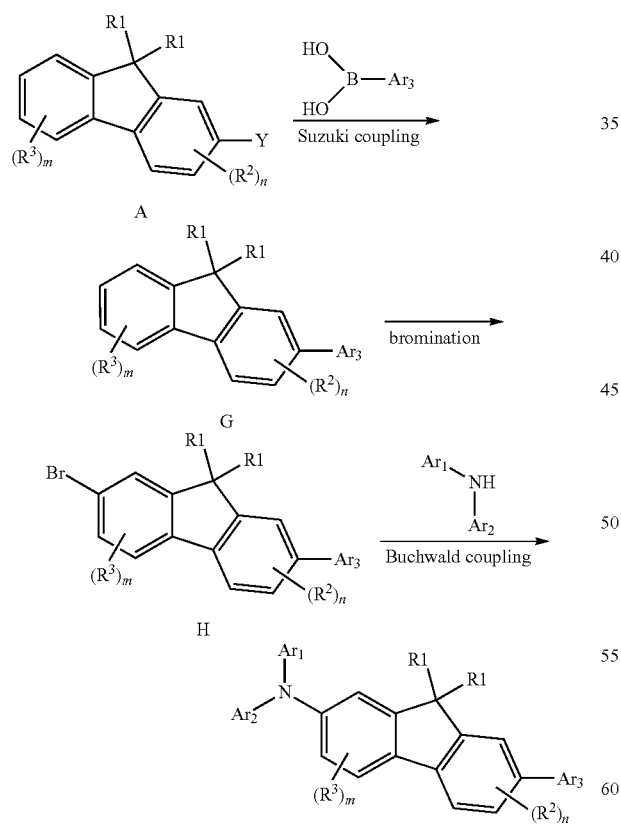

Y = leaving group, for example halogen

Synthetic routes for the starting compounds A, B and C which are employed in the synthesis of the compounds according to the invention are known to the person skilled in the art. Furthermore, some explicit synthetic processes are described in detail in the working examples.

Preferred coupling reactions here are Buchwald couplings.

The compounds described above, in particular compounds which are substituted by reactive leaving groups, such as bromine, iodine, chlorine, boronic acid or boronic acid ester, can be used as monomers for the production of corresponding oligomers, dendrimers or polymers. The oligomerisation or polymerisation here preferably takes place via the halogen functionality or the boronic acid functionality.

Preferred compounds which are used in the electroluminescent devices according to the invention are shown by way of example in the following table, formula (61)

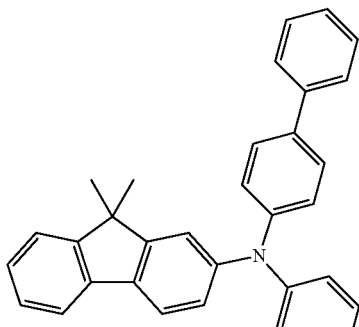

formula (62)

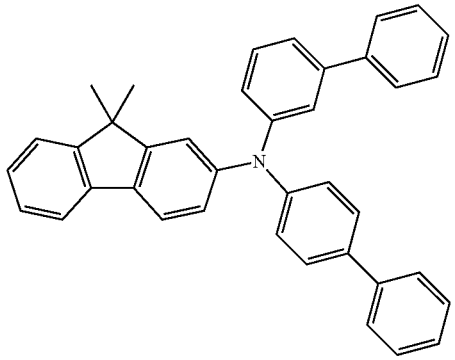

formula (63)

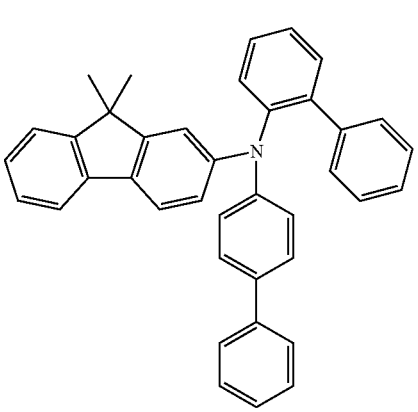

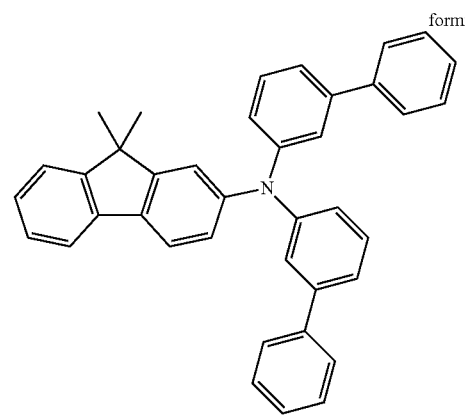
formula (64)
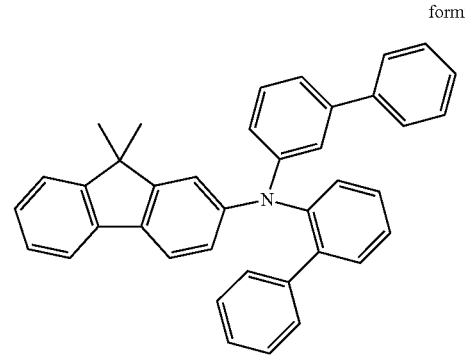
formula (65)
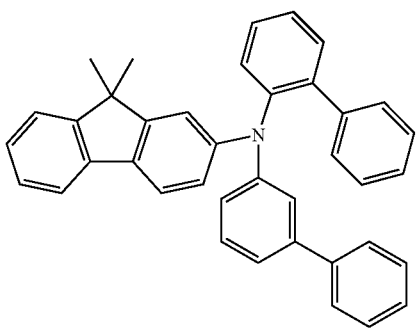
formula (66)
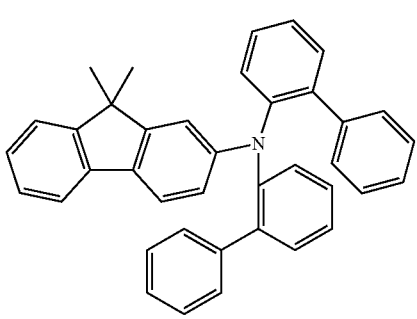
formula (67)
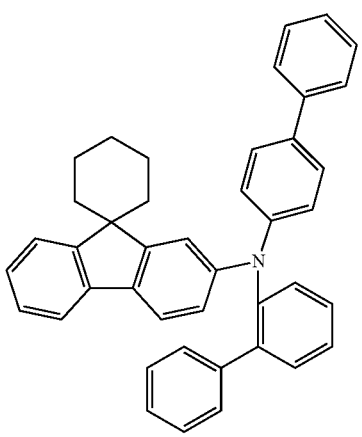
formula (68)
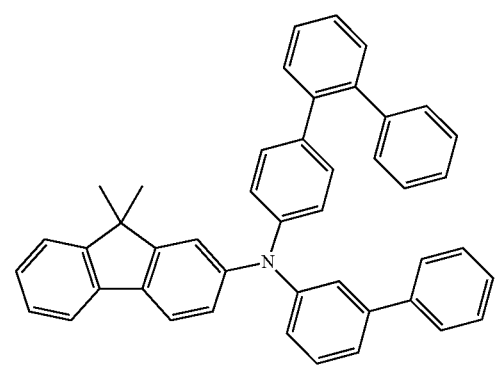
formula (69)
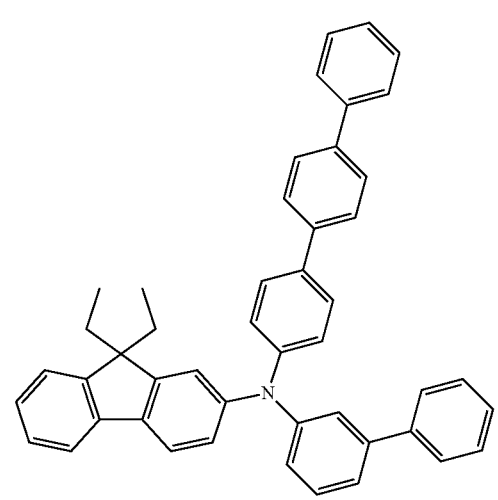
formula (70)

formula (71)
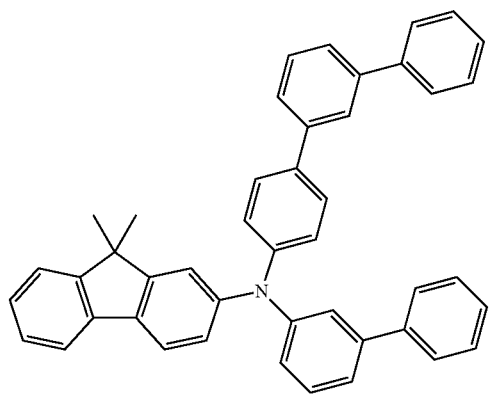
formula (72)
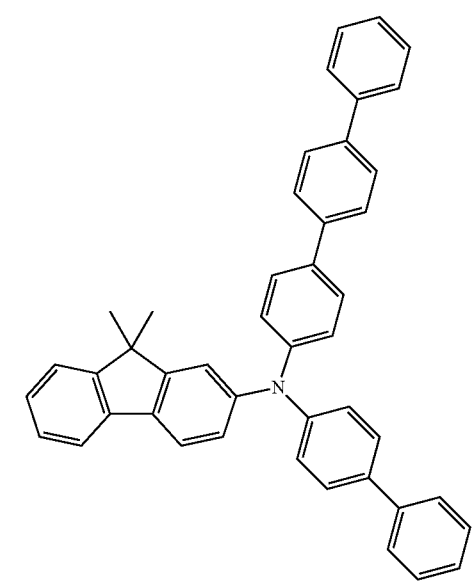
formula (73)
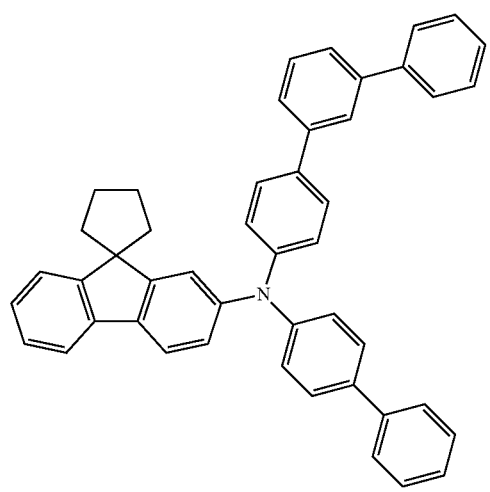
formula (74)
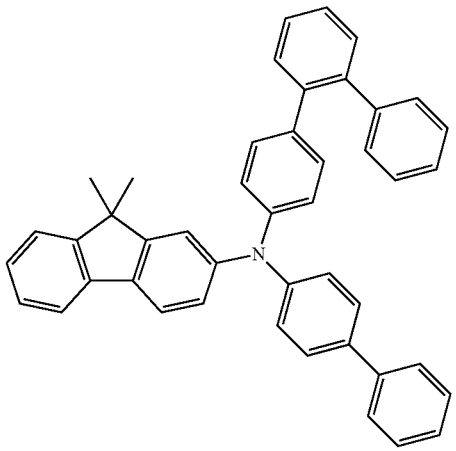
formula (75)
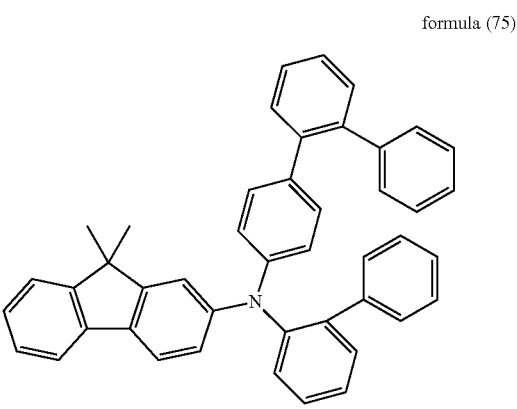
formula (76)
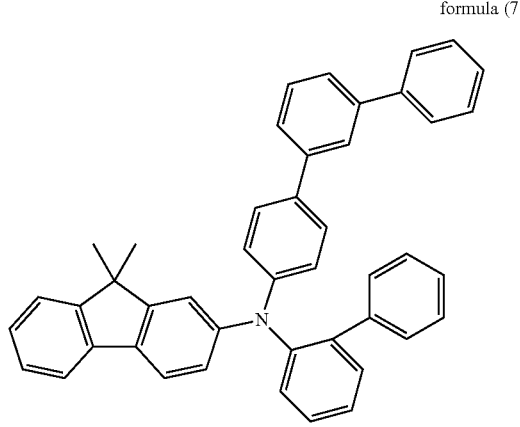

formula (77)
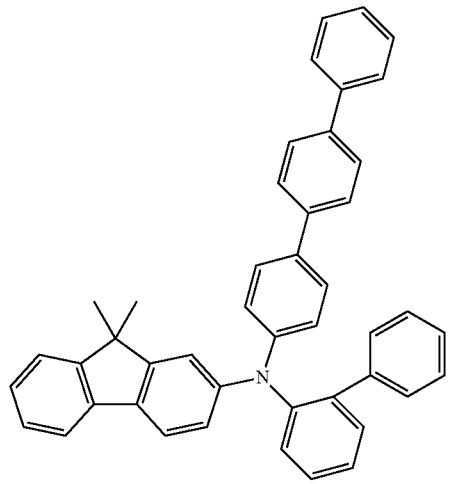
formula (78)
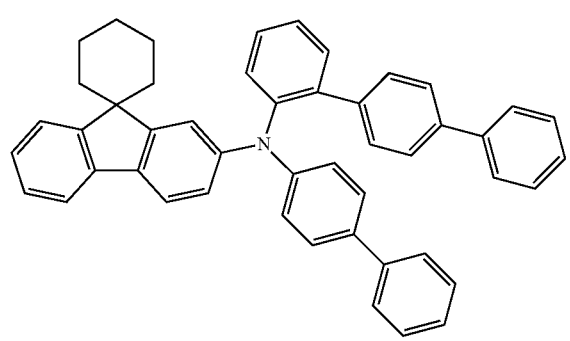
formula (79)
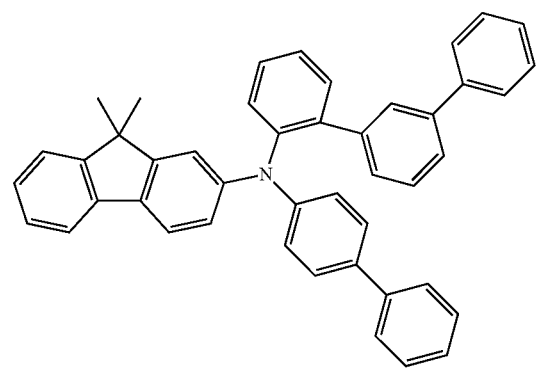
formula (80)
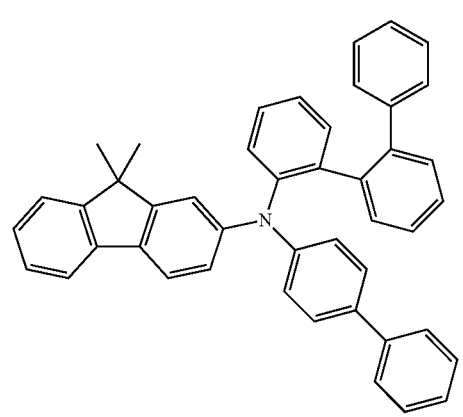
formula (81)
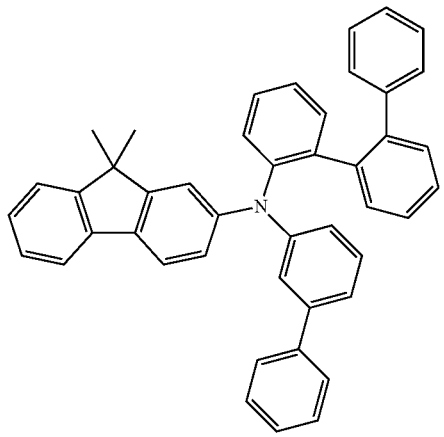
formula (82)
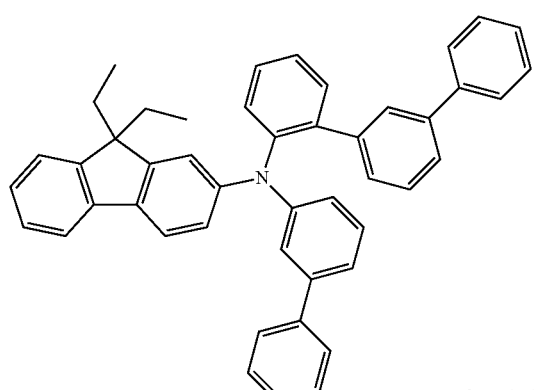
formula (83)
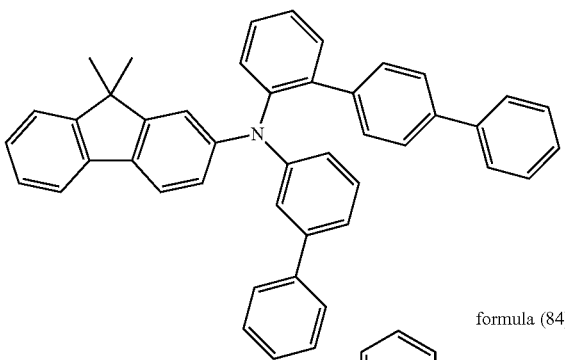
formula (84)
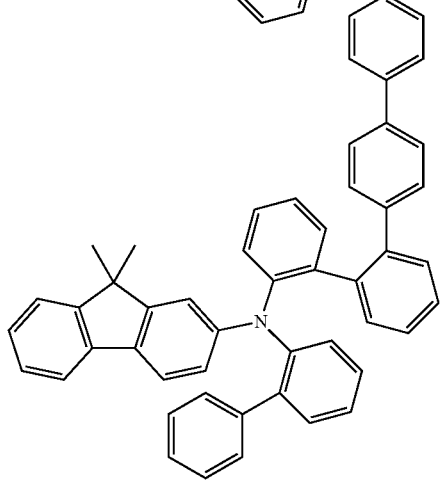

formula (85)
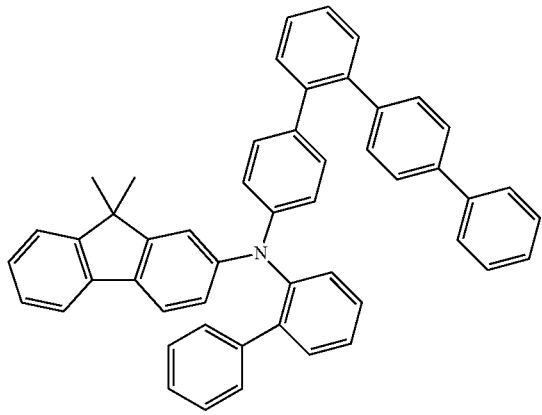
formula (86)
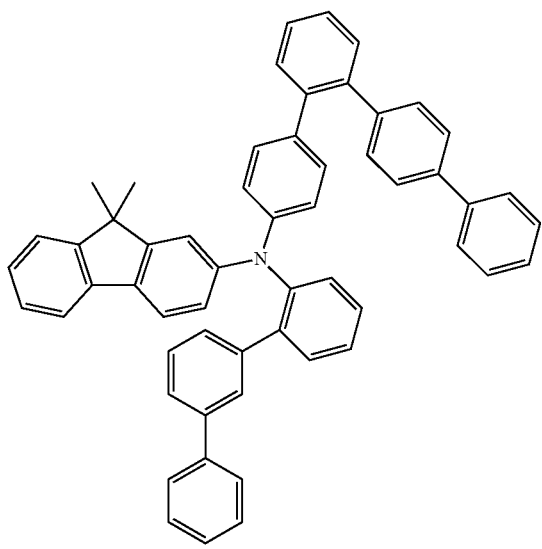
formula (87)
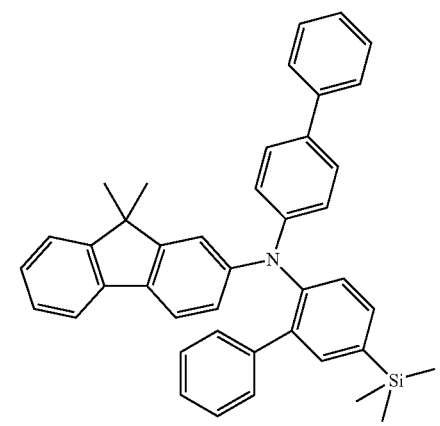
formula (88)
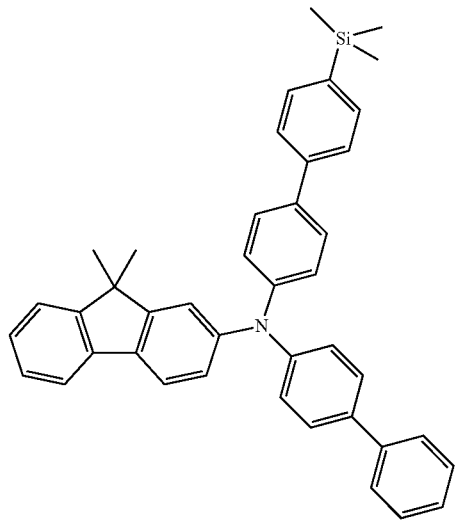
formula (89)
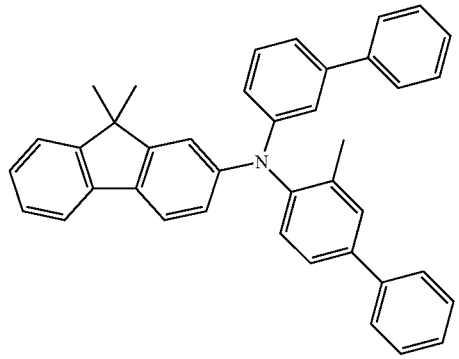
formula (90)
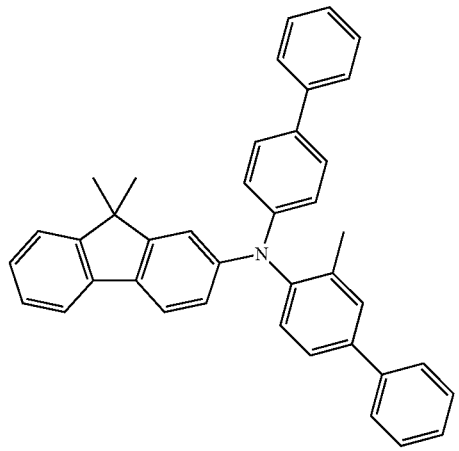

formula (91)
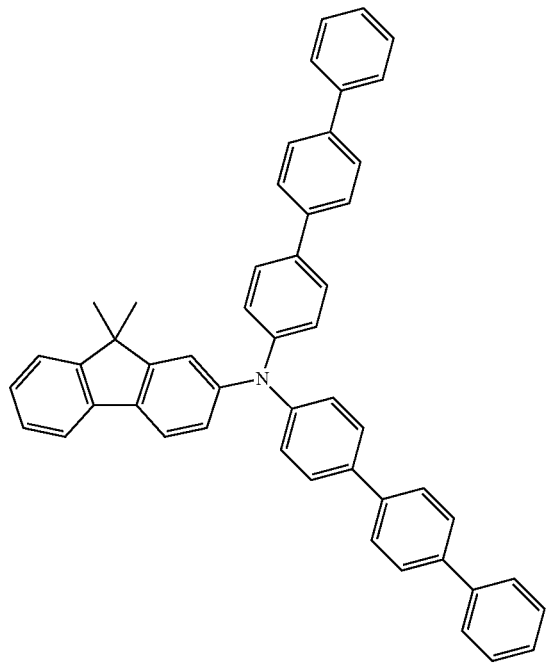
formula (92)
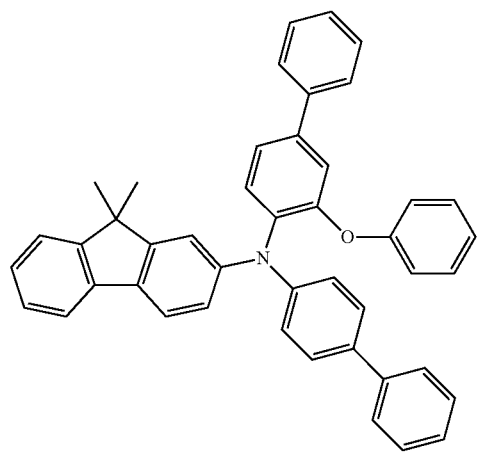
formula (93)
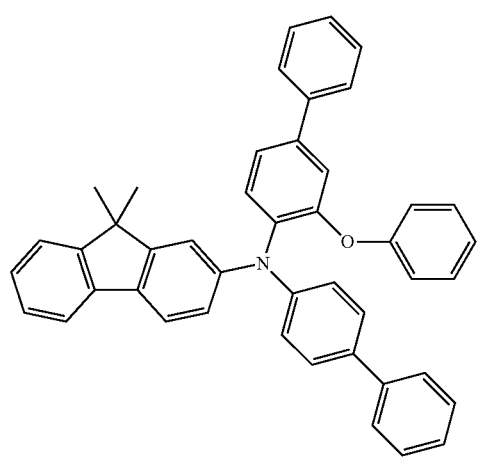
formula (94)
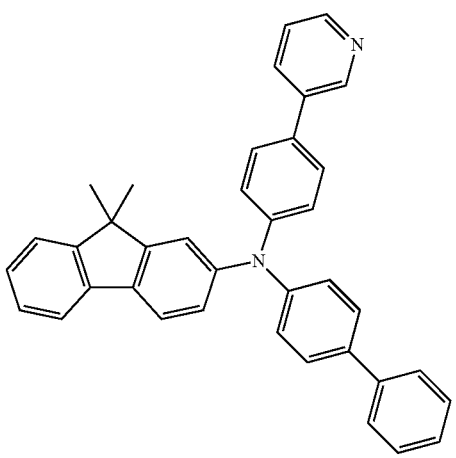
formula (95)
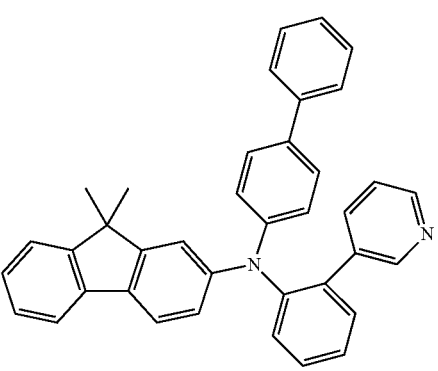
formula (96)
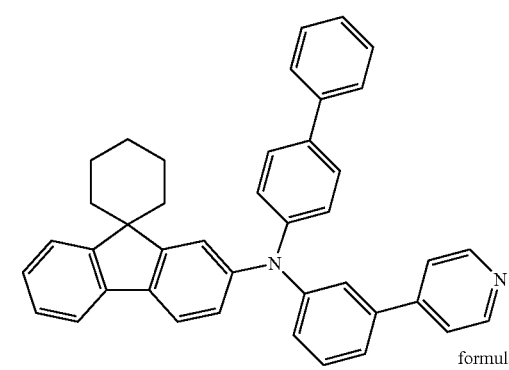
formula (97)
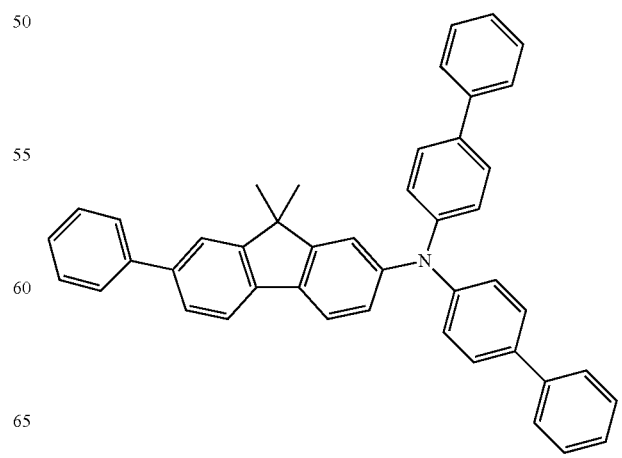

formula (98)
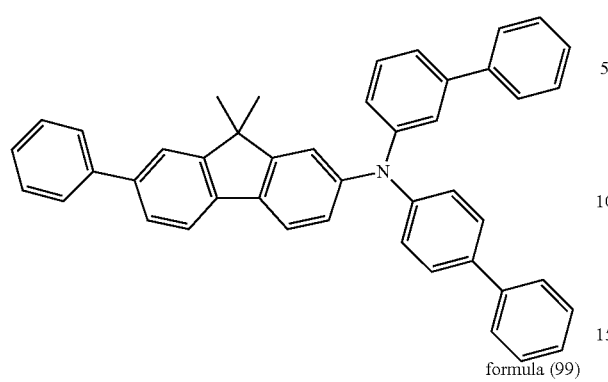
formula (99)
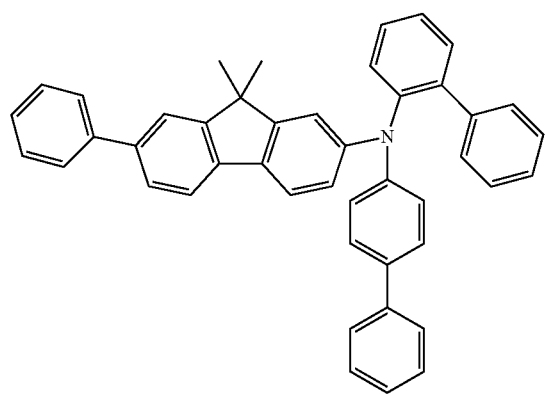
formula (100)
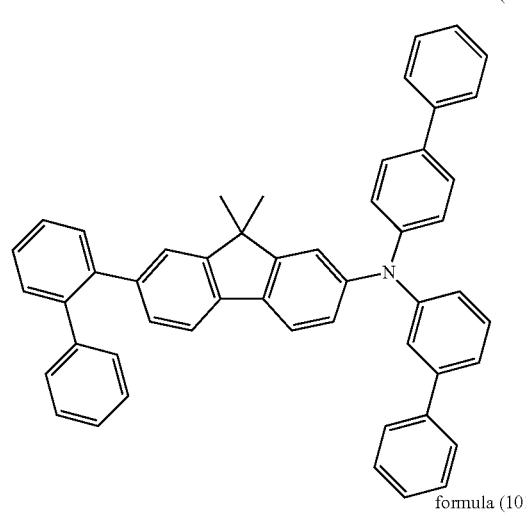
formula (101)
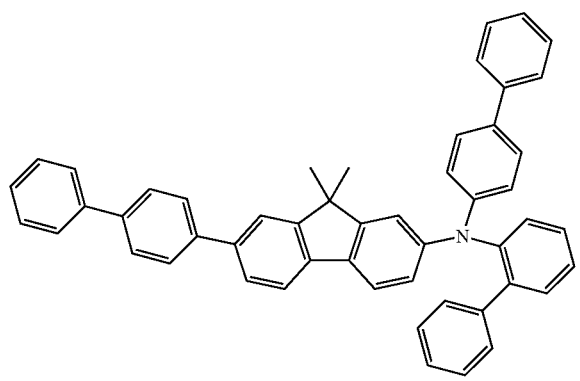
formula (102)
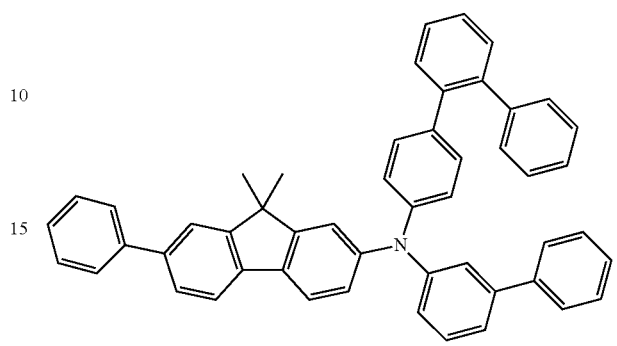
formula (103)
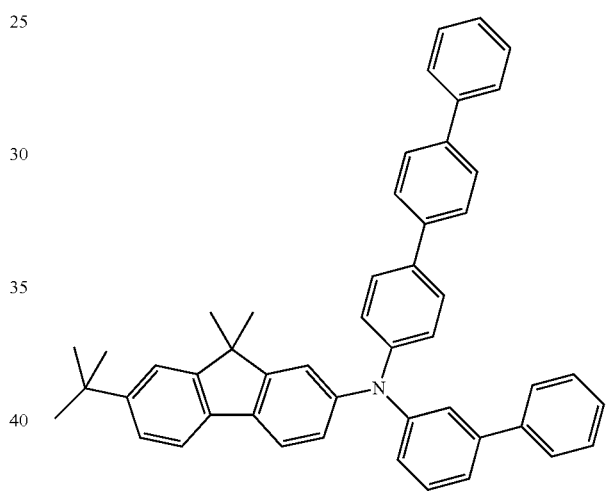
formula (104)
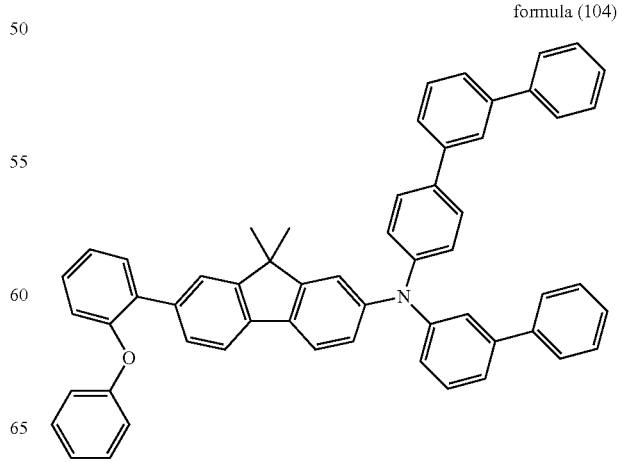

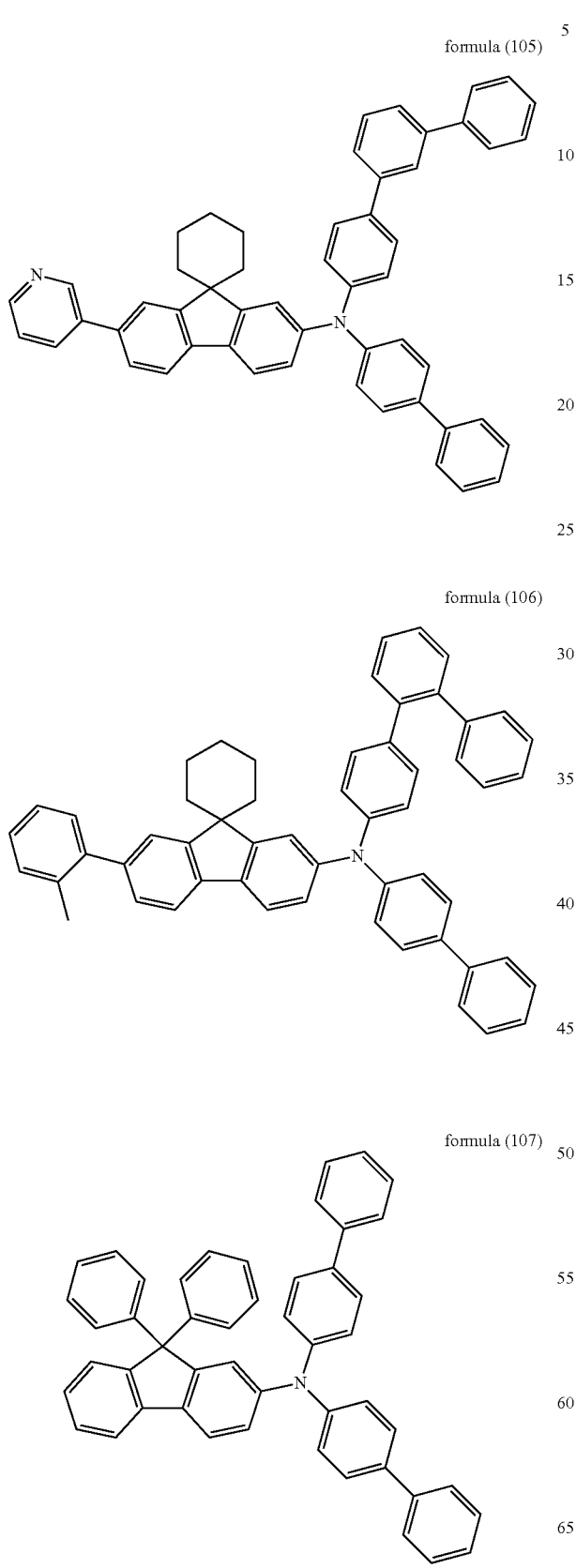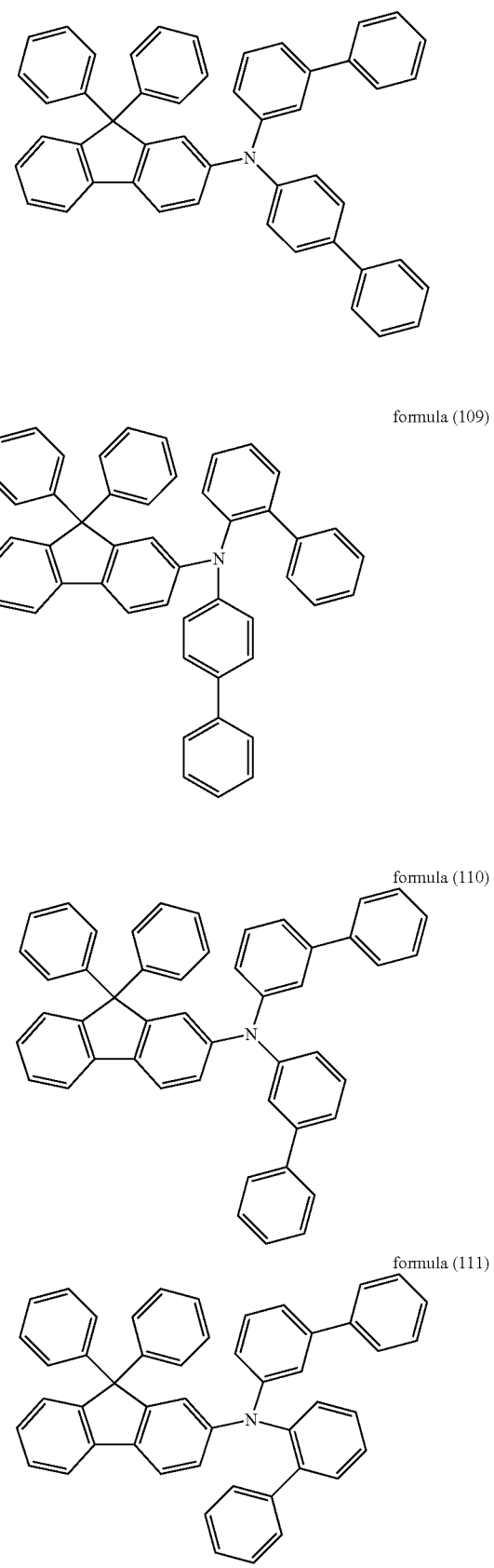

formula (112)
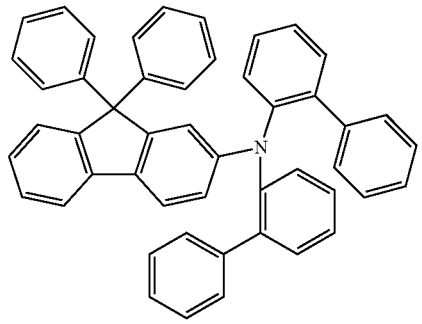
formula (113)
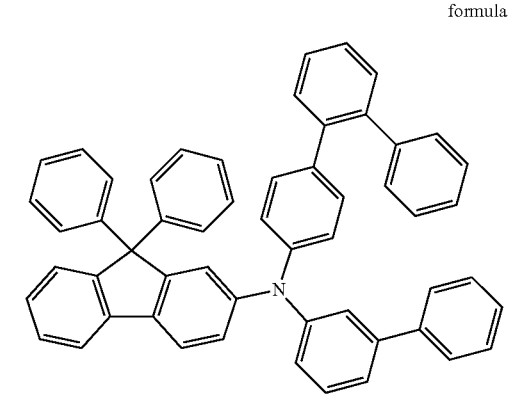
formula (114)
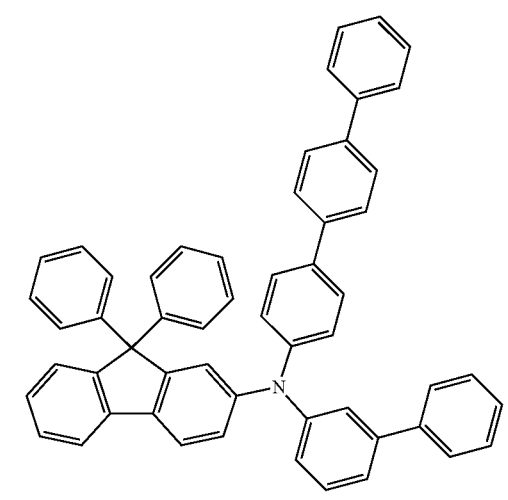
formula (115)
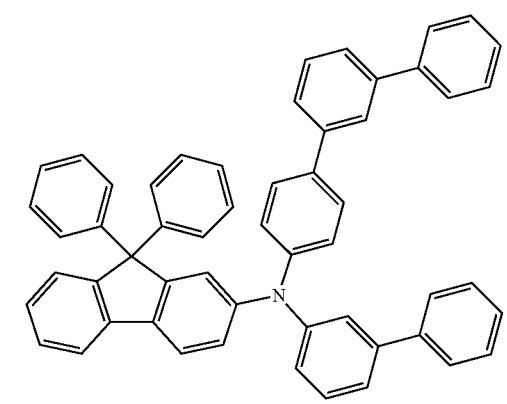
formula (116)
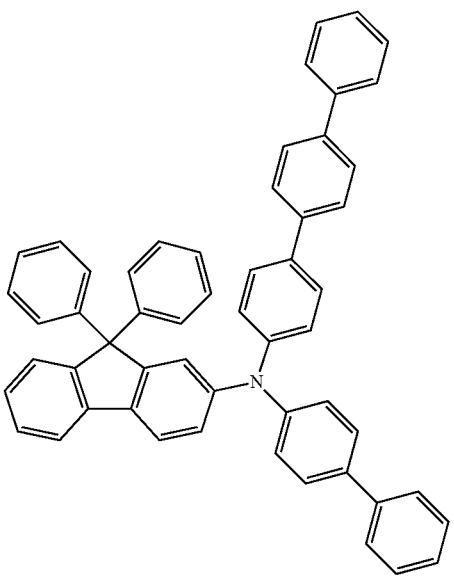
formula (117)
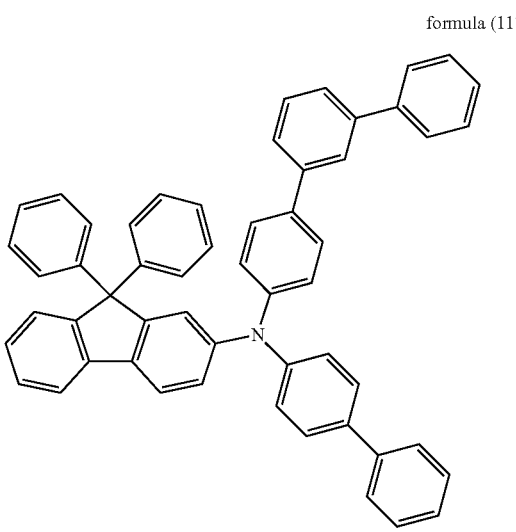
formula (118)
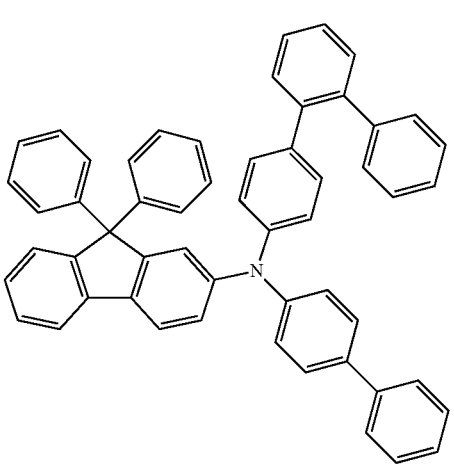

formula (119)
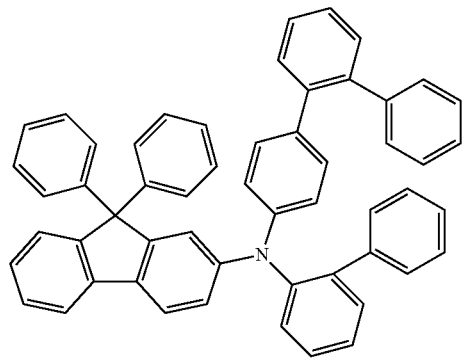
formula (120)
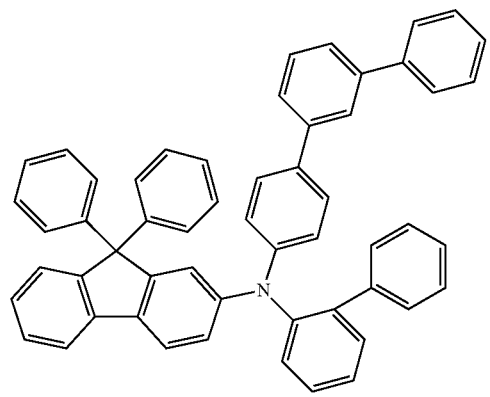
formula (121)
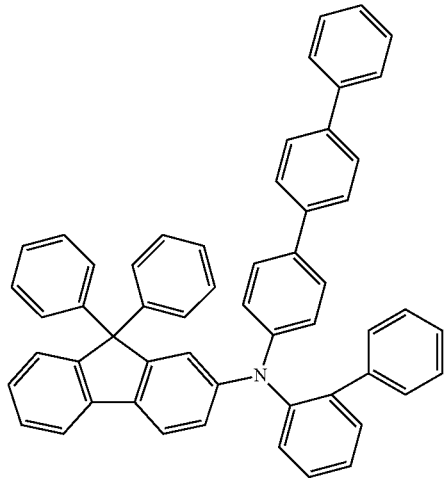
formula (122)
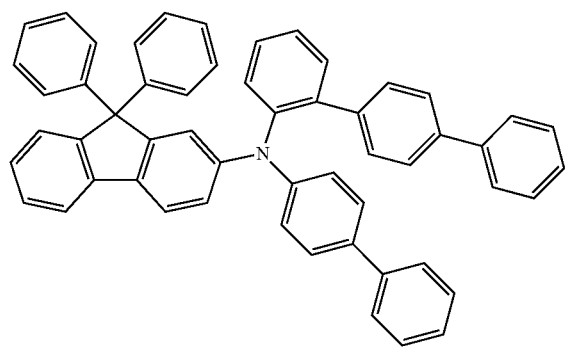
formula (123)
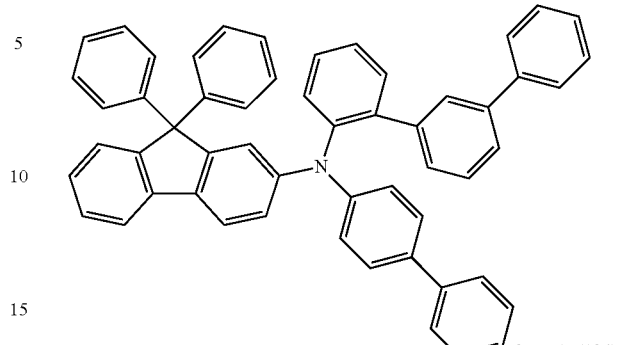
formula (124)
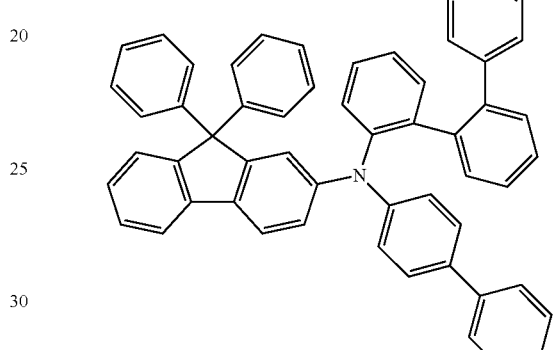
formula (125)
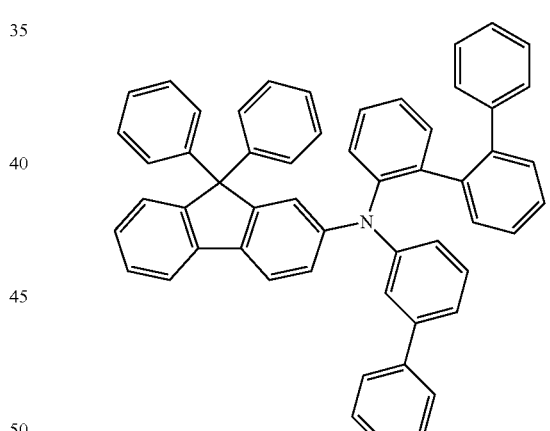
formula (126)
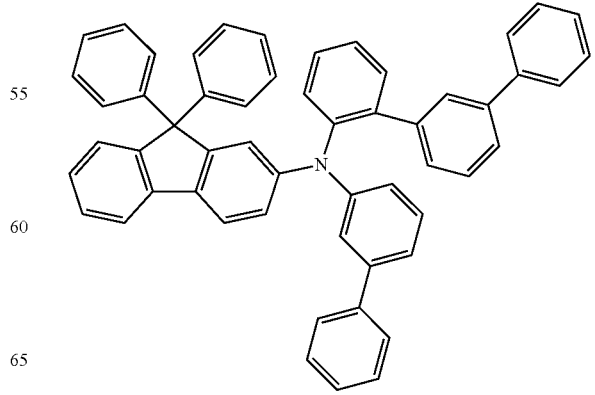

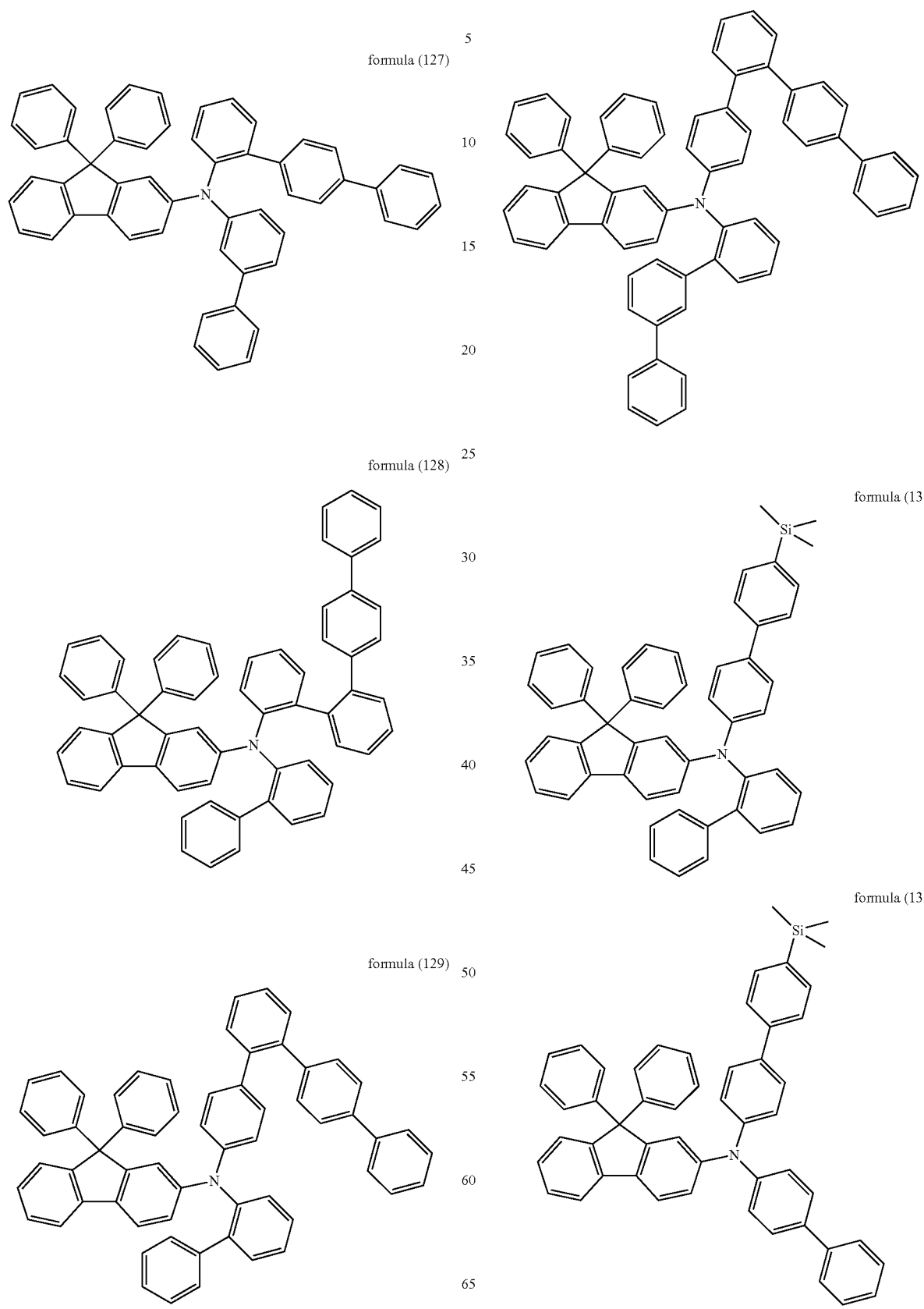

formula (133)
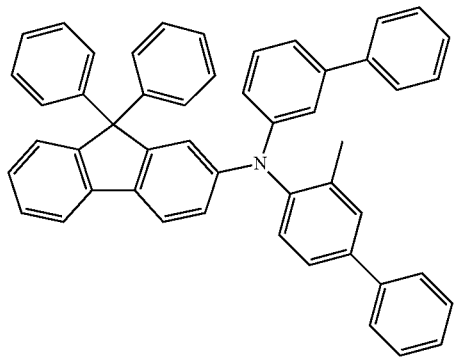
formula (134)
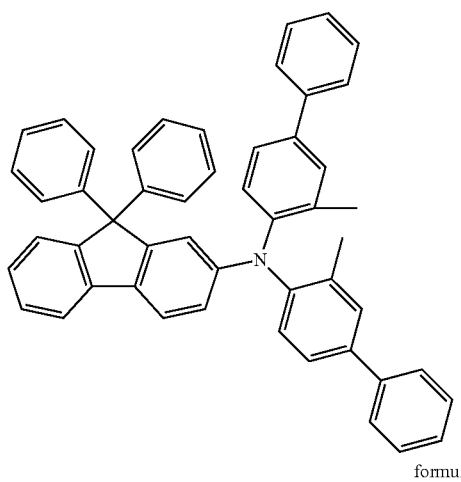
formula (135)
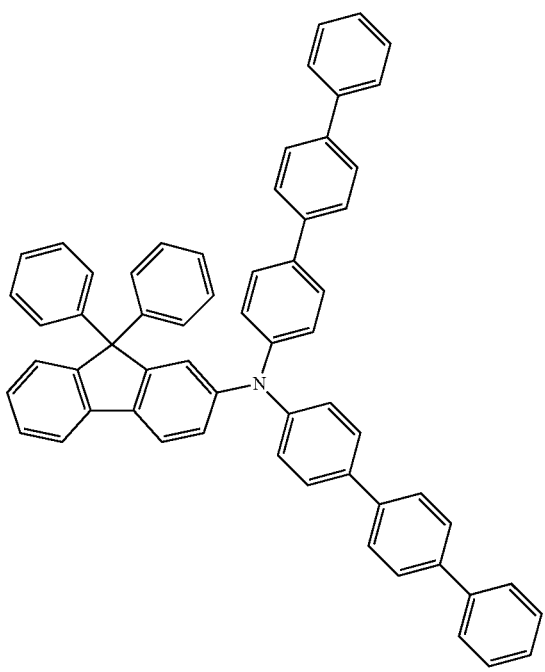
formula (136)
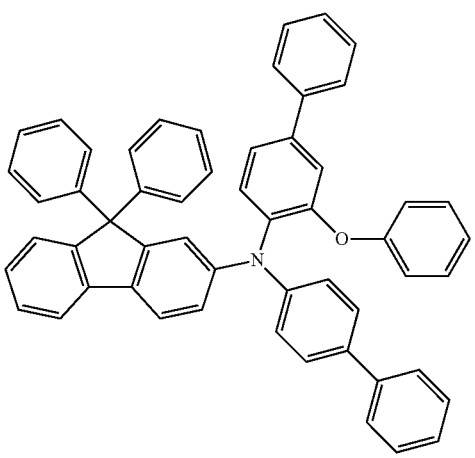
formula (137)
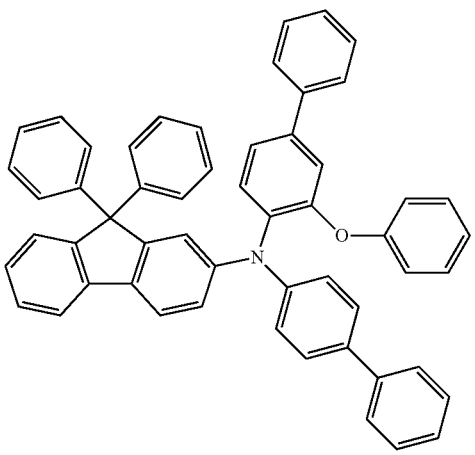
formula (138)
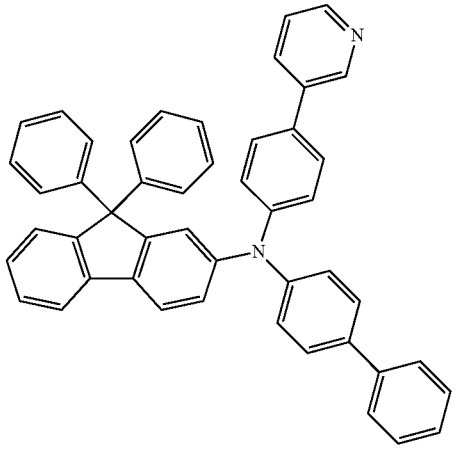

formula (139)
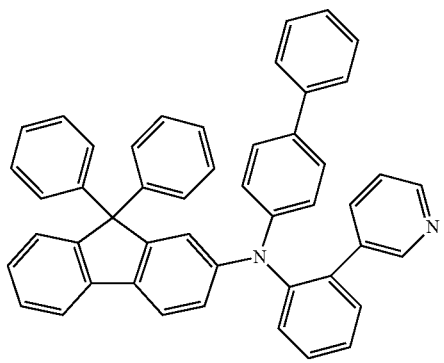
formula (140)
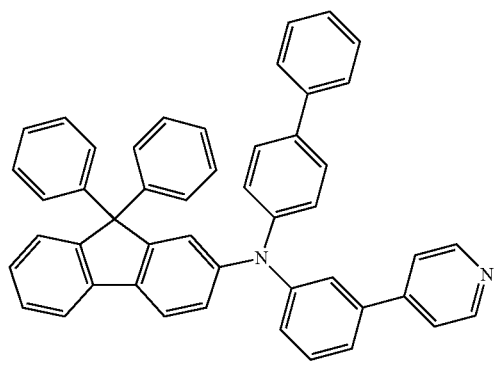
formula (141)
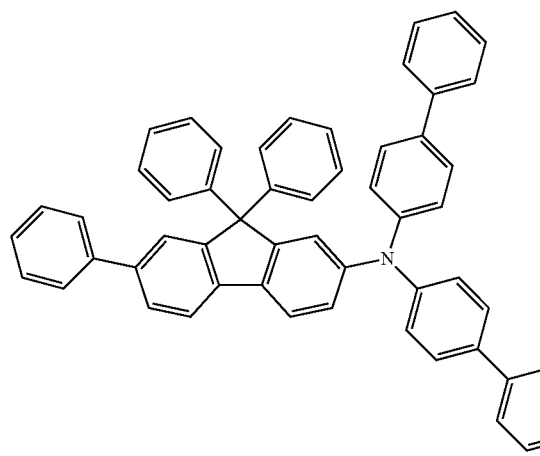
formula (142)
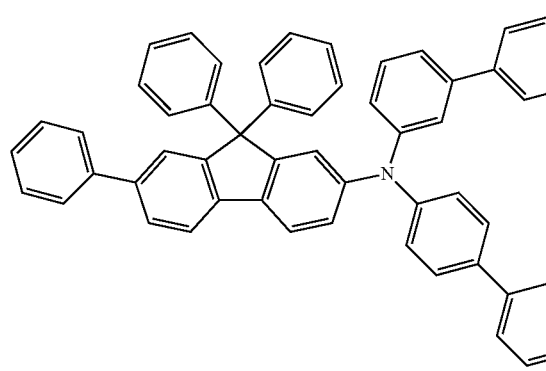
formula (143)
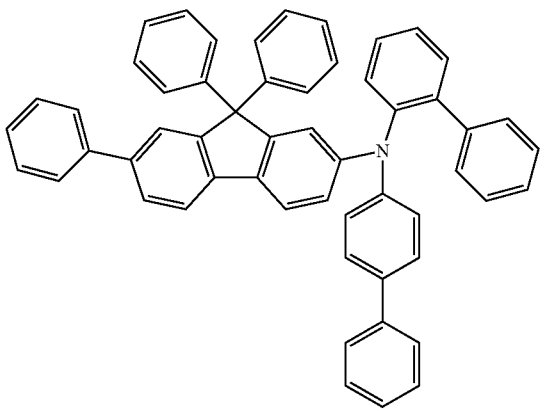
formula (144)
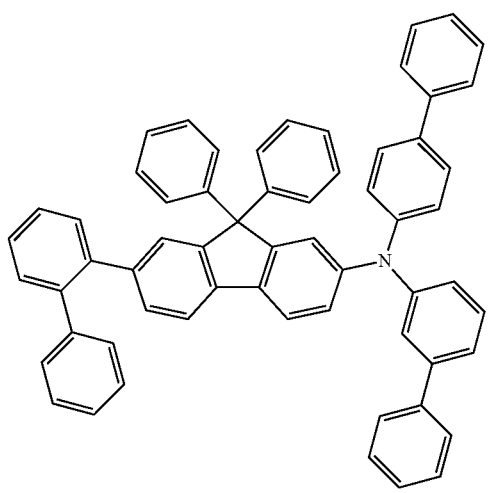
formula (145)
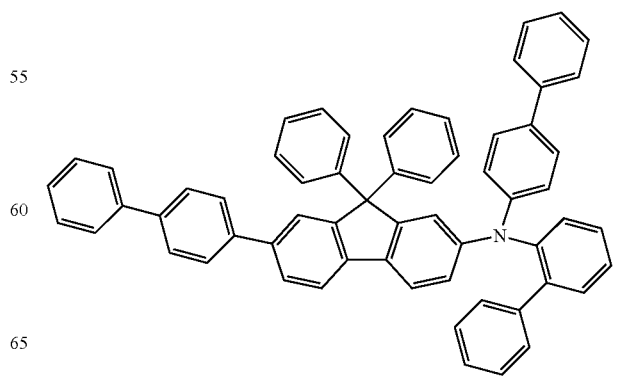

formula (146)
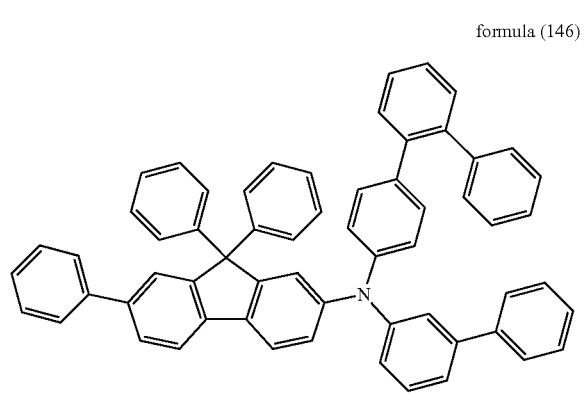
formula (147)
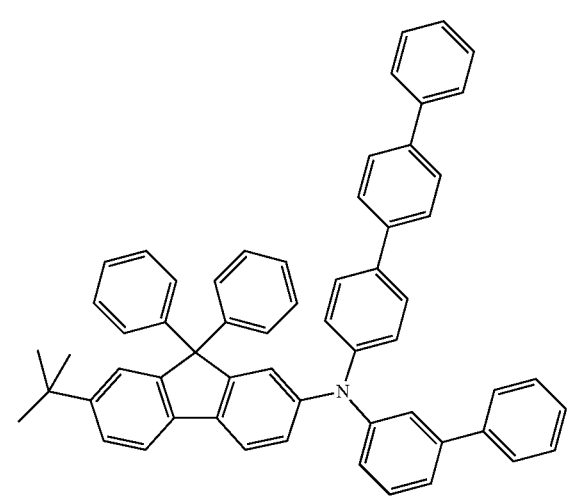
formula (148)
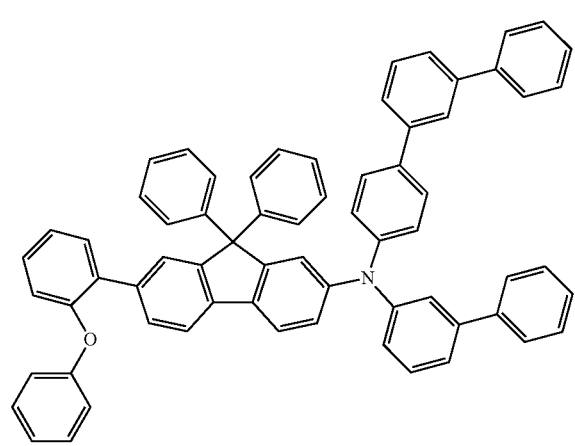
formula (149)
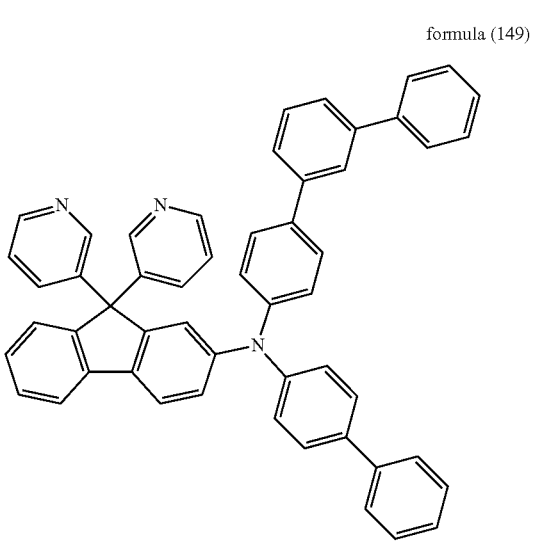
formula (150)
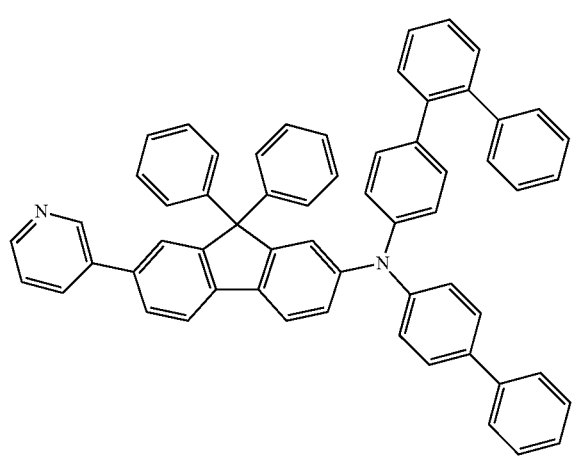
formula (151)
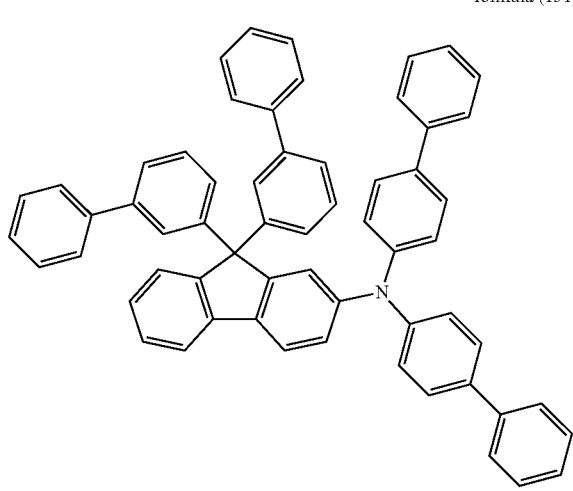

formula (152)
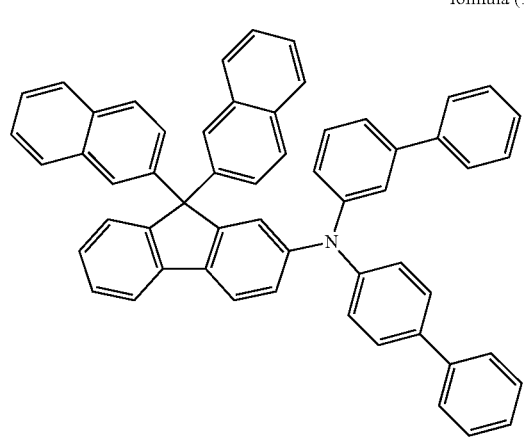
formula (153)
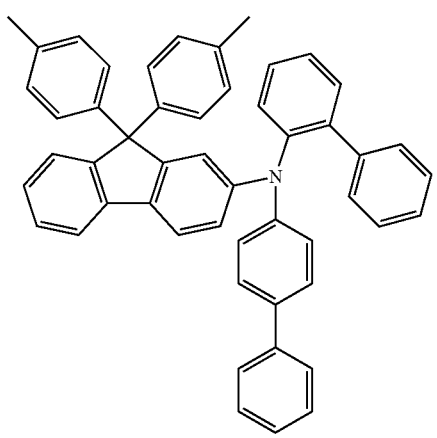
formula (154)
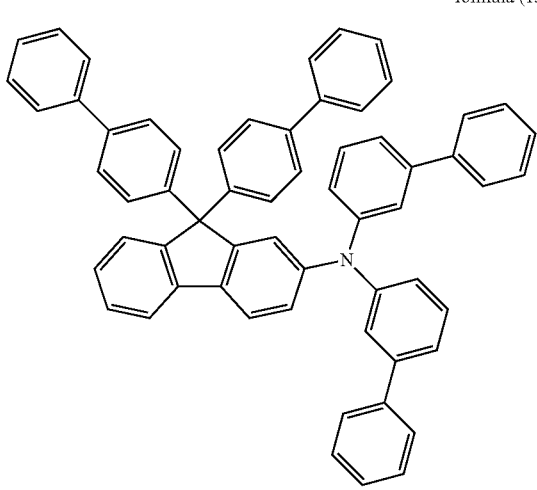
formula (155)
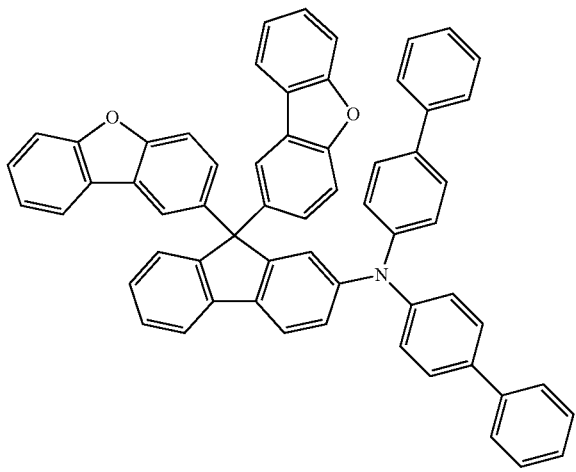
formula (156)
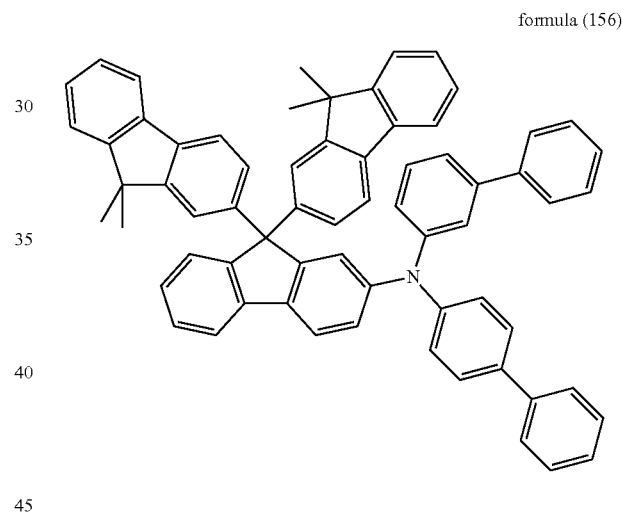
formula (157)
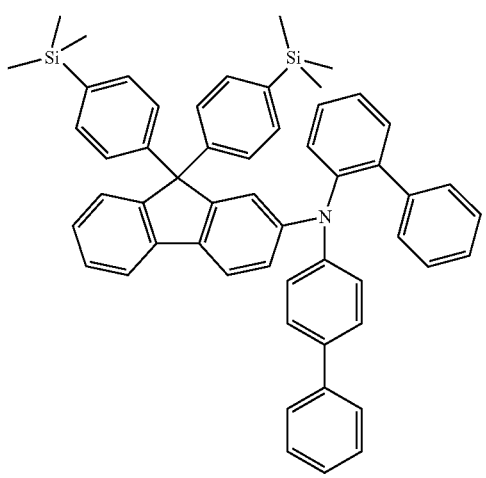

-continued
formula (158)
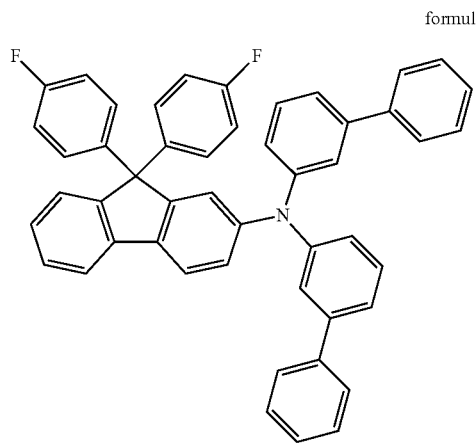
formula (159)
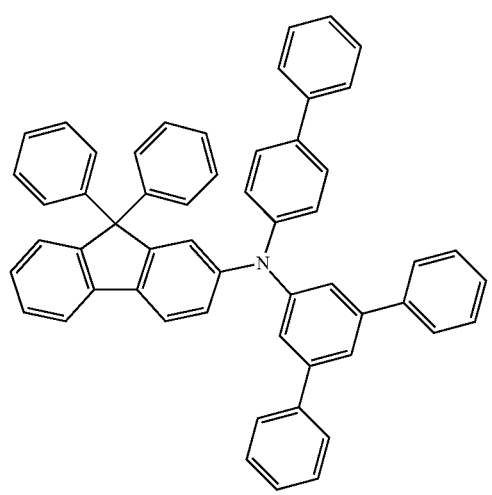
formula (160)
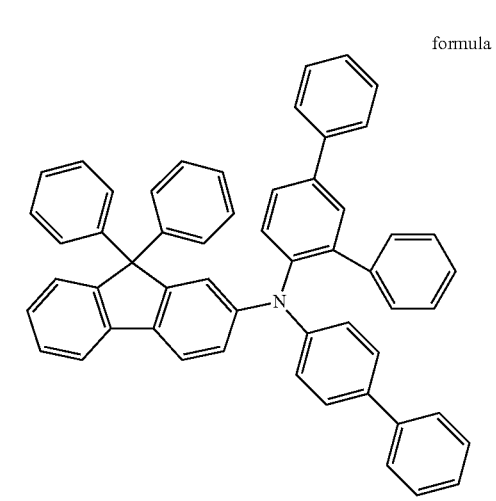
-continued
formula (161)
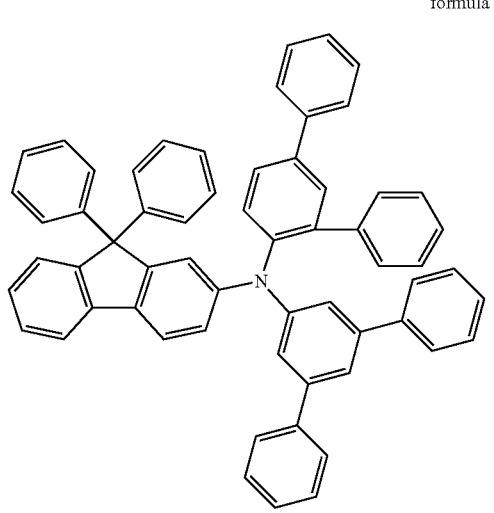
formula (162)
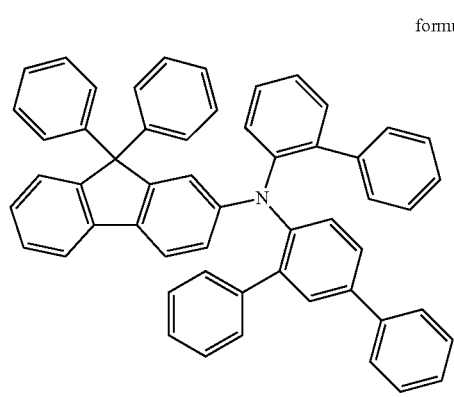
formula (163)
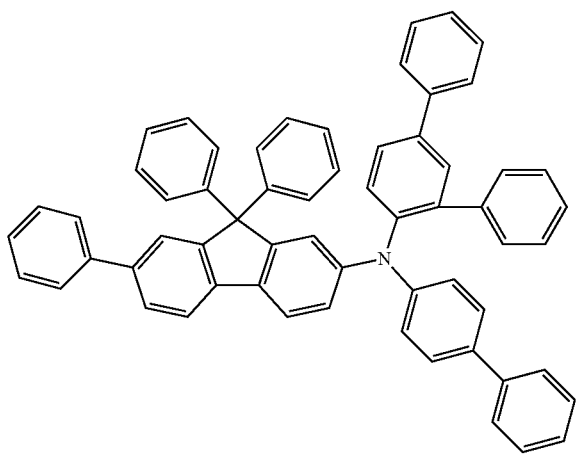

-continued formula (164)

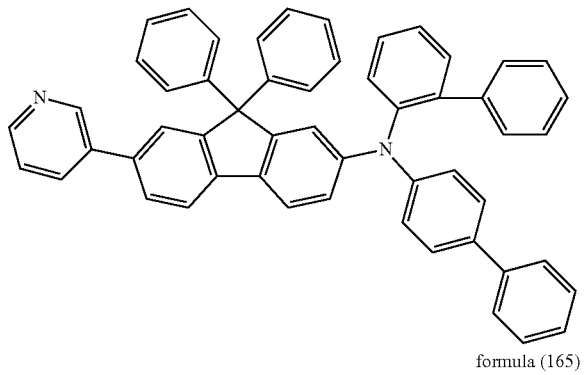

formula (165)

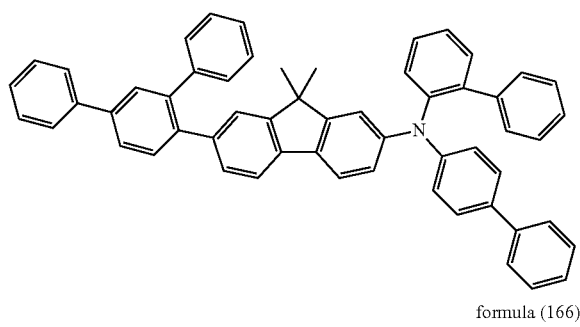

formula (166)

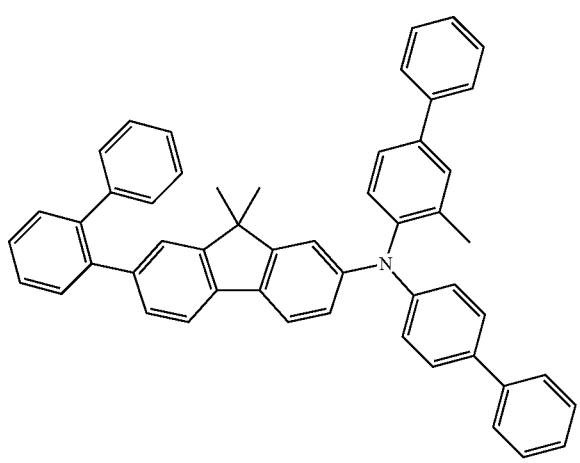

The present invention also relates to compounds of the general formula (167)

formula (167)

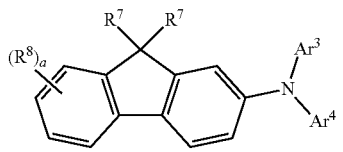

where the following applies to the symbols used in formula (167)

Ar³, Ar⁴
are on each occurrence, identically or differently, an aromatic or heteroaromatic ring system having 10 to 60 ring atoms, which may be substituted by one or more radicals R⁵, which are identical to or different from one another, where the two groups Ar³ and Ar⁴ each contain at least two or more aromatic or heteroaromatic, preferably aromatic, rings;

R⁷ is identical on each occurrence and is selected from the group consisting of a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals R⁵ and where one or more H atoms in the above-mentioned groups may be replaced by D, CN or NO₂, or an aromatic or heteroaromatic ring system having 6 to 30 ring atoms, which may in each case be substituted by one or more radicals R⁵, where R⁵ is defined as indicated above, or a condensed ring system having 9 to 30 ring atoms, which may in each case be substituted by one or more radicals R⁵, where, in the case of aromatic or heteroaromatic condensed rings, not more than 10 ring atoms may be present in the condensed ring system; the two radicals R⁷ may also form a ring closure with one another, so that a spiro compound forms, where no aromatic or heteroaromatic rings are condensed onto the ring formed by the two radicals R⁷, and where, if R⁷ is a straight-chain or branched alkyl group, R⁵ is an aromatic or heteroaromatic ring system having 6 to 30 ring atoms, which may in each case be substituted by one or more radicals R⁵, and where R⁵ is defined as indicated above;

R⁸ is H, D or an aromatic or heteroaromatic ring system having 6 to 30 ring atoms, which may in each case be substituted by one or more radicals R⁵, where R⁵ is defined as indicated above and where, if R⁸ is equal to H, R⁷ is an aromatic or heteroaromatic ring system having 6 to 30 aromatic ring atoms, which may in each case be substituted by one or more radicals R⁵, where R⁵ is defined as indicated above;

a is either 1, 2, 3 or 4, preferably 1 or 2, very preferably 1;

with the proviso that the compound of the formula (167), besides the one fluorene group and besides the possible condensed or polycyclic groups in position 9 of the fluorene, contains no further polycyclic or condensed groups and with the proviso that the compound contains no halogens.

It is preferred for the compound of the formula (167) to contain no further polycyclic or condensed groups besides the one fluorene group.

Compounds of the formula (167) where a=1 and R⁸ is in position 7 of the fluorene are preferred, i.e. compounds of the formula (168)

formula (168)

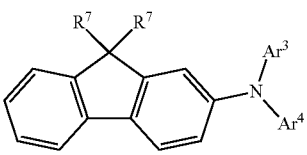

Particular preference is given to compounds of the formulae (167) and (168) where the following applies to the symbols used:

Ar³, Ar⁴
are selected on each occurrence, identically or differently, from biphenyl, terphenyl and quaterphenyl, each of which may be substituted by one or more radicals R⁵, where it is furthermore preferred for these to be unsubstituted;

R⁷ is identical on each occurrence and is selected from an aromatic or heteroaromatic ring system having 6 to 30 ring atoms, which may in each case be substituted by one or more radicals R⁵, where R⁵ is defined as indicated above, or a condensed ring system having 9 to 30 ring atoms, which may in each case be substituted by one or more radicals R⁵, where, in the case of aromatic or heteroaromatic condensed rings, not more than 10 ring atoms may be present in the condensed ring system;

with the proviso that the compound of the formula (168), besides the one fluorene group and besides the possible condensed or polycyclic groups in position 9 of the fluorene, contains no further polycyclic or condensed groups and with the proviso that the compound contains no halogens.

Furthermore preferred compounds of the formula (167) are those of the general formula (169)

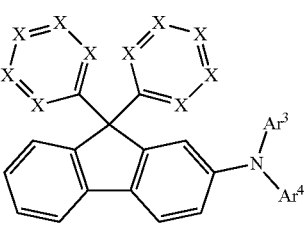

formula (169)

where X is, identically or differently on each occurrence, N or CR⁵ and R⁵, Ar³ and Ar⁴ are defined as indicated above. It is preferred for X in formula (169) to be equal to CR⁵.

Ar¹ and Ar³ in formula (169) are preferably selected on each occurrence, identically or differently, from biphenyl, terphenyl and quaterphenyl, each of which may be substituted by one or more radicals R⁵, where it is furthermore preferred for these to be unsubstituted.

Most preference is given to compounds of the formula (170)

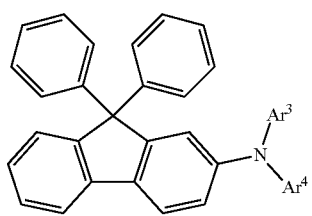

formula (170)

Ar¹ and Ar³ in formula (170) are preferably selected on each occurrence, identically or differently, from biphenyl, terphenyl and quaterphenyl, each of which may be substituted by one or more radicals R⁵, where it is furthermore preferred for these to be unsubstituted.

In a further preferred embodiment of the present invention, the compound is selected from the general formula (171)

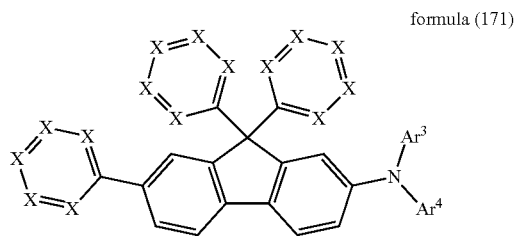

formula (171)

where the above definitions apply to the symbols used. Ar¹ and Ar³ in formula (171) are preferably selected on each occurrence, identically or differently, from biphenyl, terphenyl and quaterphenyl, each of which may be substituted by one or more radicals R⁵, where it is furthermore preferred for these to be unsubstituted.

Furthermore preferred compounds of the formula (5) are compounds of the formula (172)

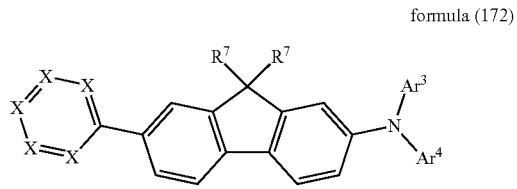

formula (172)

where the following applies to the symbols used:
X is, identically or differently on each occurrence, N or CR⁵ and preferably CR⁵, and R⁵ is defined as indicated above;
R⁷ is a straight-chain alkyl group having 1 to 20 C atoms or a branched or cyclic alkyl group having 3 to 20 C atoms, where the above-mentioned groups may each be substituted by one or more radicals R⁵ and where one or more H atoms in the above-mentioned groups may be replaced by D, CN or NO₂, where the two radicals R⁷ may also form a ring closure, so that a spiro compound forms, where no aromatic or heteroaromatic rings are condensed onto the ring formed by the two radicals R⁷;
and where Ar³ and Ar⁴ are defined as indicated above.

Ar¹ and Ar³ in formula (172) are preferably selected on each occurrence, identically or differently, from biphenyl, terphenyl and quaterphenyl, each of which may be substituted by one or more radicals R⁵, where it is furthermore preferred for these to be unsubstituted.

In a furthermore preferred embodiment of the present invention, the compound is selected from the general formula (173)

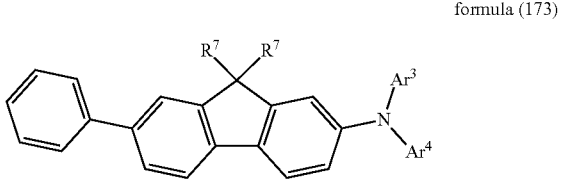

formula (173)

where the following applies to the symbols used:
R⁷ is a straight-chain alkyl group having 1 to 20 C atoms or a branched or cyclic alkyl group having 3 to 20 C atoms, where the above-mentioned groups may each be substituted by one or more radicals R⁵ and where one or more H atoms in the above-mentioned groups may be replaced by D, CN or NO$_2$, where the two radicals R$^7$ may also form a ring closure, so that a spiro compound forms, where no aromatic or heteroaromatic rings are condensed onto the ring formed by the two radicals R$^7$.

Ar$^1$ and Ar$^3$ in formula (173) are preferably selected on each occurrence, identically or differently, from biphenyl, terphenyl and quaterphenyl, each of which may be substituted by one or more radicals R$^5$, where it is furthermore preferred for these to be unsubstituted.

Very particular preference is given to compounds of the following formulae (174) to (236) shown by way of example:

formula (174)

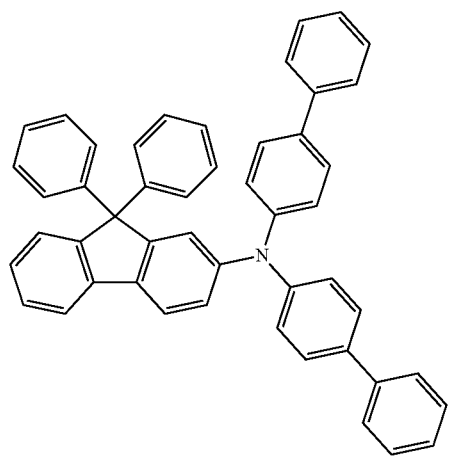

formula (175)

formula (176)

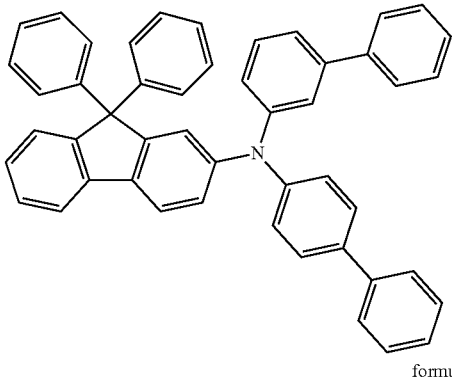

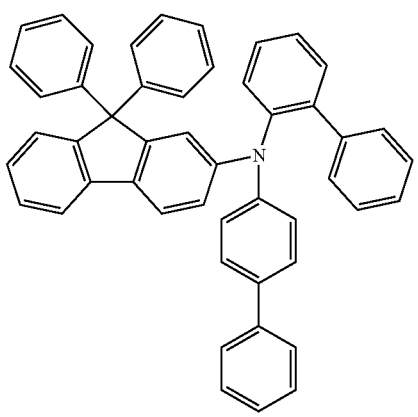

formula (177)

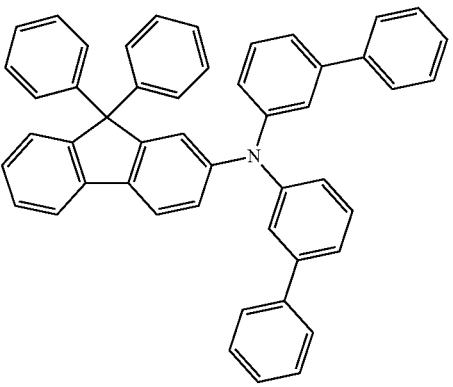

formula (178)

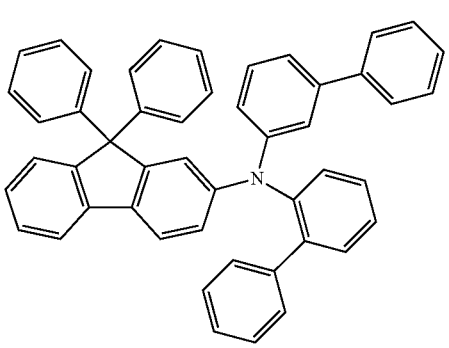

formula (179)

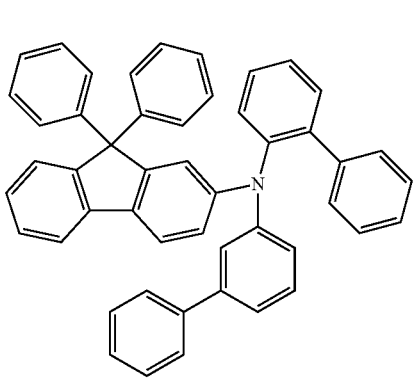

formula (180)

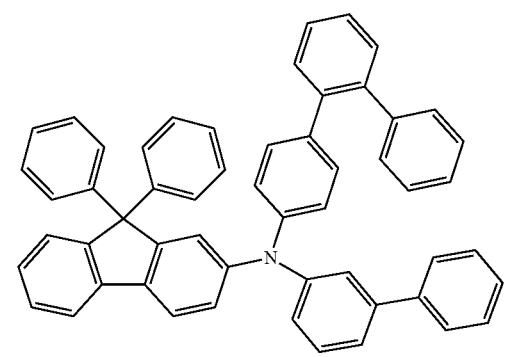

formula (181)
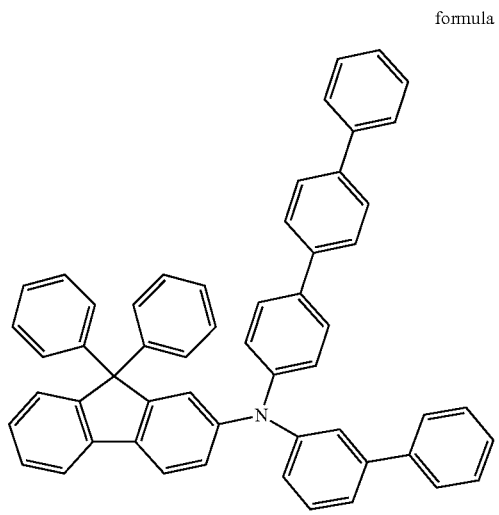
formula (182)
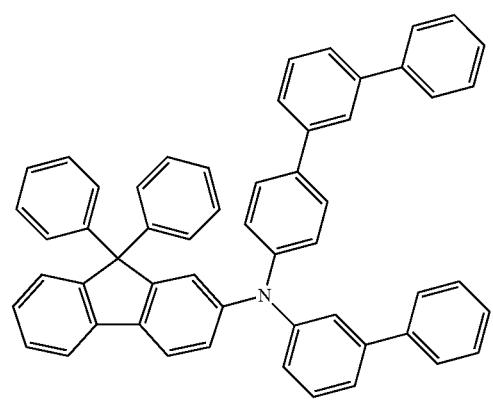
formula (183)
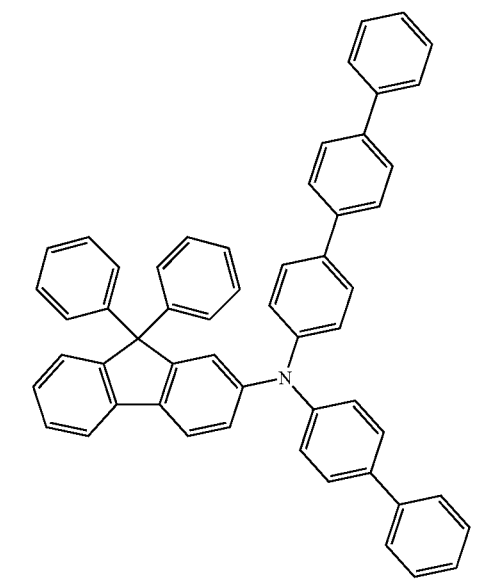
formula (184)
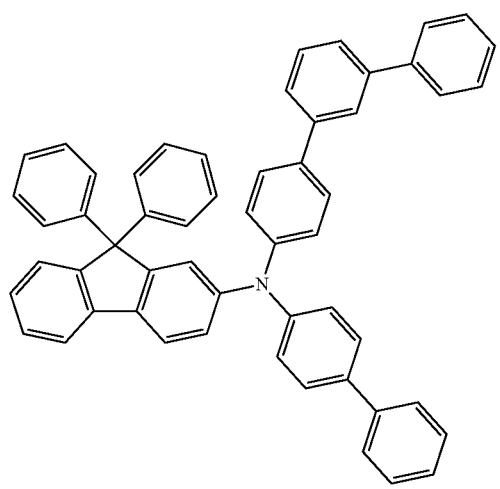
formula (185)
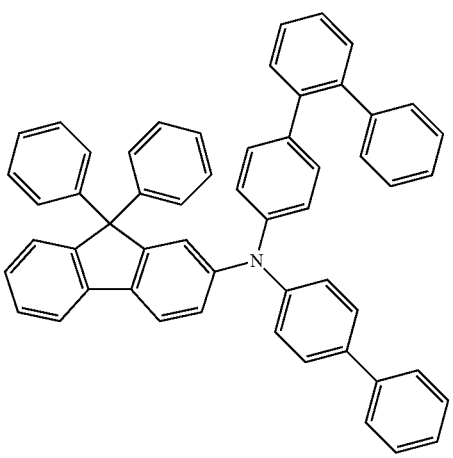
formula (186)
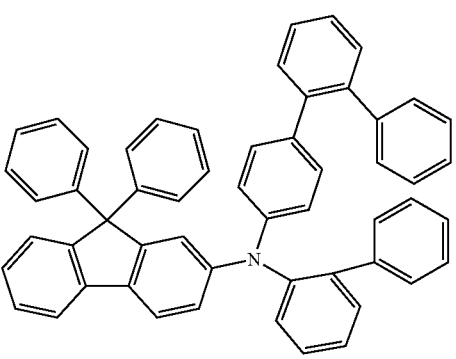

formula (187)
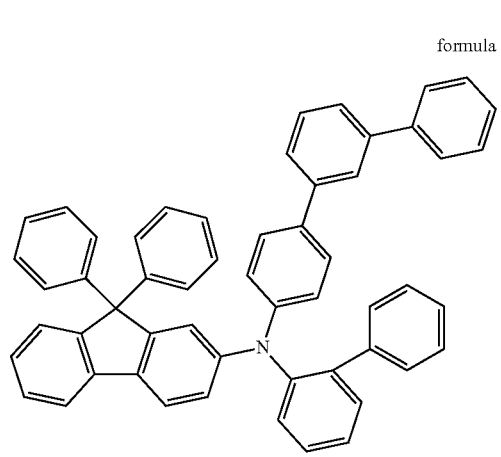
formula (188)
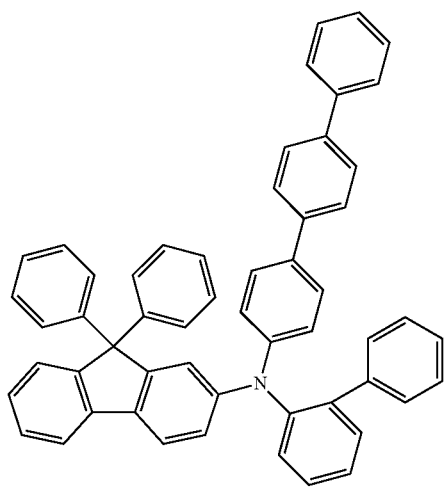
formula (189)
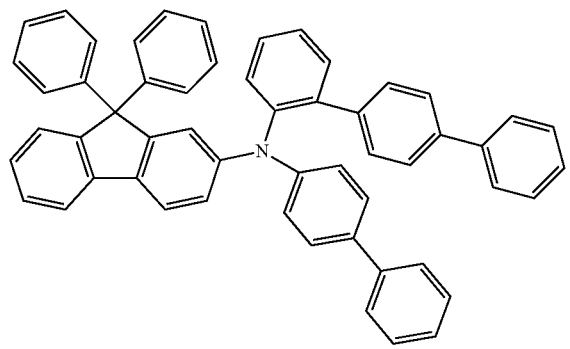
formula (190)
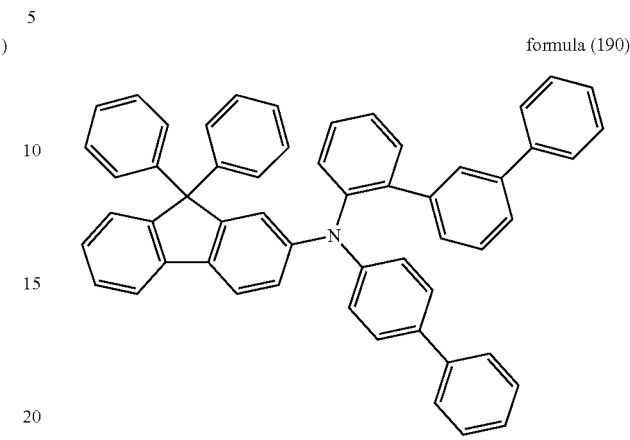
formula (191)
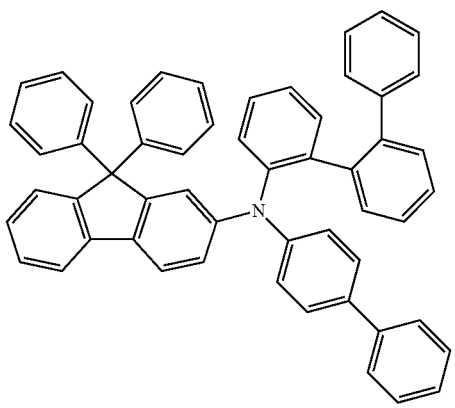
formula (192)
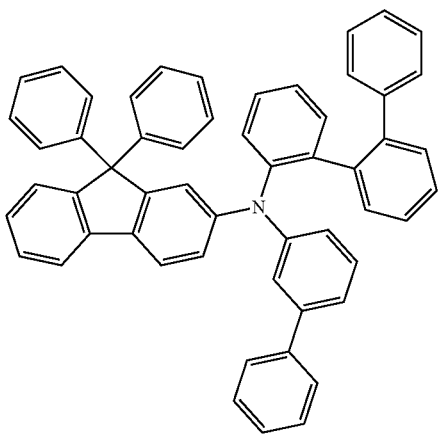

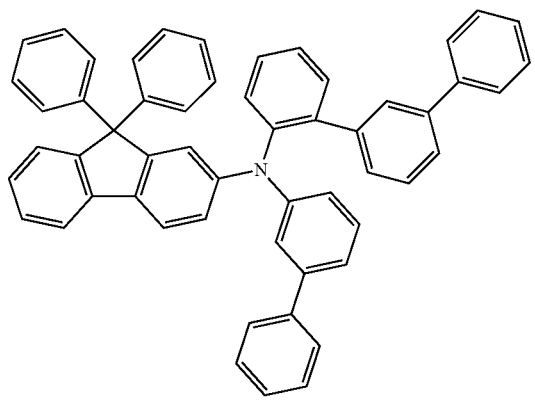
formula (193)
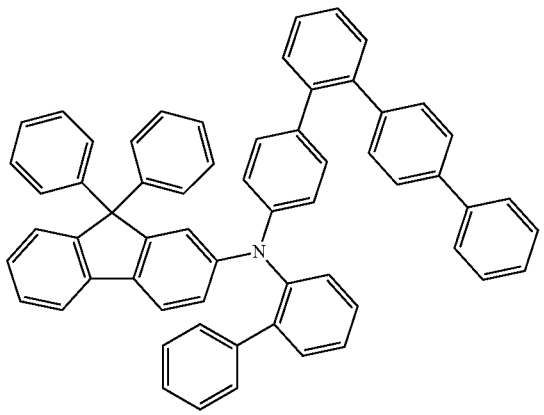
formula (196)
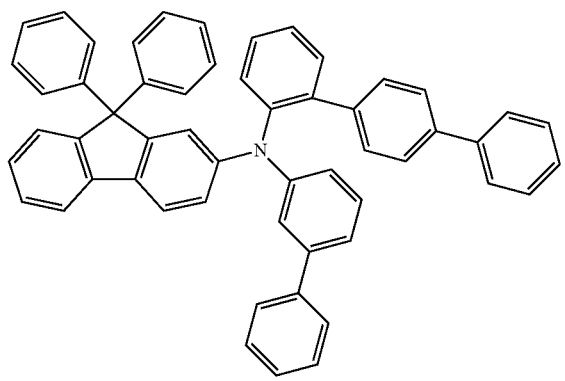
formula (194)
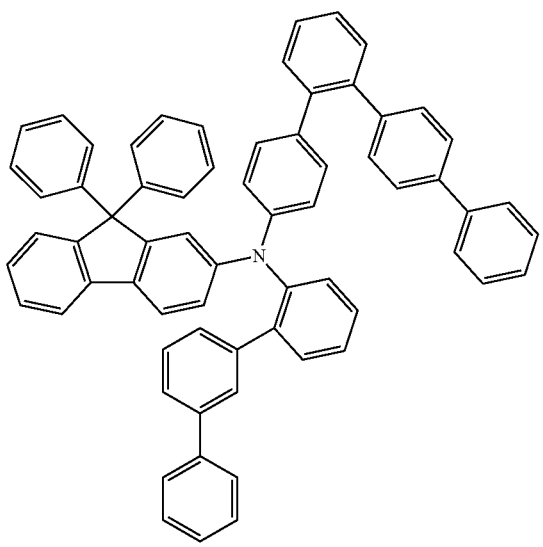
formula (197)
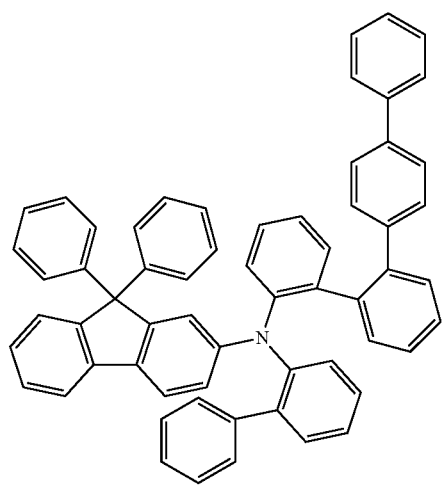
formula (195)
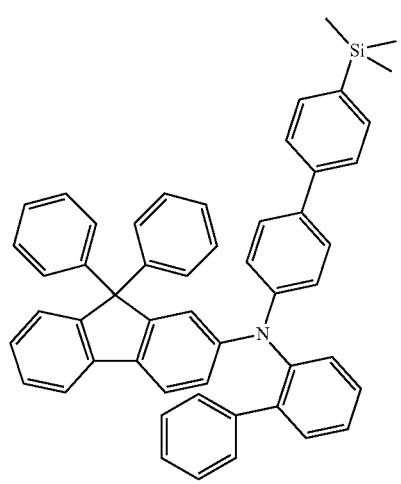
formula (198)

-continued
formula (199)
formula (200)
formula (201)
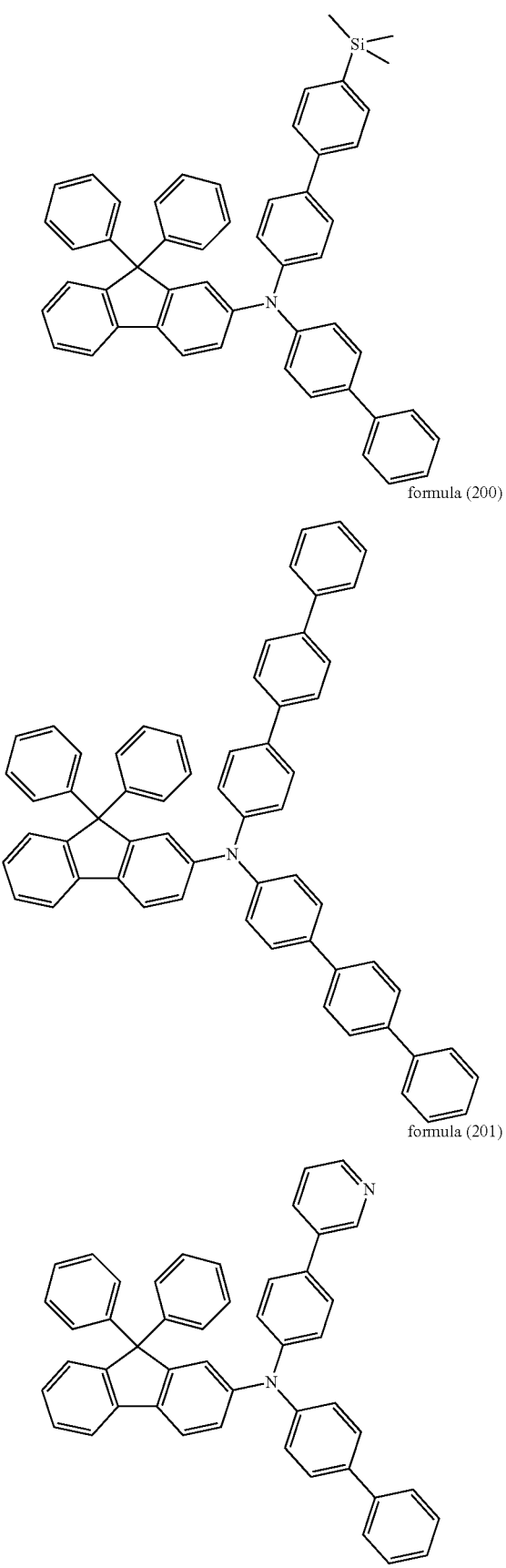
-continued
formula (202)
formula (203)
formula (204)
formula (205)
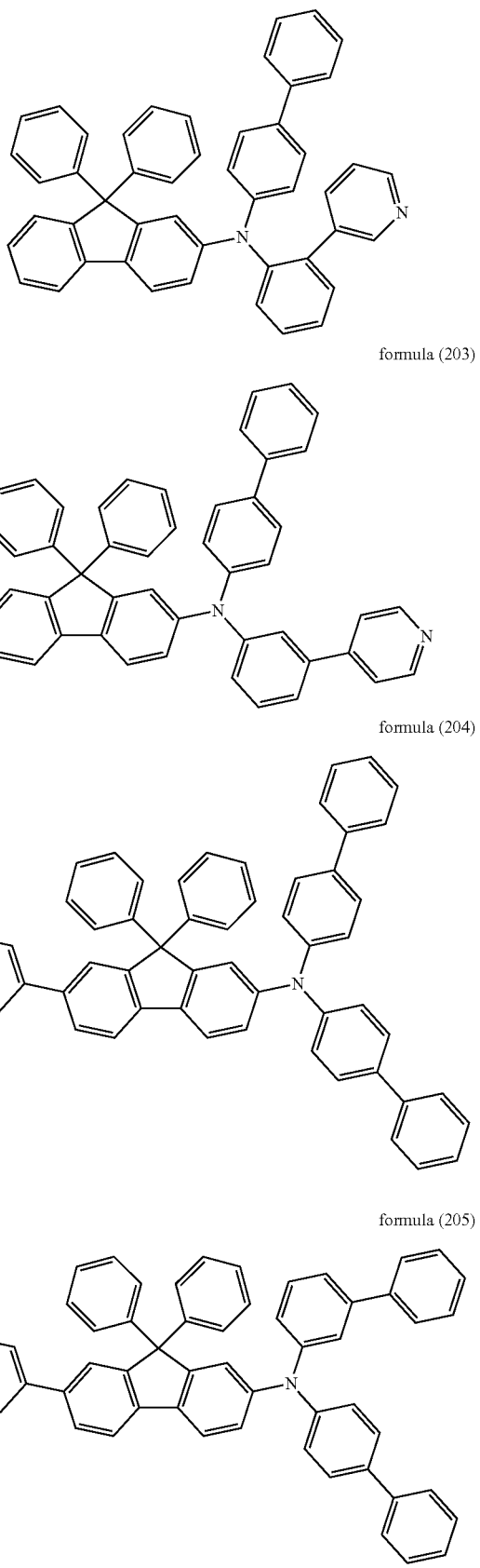

formula (206)
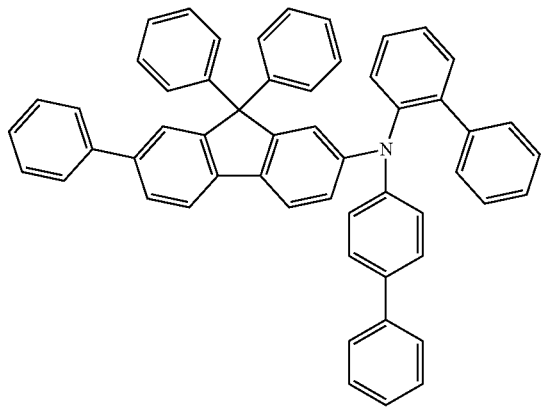
formula (207)
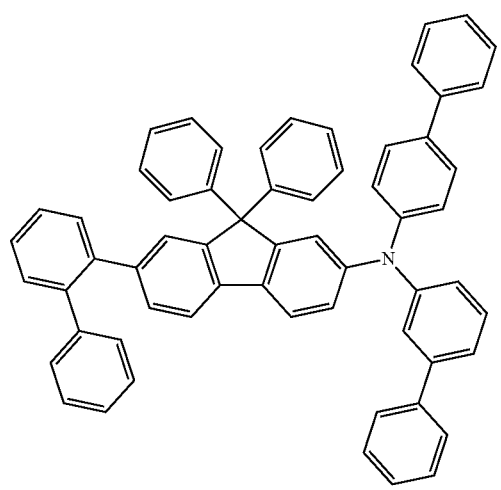
formula (208)
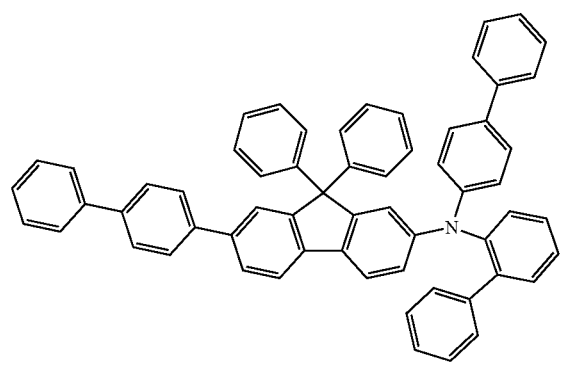
formula (209)
formula (210)
formula (211)
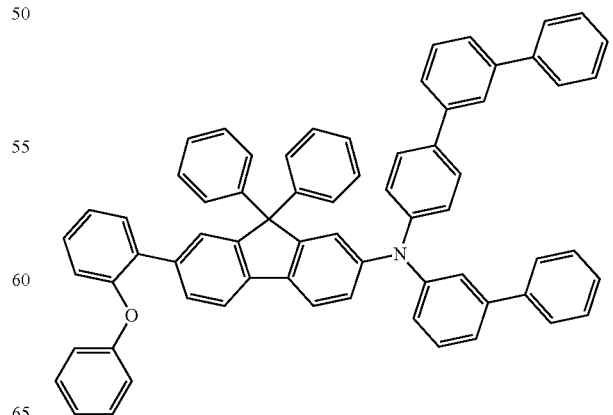

formula (212)
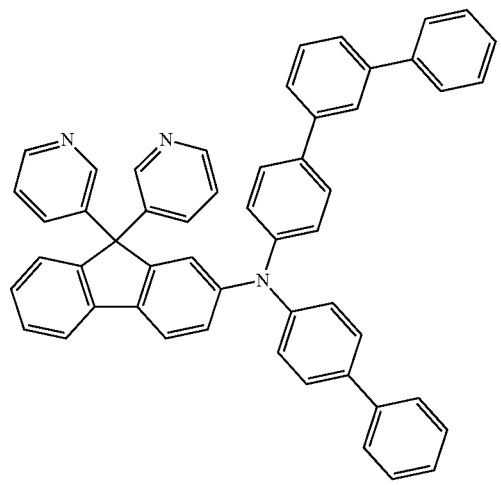
formula (215)
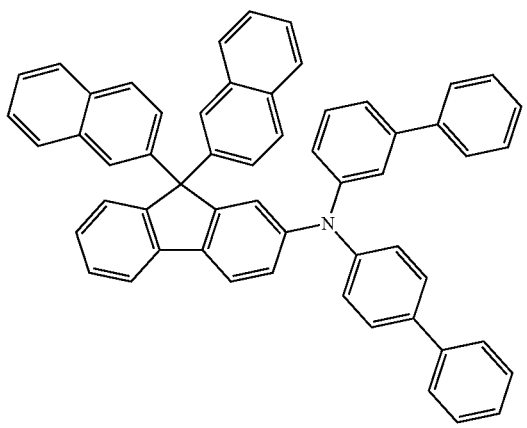
formula (213)
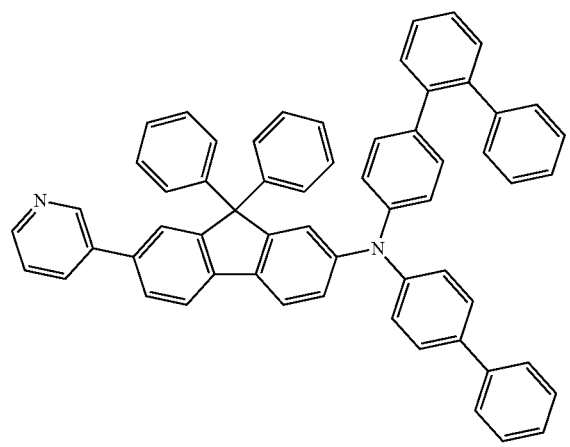
formula (216)
formula (214)
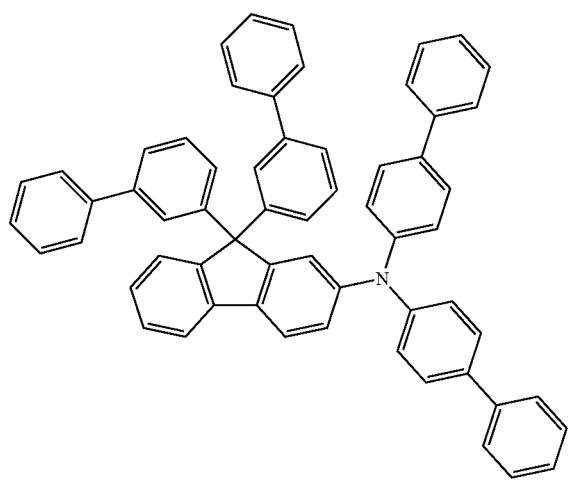
formula (217)
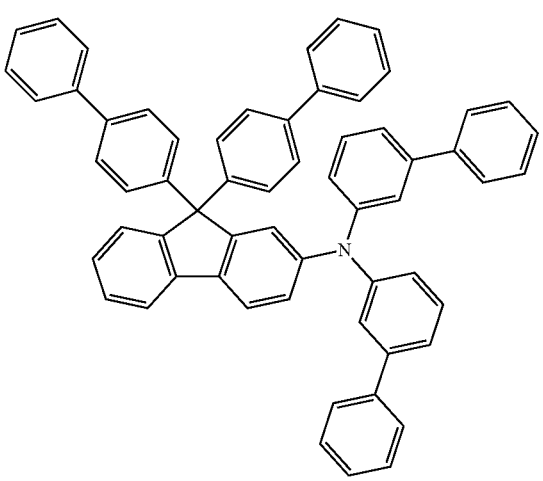

-continued
formula (218)
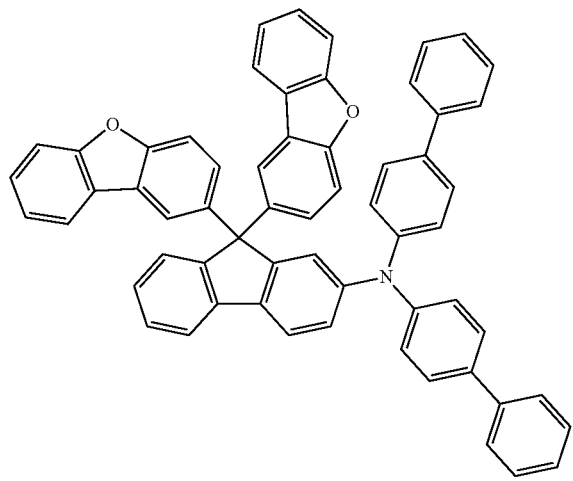
formula (219)
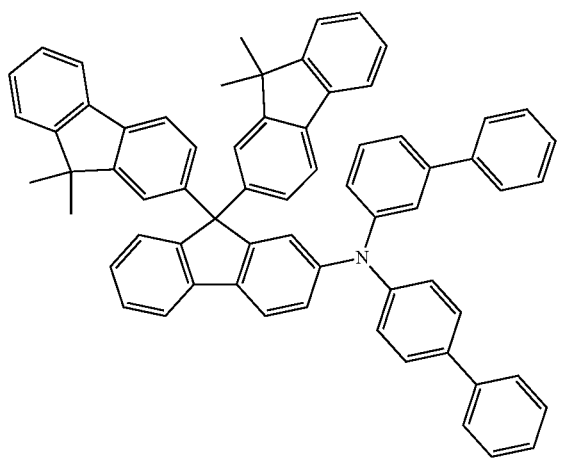
formula (202)
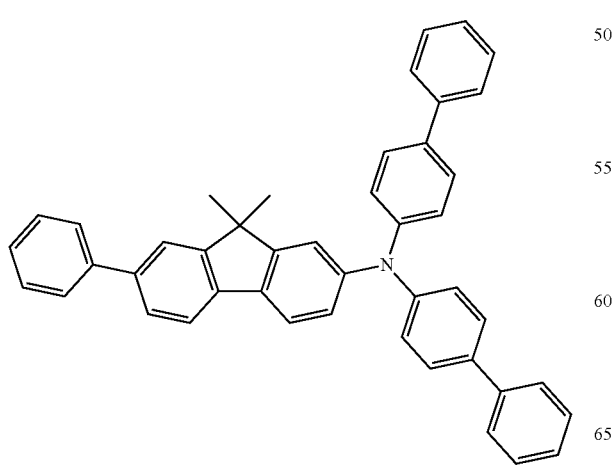
-continued
formula (221)
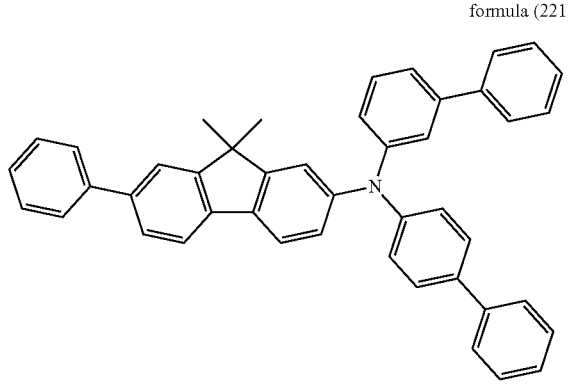
formula (222)
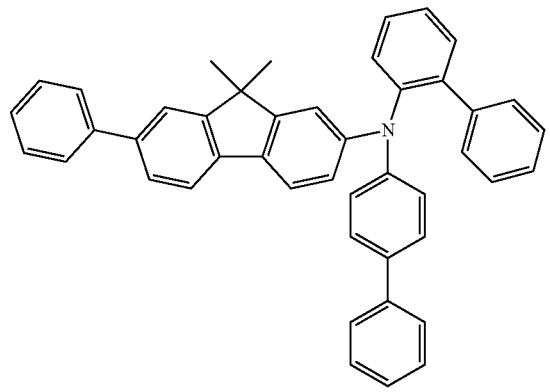
formula (223)
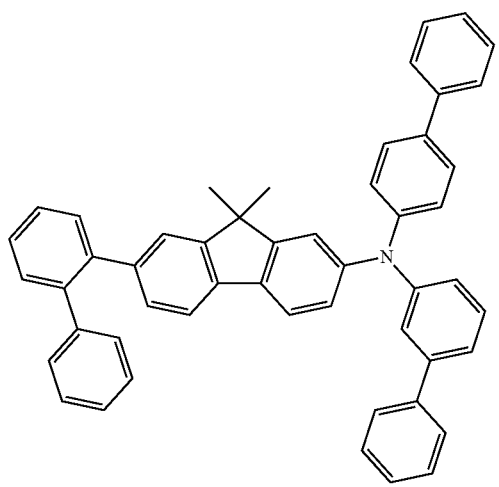

formula (224)
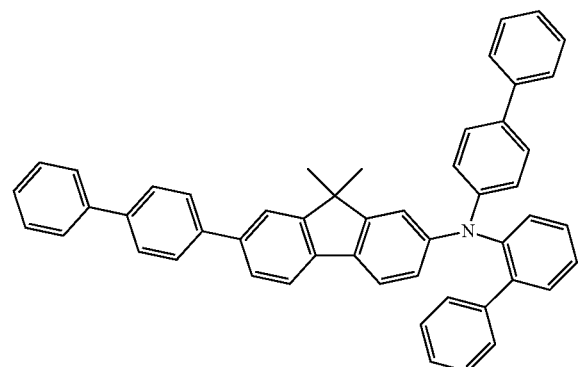
formula (225)
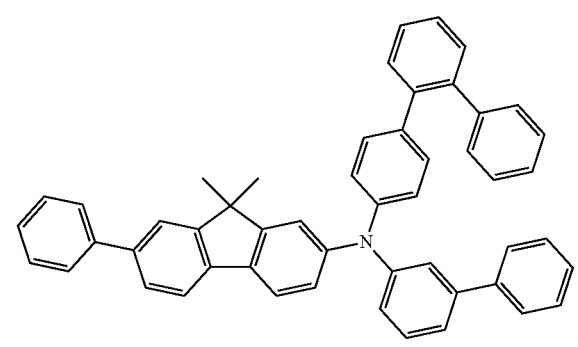
formula (226)
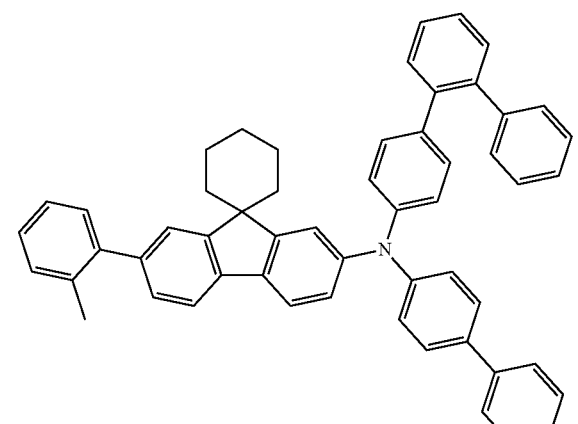
formula (227)
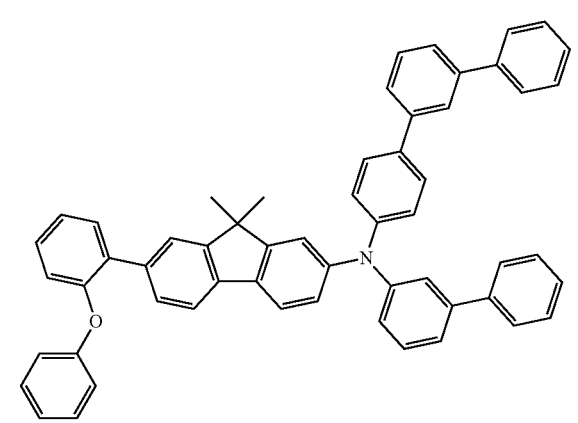
formula (228)
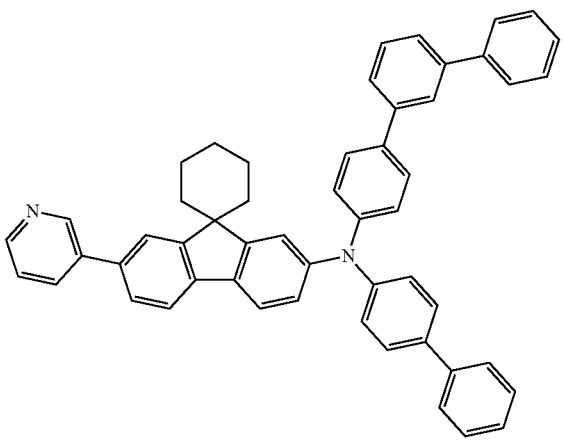
formula (229)
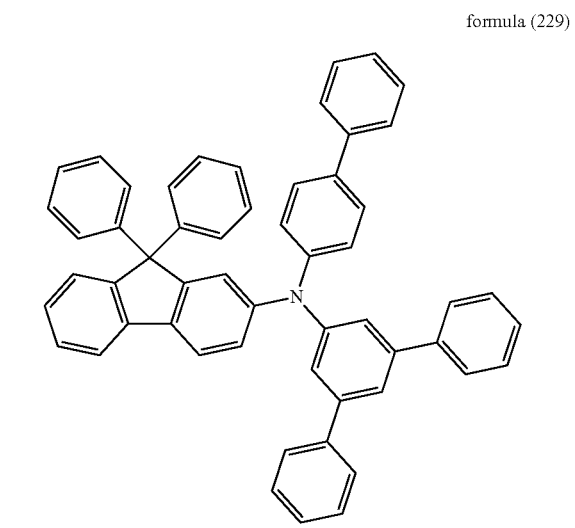
formula (230)
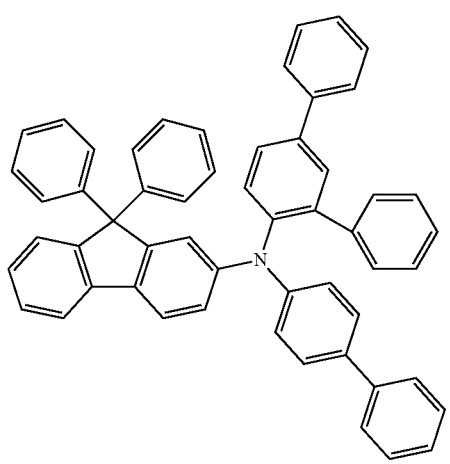

formula (231)

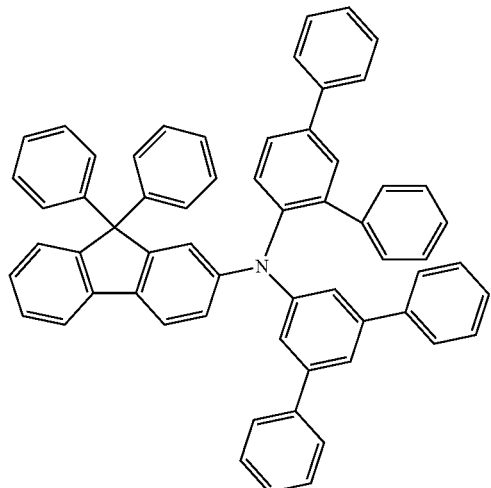

formula (232)

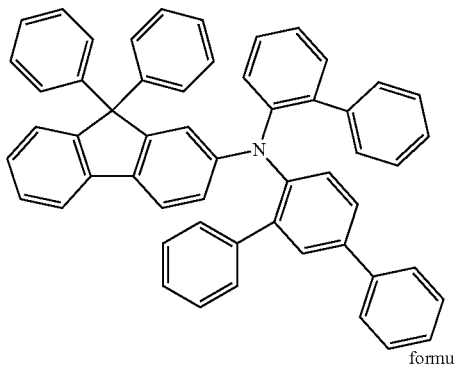

formula (233)

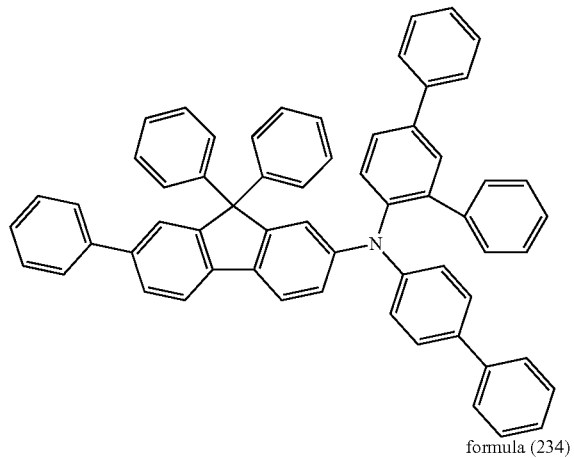

formula (234)

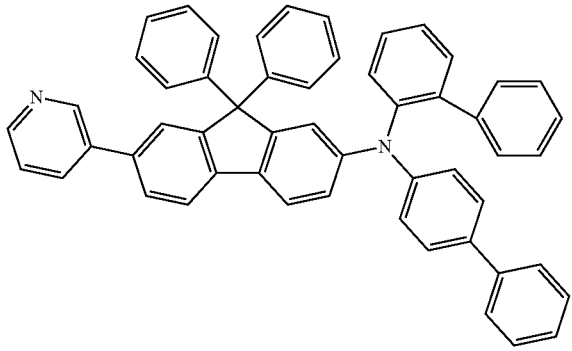

formula (236)

formula (236)

The compounds according to the invention can be employed as compositions with other organically functional materials which are used in electronic devices. A large number of possible organically functional materials is known to the person skilled in the art from the prior art. The present invention therefore also relates to a composition comprising one or more compounds of the formula (167) according to the invention and at least one further organically functional material selected from the group consisting of fluorescent emitters, phosphorescent emitters, host materials, matrix materials, electron-transport materials, electron-injection materials, hole-conductor materials, hole-injection materials, electron-blocking materials and hole-blocking materials.

For the processing of the compounds according to the invention from the liquid phase, for example by spin coating or by printing processes, formulations of the compounds according to the invention are necessary. These formulations can be, for example, solutions, dispersions or mini-emulsions. It may be preferred to use mixtures of two or more solvents for this purpose. Suitable and preferred solvents are, for example, toluene, anisole, o-, m- or p-xylene, methyl benzoate, dimethylanisole, mesitylene, tetralin, veratrol, THF, methyl-THF, THP, chlorobenzene, dioxane or mixtures of these solvents.

The invention therefore furthermore relates to a formulation, in particular a solution, dispersion or mini-emulsion, comprising at least one compound of the formula (167) or at least one polymer, oligomer or dendrimer containing at least one unit of the formula (167), and at least one solvent, preferably an organic solvent. The way in which solutions of this type can be prepared is known to the person skilled in the art and is described, for example, in WO 2002/072714, WO 2003/019694 and the literature cited therein.

The compounds according to the invention are suitable for use in electronic devices, in particular in organic electroluminescent devices (for example OLEDs or OLECs). Depending on the substitution, the compounds are employed in different functions and layers.

The present invention therefore furthermore relates to the use of the compounds of the formula (167) in electronic devices and to electronic devices themselves which comprise one or more compounds of the formula (167). The electronic devices here are preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and particularly preferably organic electroluminescent devices (OLEDs and OLECs).

The invention relates, as already stated above, to electronic devices comprising at least one compound of the formula (167). The electronic devices here are preferably selected from the devices mentioned above. Particular preference is given to organic electroluminescent devices (OLEDs) comprising anode, cathode and at least one emitting layer, characterised in that at least one organic layer, which may be an emitting layer, a hole-transport layer or another layer, comprises at least one compound of the formula (167).

An aryl group in the sense of this invention contains 6 to 60 aromatic ring atoms; a heteroaryl group in the sense of this invention contains 5 to 60 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or hetero-aromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzo-pyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in accordance with the definition of the present invention is taken to mean an aryl group, as defined above, which is bonded via an oxygen atom. An analogous definition applies to heteroaryloxy groups.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzo-pyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cyclo-heptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The compounds of the formula (1) described above may be substituted by reactive leaving groups, such as bromine, iodine, chlorine, boronic acid or boronic acid ester. These can be used as monomers for the production of corresponding oligomers, dendrimers or polymers. Suitable reactive leaving groups are, for example, bromine, iodine, chlorine, boronic acids, boronic acid esters, amines, alkenyl or alkynyl groups having a terminal C—C double bond or C—C triple bond, oxiranes, oxetanes, groups which undergo a cycloaddition, for example a 1,3-dipolar cycloaddition, such as, for example, dienes or azides, carboxylic acid derivatives, alcohols and silanes.

The invention therefore furthermore relates to oligomers, polymers or dendrimers containing one or more compounds of the formula (1), where the bond(s) to the polymer, oligomer or dendrimer may be localised at any desired possible positions in formula (1). Depending on the linking of the compound of the formula (1), the compound is a constituent of a side chain of the oligomer or polymer or a constituent of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (1) may be linked directly to one another or they may be linked to one another via a divalent group, for example via a substituted or unsubstituted alkylene group, via a heteroatom or via a divalent aromatic or heteroaromatic group. In branched and dendritic structures, for example, three or more units of the formula (1) may be linked via a trivalent or polyvalent group, for example via a trivalent or polyvalent aromatic or heteroaromatic group, to form a branched or dendritic oligomer or polymer.

The same preferences as described above for compounds of the formula (1) apply to the recurring units of the formula (1) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 2000/22026), spirobifluorenes (for example in accordance with EP 707020, EP 894107 or WO 2006/061181), para-phenylenes (for example in accordance with WO 1992/18552), carbazoles (for example in accordance with WO 2004/070772 or WO 2004/113468), thiophenes (for example in accordance with EP 1028136), dihydrophenanthrenes (for example in accordance with WO 2005/014689 or WO 2007/006383), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also contain further units, for example emitting (fluorescent or phosphorescent) units, such as, for example, vinyltriarylamines (for example in accordance with WO 2007/068325) or phosphorescent metal complexes (for example in accordance with WO 2006/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, at least one monomer of which results in recurring units of the formula (1) in the polymer. Suitable polymerisation reactions are known to the person skilled in the art and are described in the literature. Particularly suitable and preferred polymerisation reactions which result in C—C or C—N links are the following:

(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

The present invention thus also relates to a process for the preparation of the polymers, oligomers and dendrimers according to the invention, which is characterised in that they are prepared by SUZUKI polymerisation, YAMAMOTO polymerisation, STILLE polymerisation or HARTWIG-BUCHWALD polymerisation. The dendrimers according to the invention can be prepared by processes known to the person skilled in the art or analogously thereto. Suitable processes are described in the literature, such as, for example, in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6; WO 2002/067343 A1 and WO 2005/026144 A1.

Apart from the cathode, anode and emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, interlayers, charge-generation layers (IDMC 2003, Taiwan; Session 21 OLED (5), T. Matsumoto, T. Nakada, J. Endo, K. Mori, N. Kawamura, A. Yokoi, J. Kido, Multiphoton Organic EL Device Having Charge Generation Layer) and/or Organic or in-organic pin junctions. However, it should be pointed out that each of these layers does not necessarily have to be present and the choice of layers is always dependent on the compounds used and in particular also on whether the electroluminescent device is fluorescent or phosphorescent.

The organic electroluminescent device according to the invention may comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and which emit blue or yellow or orange or red light are used in the emitting layers. Particular preference is given to three-layer systems, i.e. systems having three emitting layers, where the three layers exhibit blue, green and orange or red emission (for the basic structure see, for example, WO 2005/011013). The compounds according to the invention may be present in such devices in a hole-transport layer, an emitting layer and/or in another layer. It should be noted that, for the generation of white light, an emitter compound used individually which emits in a broad wavelength range may also be suitable instead of a plurality of emitter compounds emitting in a colour.

It is preferred in accordance with the invention for the compound of the formula (1) to be employed in an electroluminescent device comprising one or more phosphorescent dopants. The compound can be used in various layers here, preferably in an hole-transport layer, a hole-injection layer or in an emitting layer. However, the compound of the formula (1) can also be employed in accordance with the invention in an electronic device comprising one or more fluorescent dopants.

The term phosphorescent dopants typically encompasses compounds in which the light emission takes place by a spin-forbidden transition, for example a transition from an excited triplet state or a state having a relatively high spin quantum number, for example a quintet state.

Suitable phosphorescent dopants (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present invention, all luminescent iridium, platinum or copper complexes are regarded as phosphorescent compounds.

Examples of the emitters described above are revealed by the applications WO 00/70655, WO 01/41512, WO 02/02714, WO 02/15645, EP 1191613, EP 1191612, EP 1191614, WO 05/033244, WO 2005/019373 and US 2005/0258742. In general, all phosphorescent complexes as used in accordance with the prior art for phosphorescent OLEDs and as are known to the person skilled in the art in the area of organic electroluminescent devices are suitable. The person skilled in the art will also be able to employ further phosphorescent complexes without inventive step in combination with the compounds of the formula (1) in organic electroluminescent devices.

Explicit examples of suitable phosphorescent emitter compounds are furthermore revealed by the following table.

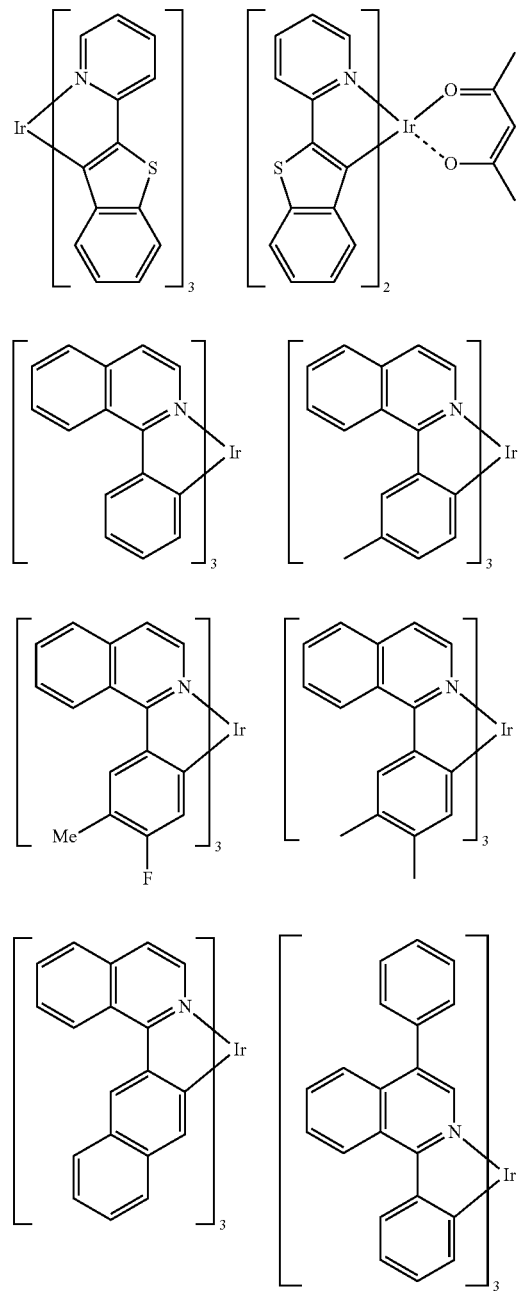

-continued
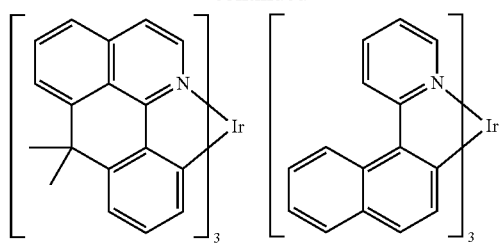
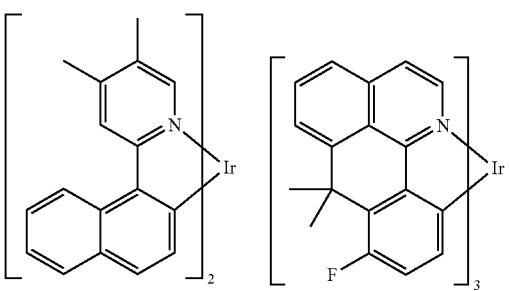
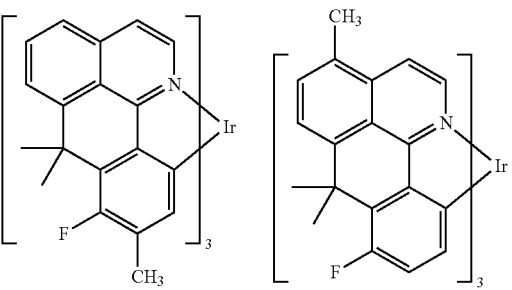
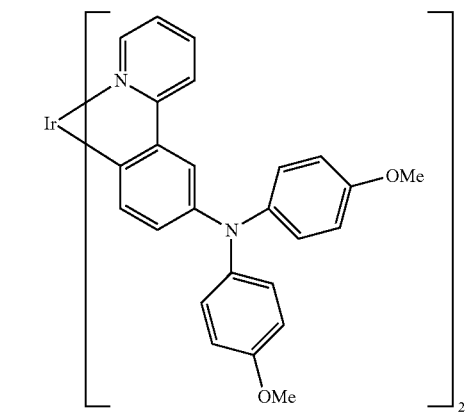
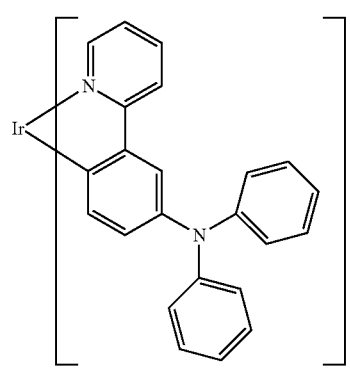
-continued
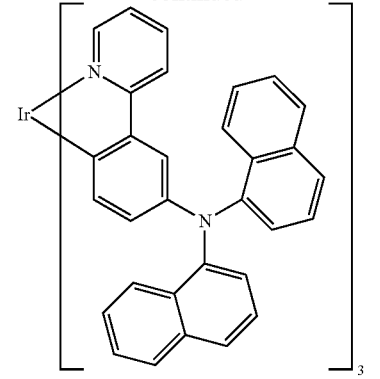
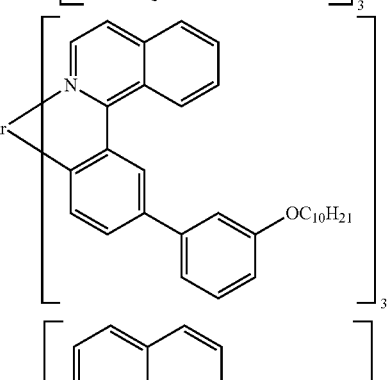
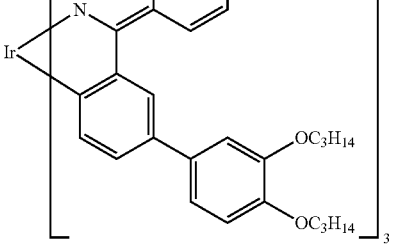
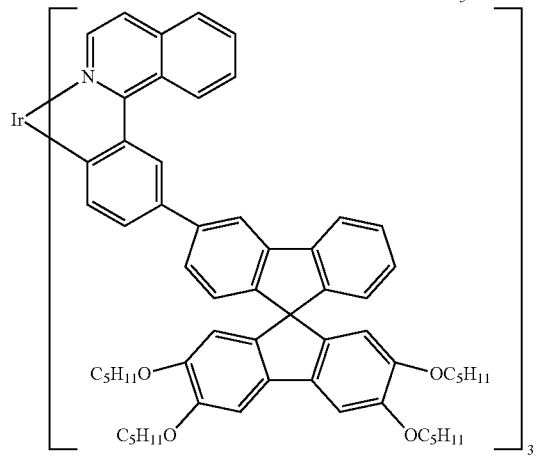
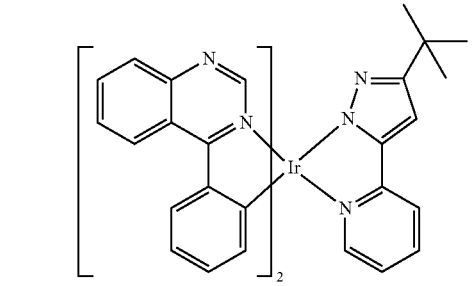

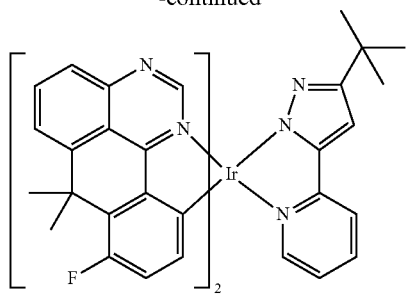
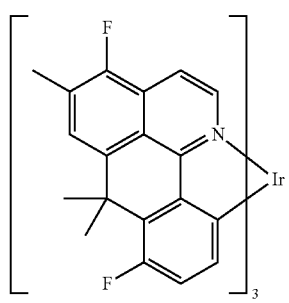
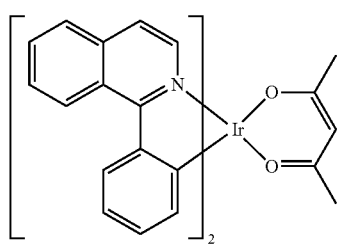
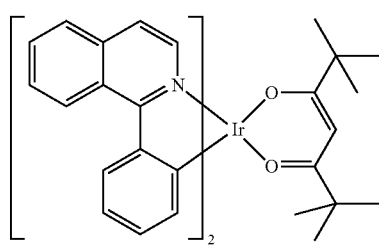
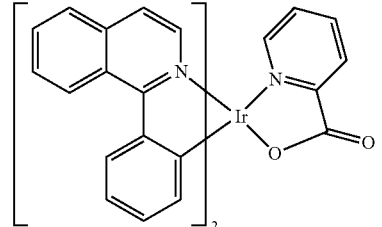
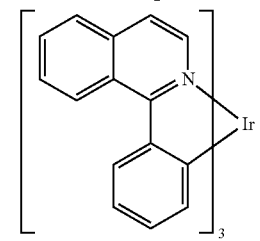
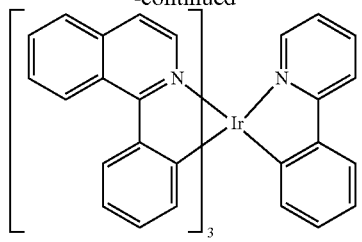
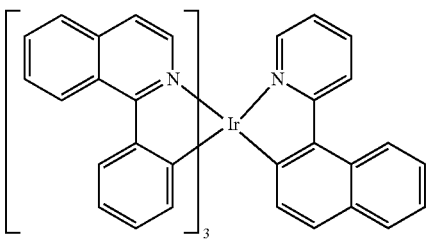
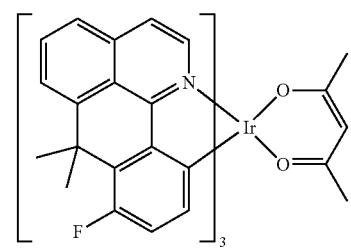
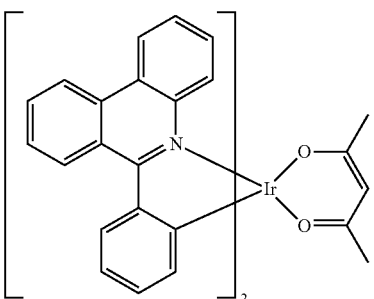
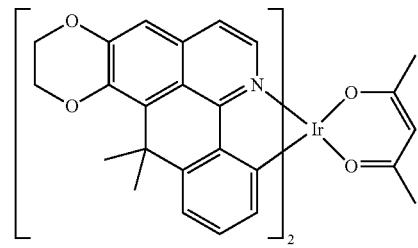
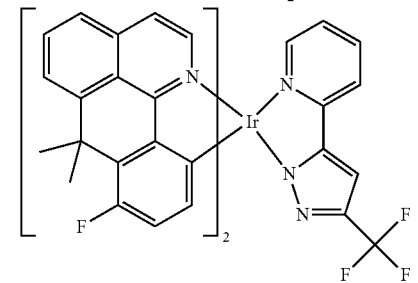

-continued
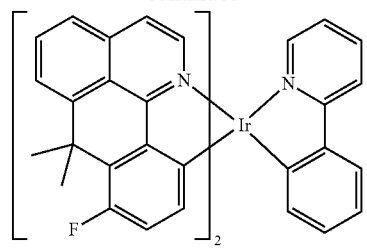
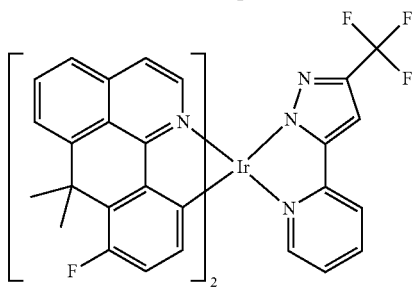
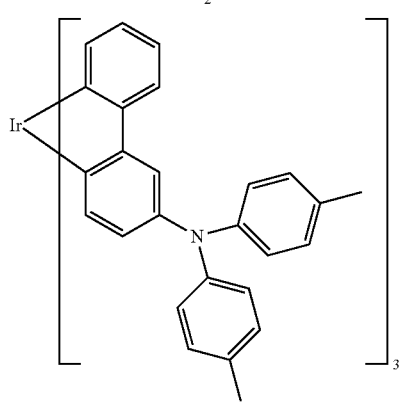
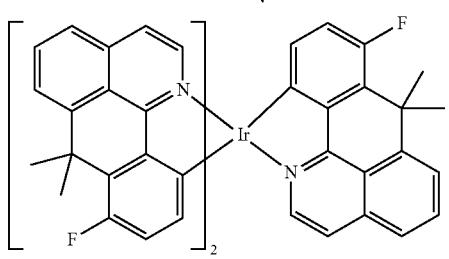
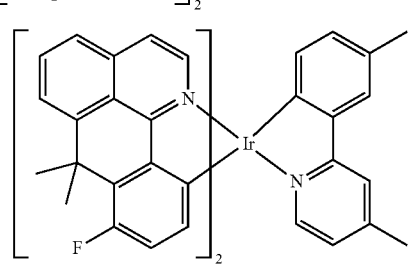
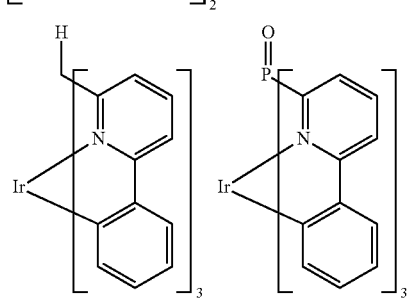
-continued
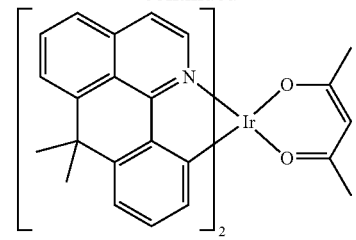
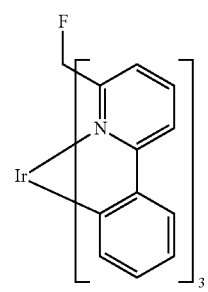
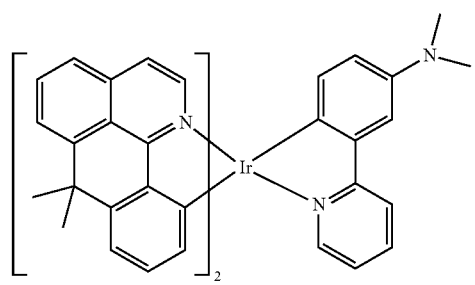
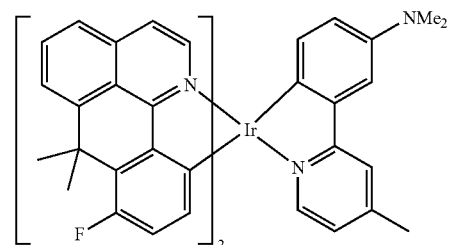
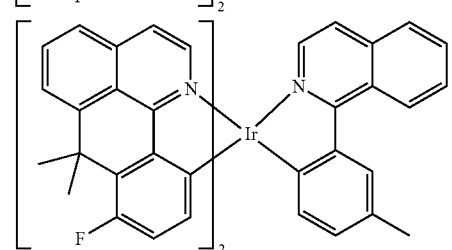
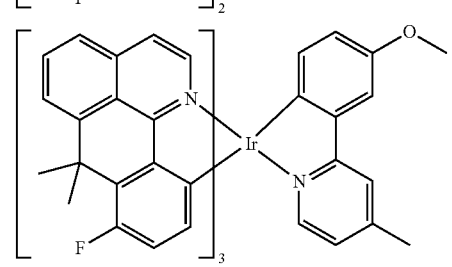

85
-continued
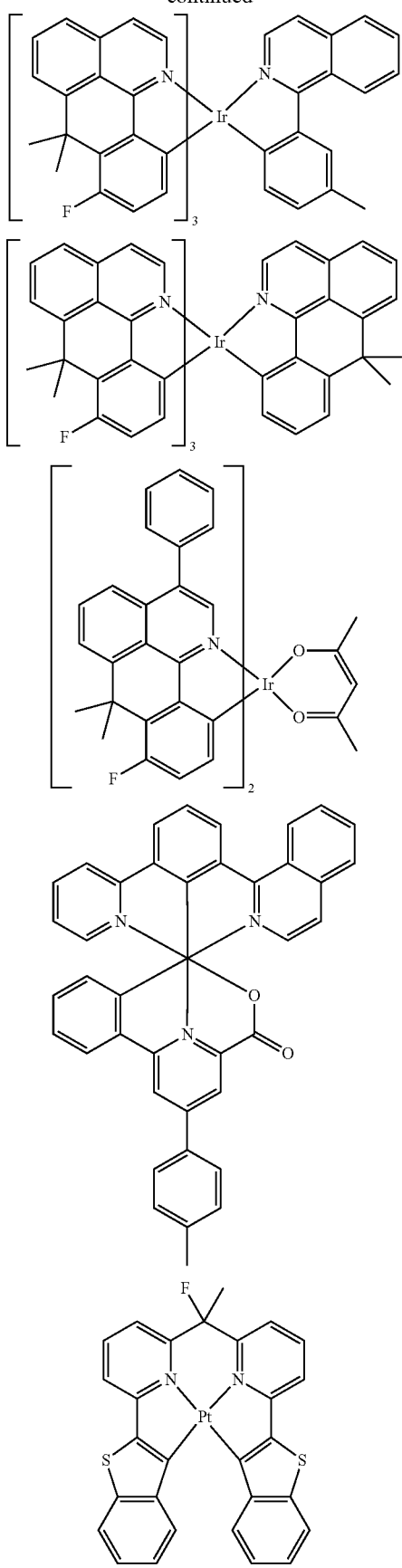
86
-continued
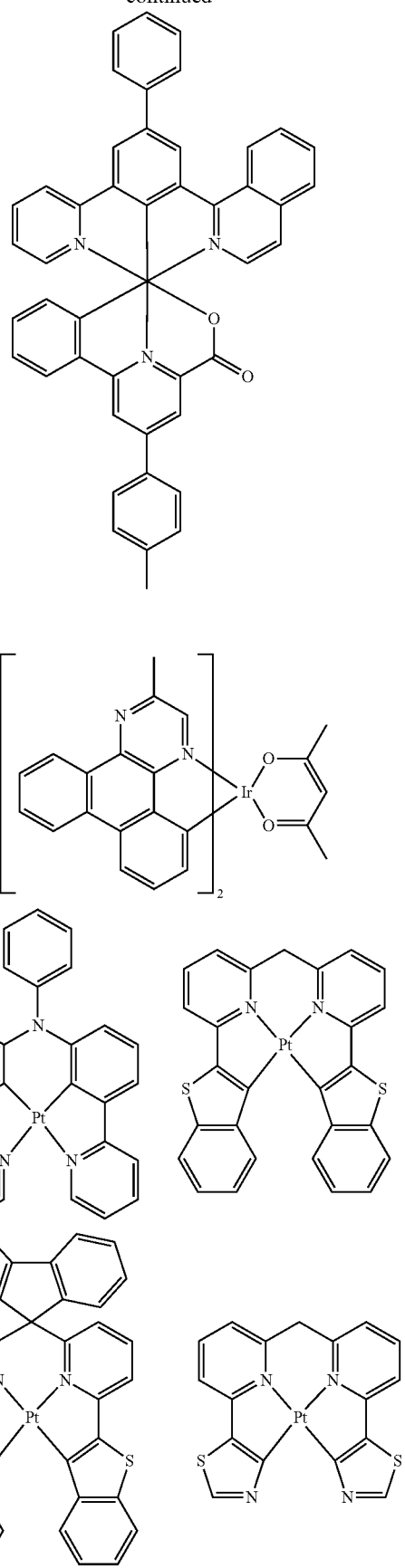

-continued

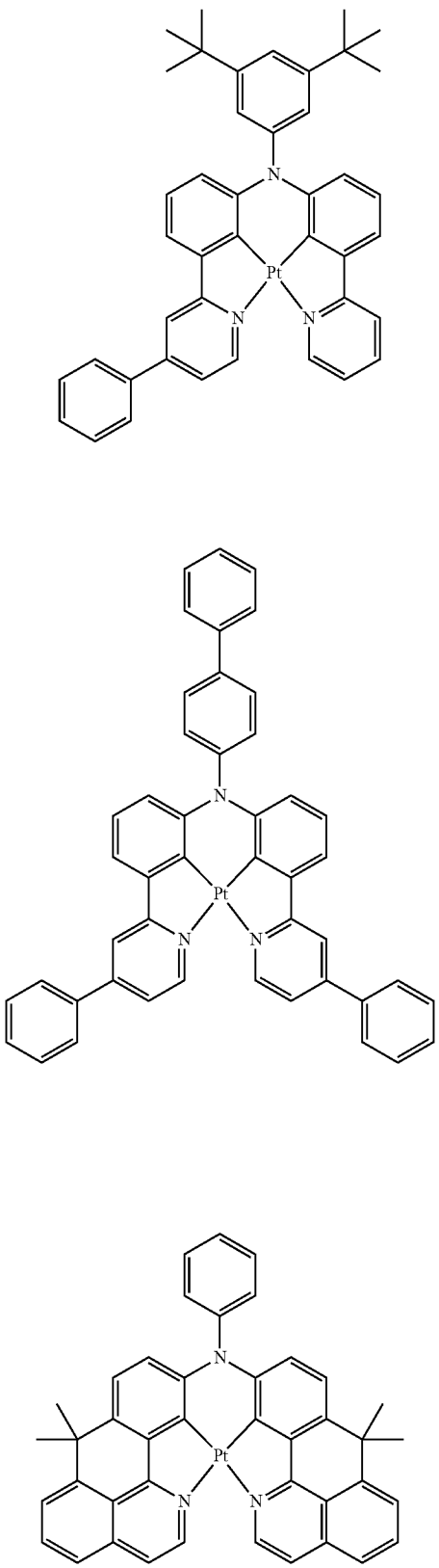
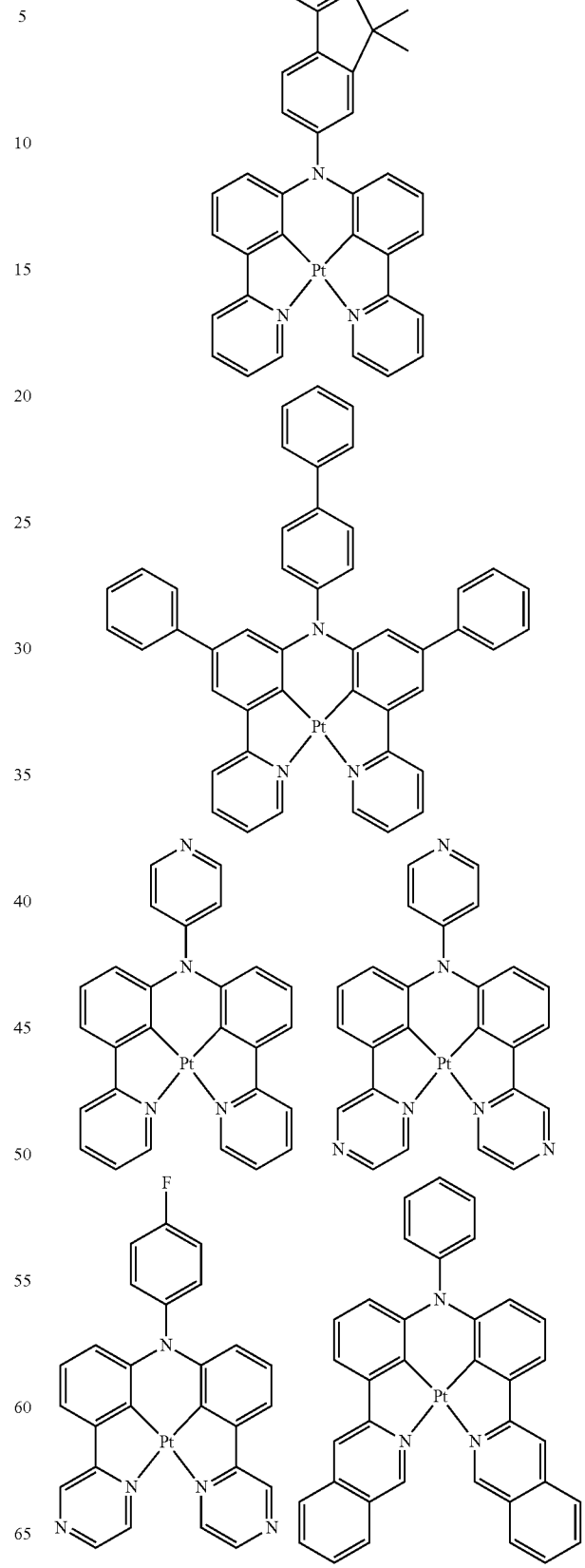

91
-continued
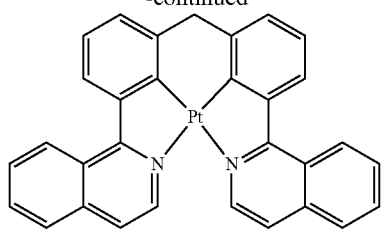
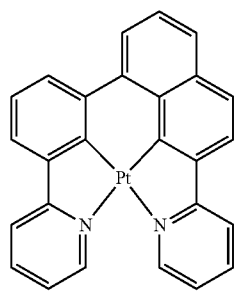
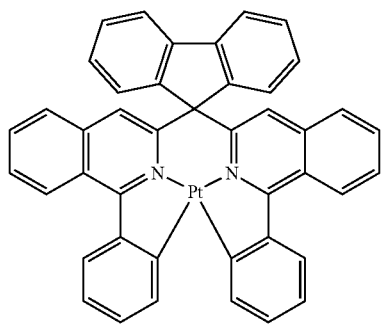
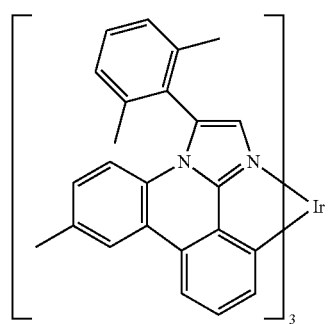
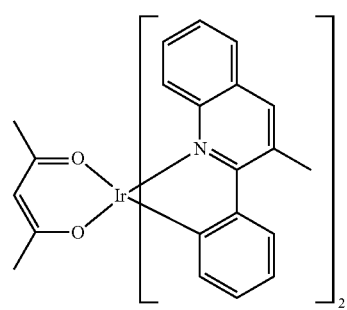
92
-continued
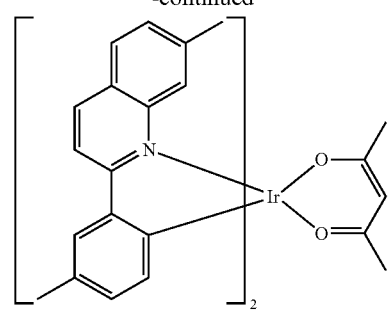
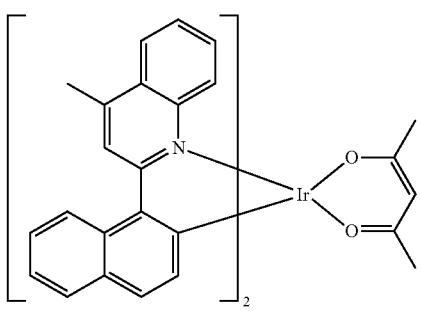
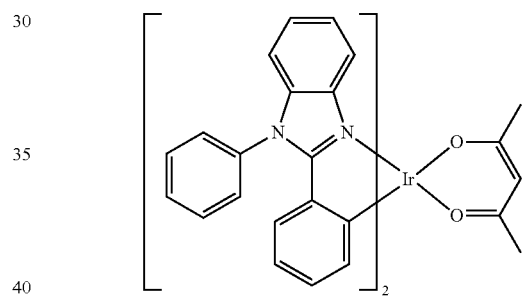
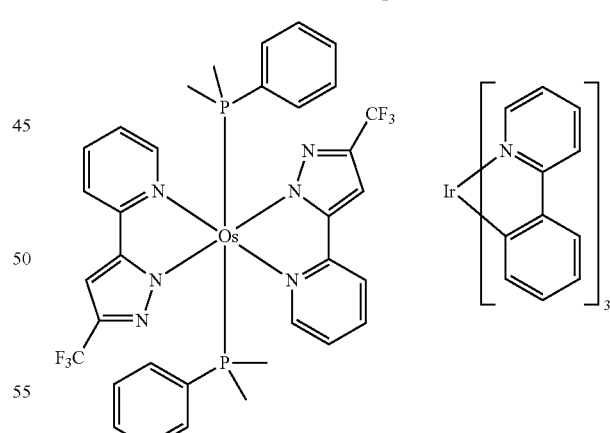
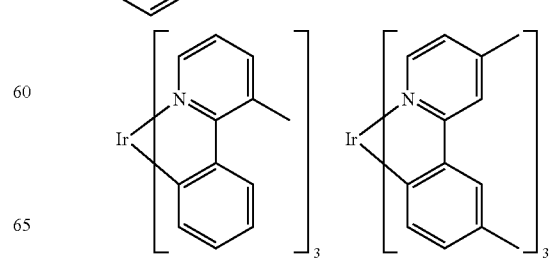

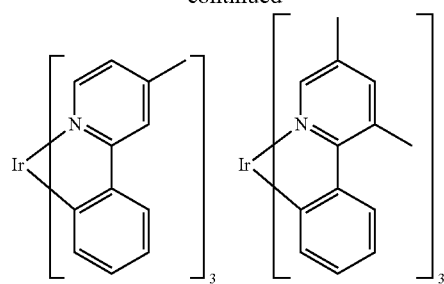
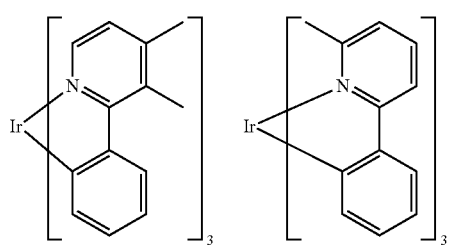
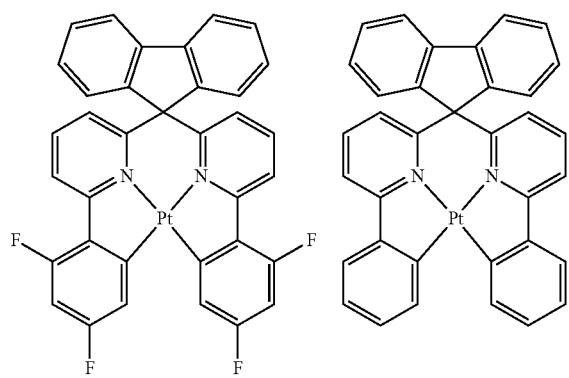
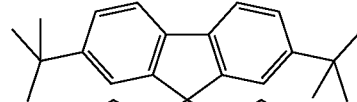
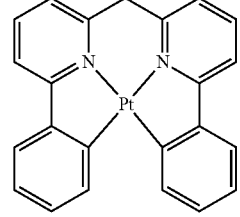
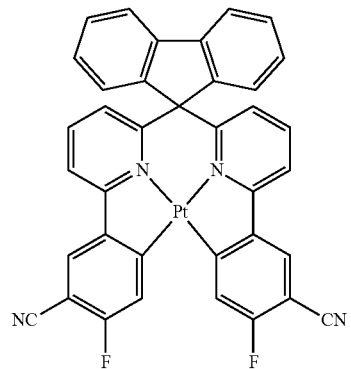
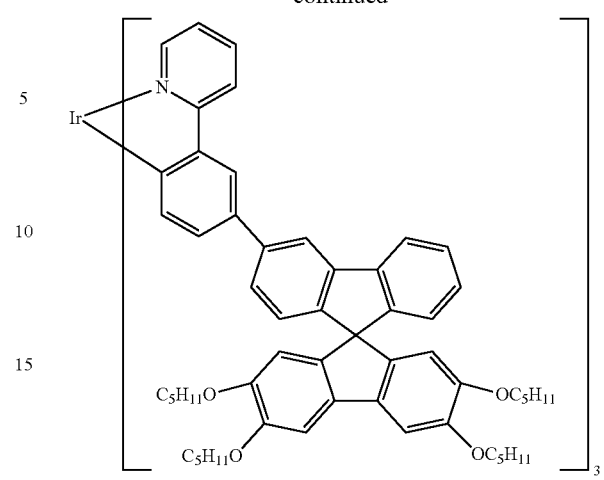
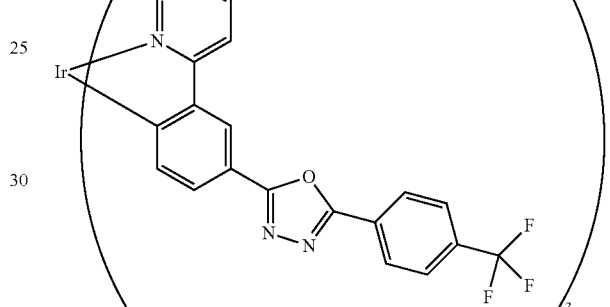
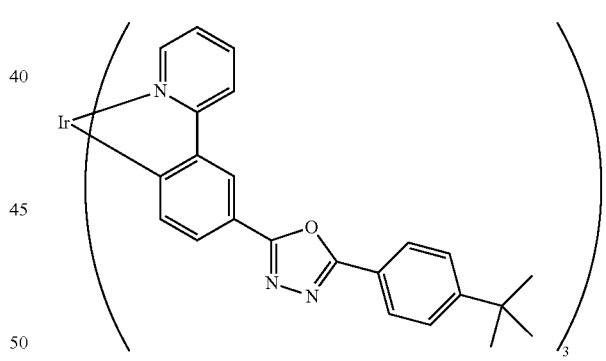
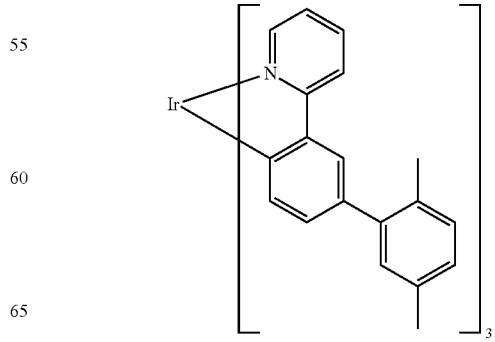

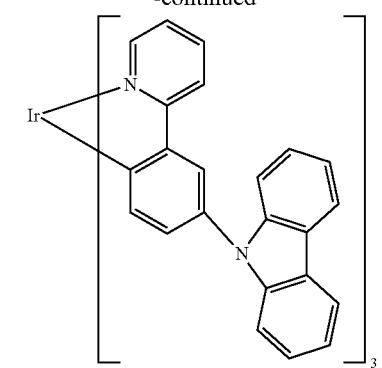
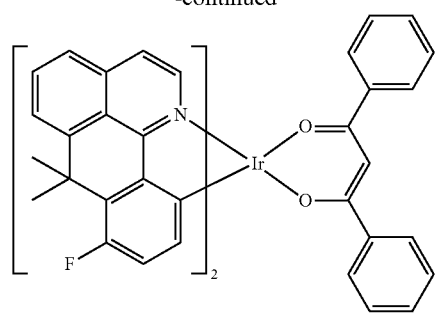
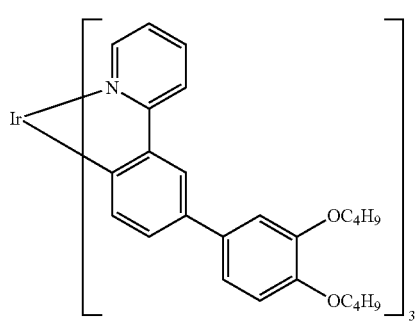
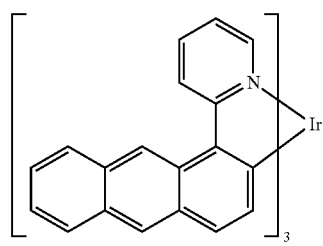
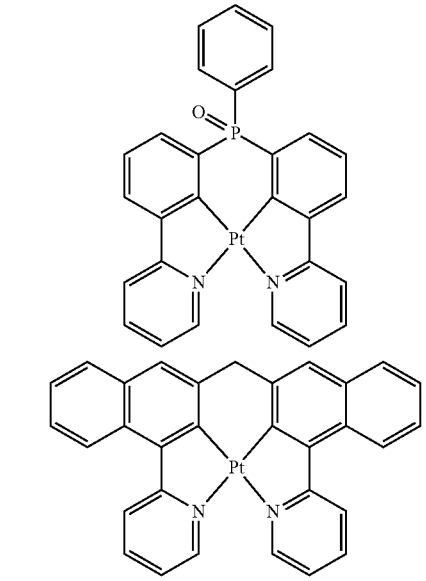
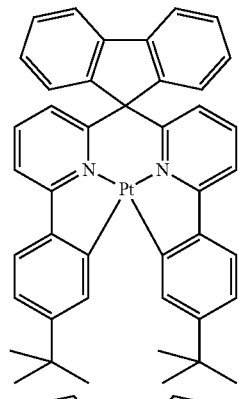
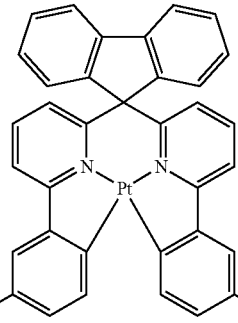
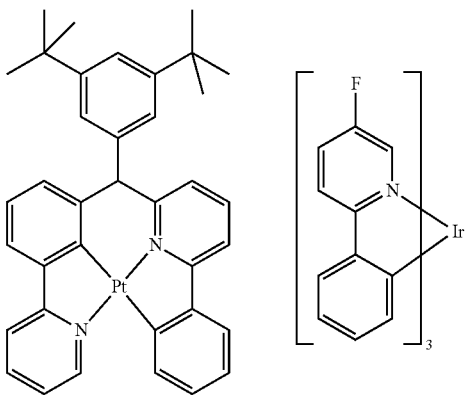
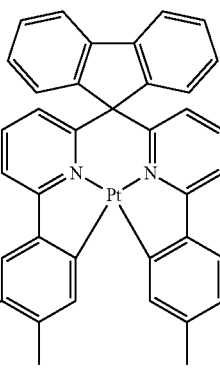
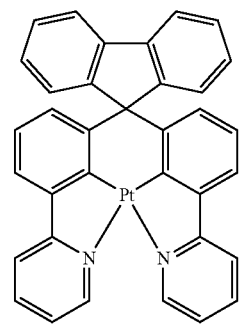

-continued
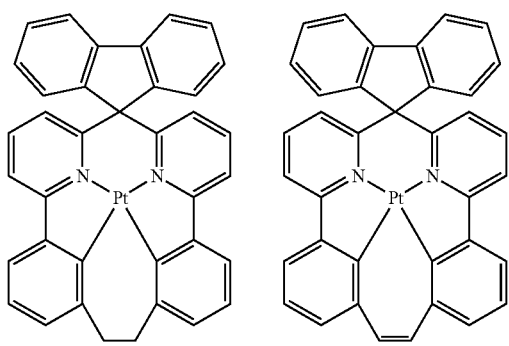
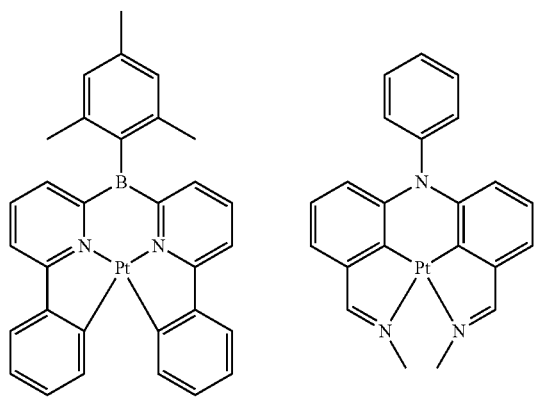
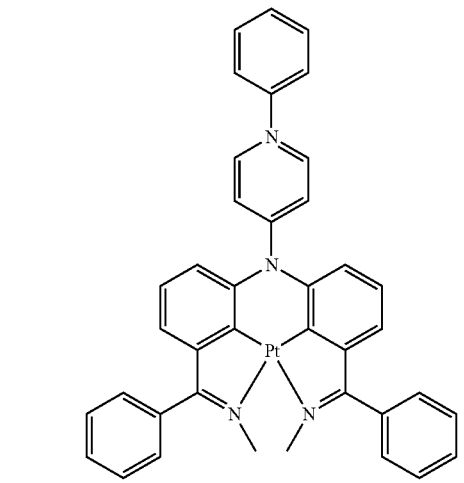
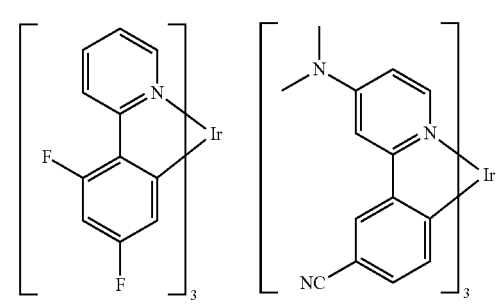
-continued
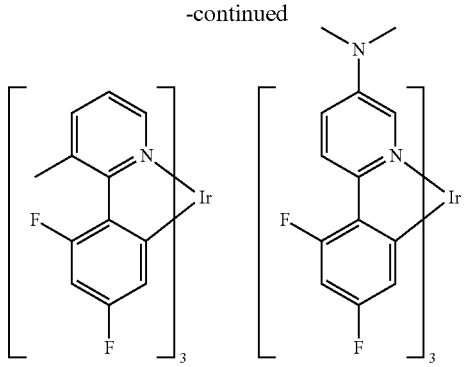
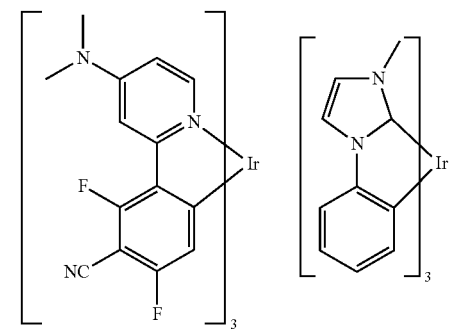
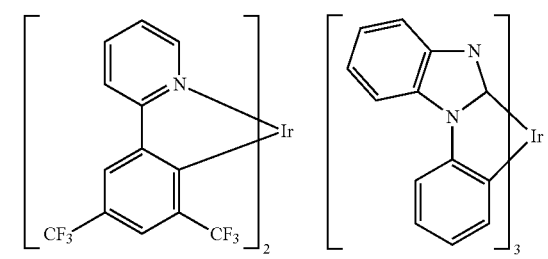
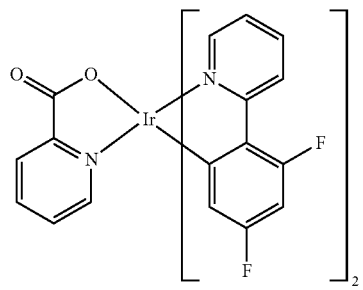
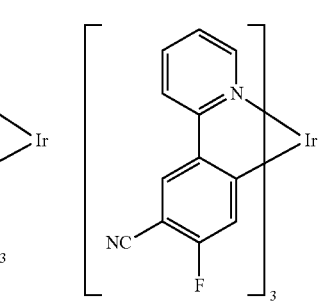

99
-continued
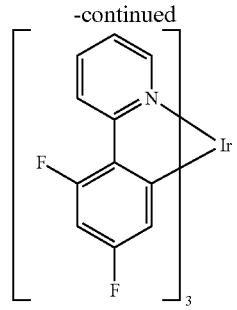
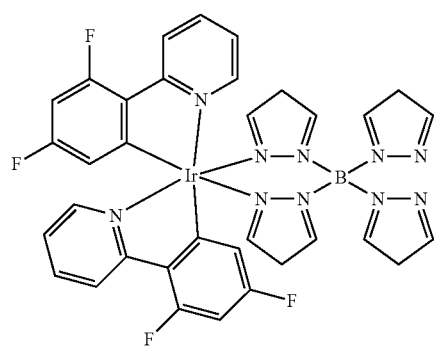
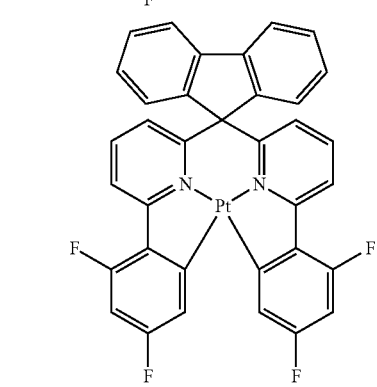
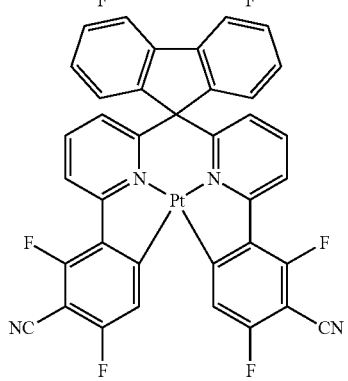
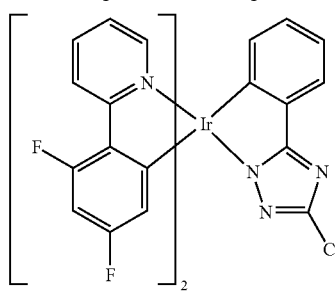
100
-continued
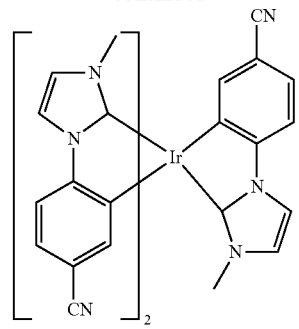
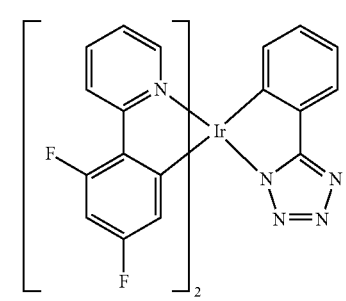
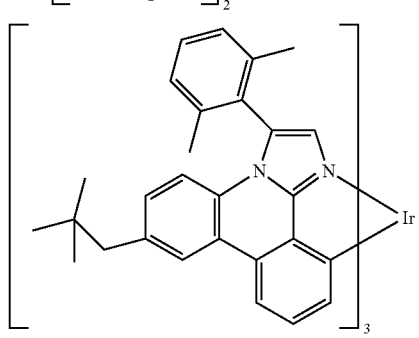
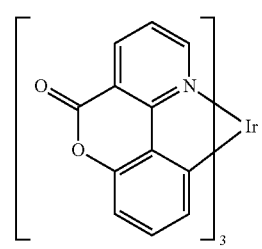
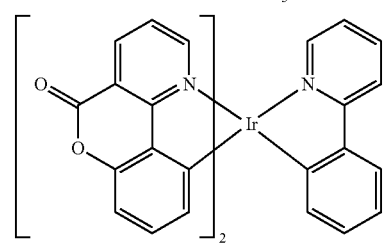
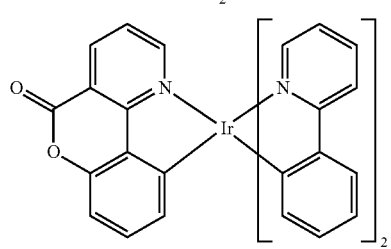

-continued

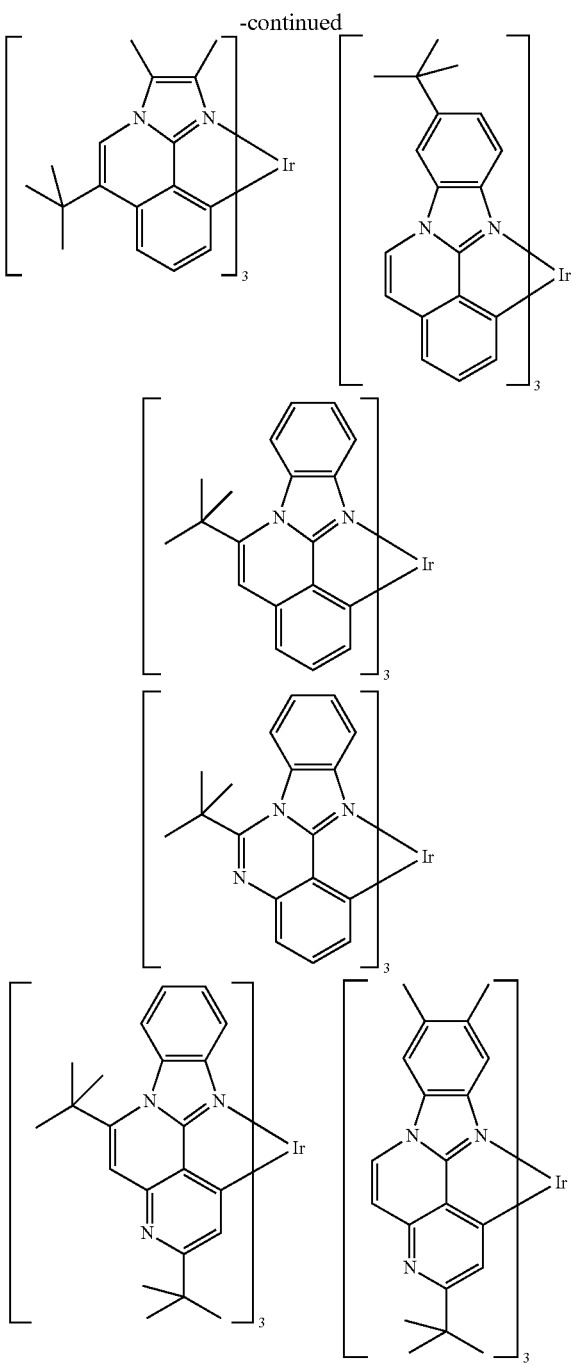

In a preferred embodiment of the invention, the compounds of the formula (1) or (167) are employed as hole-transport material. The compounds are then preferably employed in a hole-transport layer and/or in a hole-injection layer. A hole-injection layer in the sense of this invention is a layer which is directly adjacent to the anode. A hole-transport layer in the sense of this invention is a layer which is located between the hole-injection layer and the emission layer. The hole-transport layer may be directly adjacent to the emission layer. If the compounds of the formula (1) are used as hole-transport material or as hole-injection material, it may be preferred for them to be doped with electron-acceptor compounds, for example with $F_4$-TCNQ or compounds as described in EP 1476881 or EP 1596445. In a further preferred embodiment of the invention, a compound of the formula (1) is used as hole-transport material in combination with a hexaazatriphenylene derivative, as described in US 2007/0092755. The hexaazatriphenylene derivative here is particularly preferably employed in a separate layer.

If the compounds of the formula (1) or (167) are employed as hole-transport material in a hole-transport layer, the compound may be employed as pure material, i.e. in a proportion of 100%, in the hole-transport layer, or it may be employed in combination with one or more further compounds in the hole-transport layer.

In a further embodiment of the present invention, the compounds of the formula (1) or (167) are employed as emitting materials. For this purpose, the compounds are preferably employed in an emission layer. Besides at least one of the compounds of the formula (1) or (167), the emission layer furthermore comprises at least one host material. The person skilled in the art will be able to make a selection from the known host materials without difficulties and without being inventive.

In a further embodiment of the present invention, the compounds of the formula (1) or (167) are employed as matrix material in combination with one or more dopants, preferably phosphorescent dopants.

A dopant in a system comprising a matrix material and a dopant is taken to mean the component whose proportion in the mixture is the smaller. Correspondingly, a matrix material is taken to mean the component whose proportion in the mixture is the greater in a system comprising a matrix material and a dopant.

The proportion of the matrix material in the emitting layer is in this case between 50.0 and 99.9% by vol., preferably between 80.0 and 99.5% by vol. and particularly preferably between 92.0 and 99.5% by vol. for fluorescent emitting layers and between 85.0 and 97.0% by vol. for phosphorescent emitting layers.

Correspondingly, the proportion of the dopant is between 0.1 and 50.0% by vol., preferably between 0.5 and 20.0% by vol. and particularly preferably between 0.5 and 8.0% by vol. for fluorescent emitting layers and between 3.0 and 15.0% by vol. for phosphorescent emitting layers.

An emitting layer of an organic electroluminescent device may also comprise systems comprising a plurality of matrix materials (mixed-matrix systems) and/or a plurality of dopants. In this case too, the dopants are generally the materials whose proportion in the system is the smaller and the matrix materials are the materials whose proportion in the system is the greater. In individual cases, however, the proportion of an individual matrix material in the system may be smaller than the proportion of an individual dopant.

In a further preferred embodiment of the invention, the compounds of the formulae (1) or (167) are used as a component of mixed-matrix systems. The mixed-matrix systems preferably comprise two or three different matrix materials, particularly preferably two different matrix materials. One of the two materials here is preferably a material having hole-transporting properties and the other material is a material having electron-transporting properties. However, the desired electron-transporting and hole-transporting properties of the mixed-matrix components may also be combined principally or completely in a single mixed-matrix components, where the further mixed-matrix component(s) fulfil other functions. The two different matrix materials here may be present in a ratio of 1:50 to 1:1, preferably 1:20 to 1:1, particularly preferably 1:10 to 1:1 and very particularly preferably 1:4 to 1:1. Mixed-matrix systems are preferably employed in phosphorescent organic electroluminescent devices. More precise information on mixed-matrix systems is given, inter alia, in the application WO 2010/108579.

The mixed-matrix systems may comprise one or more dopants, preferably one or more phosphorescent dopants. In general, mixed-matrix systems are preferably employed in phosphorescent organic electroluminescent devices.

Particularly suitable matrix materials which can be used as matrix components of a mixed-matrix system in combination with the compounds according to the invention are selected from the preferred matrix materials for phosphorescent dopants indicated below or the preferred matrix materials for fluorescent dopants, depending on what type of dopant is employed in the mixed-matrix system.

Preferred phosphorescent dopants for use in mixed-matrix systems are the phosphorescent dopants shown in the above table.

The materials preferably employed in the relevant functions in the devices according to the invention are indicated below.

Preferred fluorescent dopants are selected from the class of the arylamines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position.

Suitable matrix materials, preferably for fluorescent dopants, besides the compounds according to the invention, are materials from various classes of substance. Preferred matrix materials are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 20051084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Preferred matrix materials for phosphorescent dopants, besides the compounds according to the invention, are aromatic amines, in particular triarylamines, for example in accordance with US 2005/0069729, carbazole derivatives (for example CBP, N,N-biscarbazolylbiphenyl) or compounds in accordance with WO 2005/039246, US 2005/0069729, JP 2004/288381, EP 1205527 or WO 2008/086851, bridged carbazole derivatives, for example in accordance with WO 2011/088877 and WO 2011/128017, indenocarbazole derivatives, for example in accordance with WO 2010/136109 and WO 2011/000455, azacarbazole derivatives, for example in accordance with EP 1617710, EP 1617711, EP 1731584, JP 2005/347160, indolocarbazole derivatives, for example in accordance with WO 2007/063754 or WO 2008/056746, ketones, for example in accordance with WO 2004/093207 or WO 2010/006680, phosphine oxides, sulfoxides and sulfones, for example in accordance with WO 2005/003253, oligophenylenes, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, aluminium complexes, for example BAlq, diazasilole and tetraazasilole derivatives, for example in accordance with WO 2010/054729, diazaphosphole derivatives, for example in accordance with WO 2010/054730, and aluminium complexes, for example BAlq.

Suitable charge-transport materials, as can be used in the hole-injection or hole-transport layer or in the electron-transport layer of the organic electro-luminescent device according to the invention, are, for example, the compounds disclosed in Y. Shirota et al., *Chem. Rev.* 2007, 107(4), 953-1010, or other materials as are employed in these layers in accordance with the prior art.

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ag/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/NiO$_x$, Al/PtO$_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO).

Preference is furthermore given to conductive, doped organic materials, in particular conductive, doped polymers.

The device is appropriately (depending on the application) structured, provided with contacts and finally sealed, since the lifetime of the devices according to the invention is shortened in the presence of water and/or air.

In a preferred embodiment, the organic electroluminescent device according to the invention is characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (1) are necessary for this purpose. High solubility can be achieved through suitable substitution of the compounds.

For the production of an organic electroluminescent device according to the invention, it is furthermore preferred to apply one or more layers from solution and one or more layers by a sublimation process.

In accordance with the invention, the electronic devices comprising one or more compounds of the formula (1) or (167) can be employed in displays, as light sources in lighting applications and as light sources in medical and/or cosmetic applications (for example light therapy).

Devices comprising the compounds of the formula (1) or (167) can be employed in a very versatile manner. Thus, for example, electroluminescent devices comprising one or more compounds of the formula (1) or (167) can be employed in displays for televisions, mobile telephones, computers and cameras. However, the devices can also be used in lighting applications. Furthermore, electroluminescent devices, for example in OLEDs or OLECs, comprising at least one of the compounds of the formula (1) or (167) can be used for phototherapy in medicine or cosmetics. Thus, a large number of diseases (psoriasis, atopic dermatitis, inflammation, acne, skin cancer, etc.) can be treated or skin wrinkling, skin reddening and skin ageing can be prevented or reduced. Furthermore, the light-emitting devices can be utilised in order to keep drinks, meals or foods fresh or in order to sterilise equipment (for example medical equipment).

The compounds according to the invention and the organic electroluminescent devices according to the invention are distinguished by the following surprising advantages over the prior art:

1. The compounds according to the invention are very highly suitable for use in a hole-transport layer or a hole-injection layer in electronic devices, such as, for example, in organic electroluminescent devices, in particular owing to their high hole mobility.
2. The compounds according to the invention have a relatively low sublimation temperature, high temperature stability and high oxidation stability and a high glass-transition temperature, which is advantageous both for the processability, for example from solution or from the gas phase, and also for use in electronic devices.
3. The use of the compounds according to the invention in electronic devices, in particular employed as hole-transport or hole-injection material, results in high efficiencies, low operating voltages and long lifetimes.

It should be pointed out that variations of the embodiments described in the present invention fall within the scope of this invention. Each feature disclosed in the present invention can, unless explicitly excluded, be replaced by alternative features which serve the same, an equivalent or a similar purpose. Thus, each feature disclosed in the present invention is, unless stated otherwise, to be regarded as an example of a generic series or as an equivalent or similar feature.

All features of the present invention can be combined with one another in any way, unless certain features and/or steps are mutually exclusive. This applies in particular to preferred features of the present invention. Equally, features of non-essential combinations can be used separately (and not in combination).

It should furthermore be pointed out that many of the features, and in particular those of the preferred embodiments of the present invention, are themselves inventive and should not merely be regarded as part of the embodiments of the present invention. For these features, independent protection may be sought in addition or as an alternative to each invention currently claimed.

The teaching on technical action disclosed with the present invention can be abstracted and combined with other examples.

The invention is explained in greater detail by the following examples, without wishing to restrict it thereby.

EXAMPLES

Materials

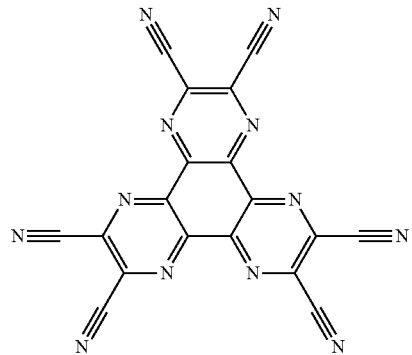

HIL1

-continued
HIL2
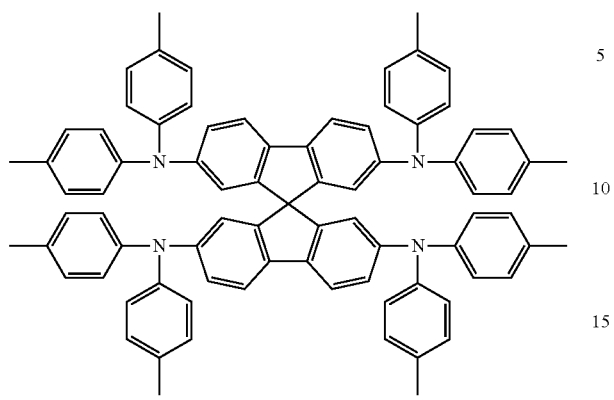
H2
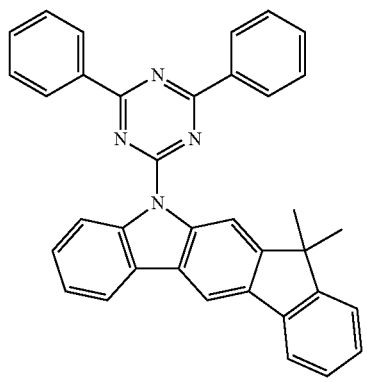
H1
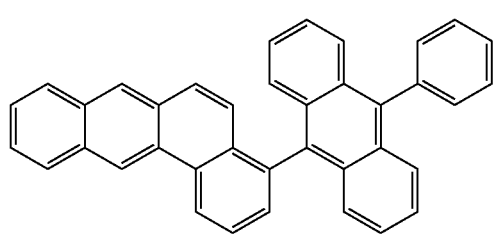
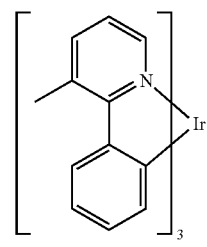
Irpy
ETM1
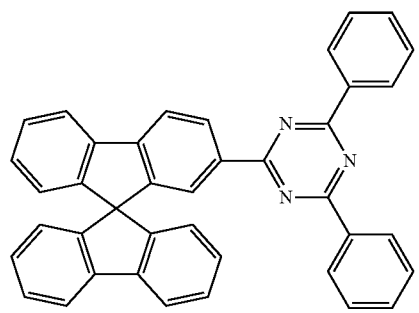
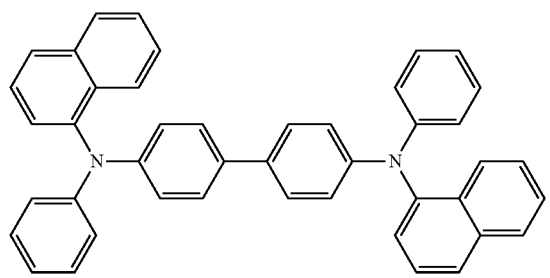
NPB
SEB1
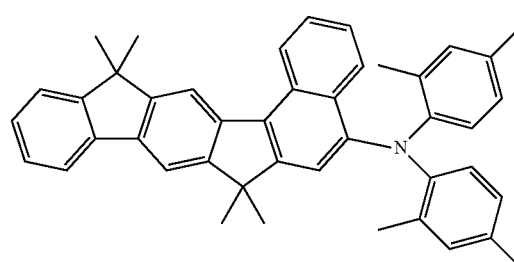
HTMV1
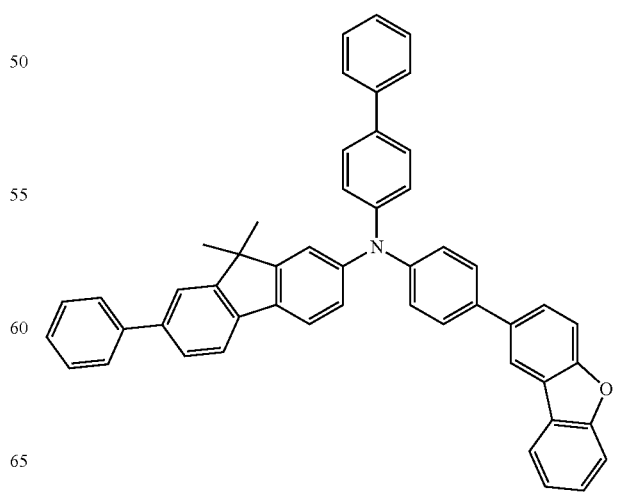
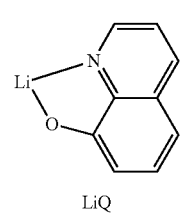
LiQ 109
-continued
HTMV2
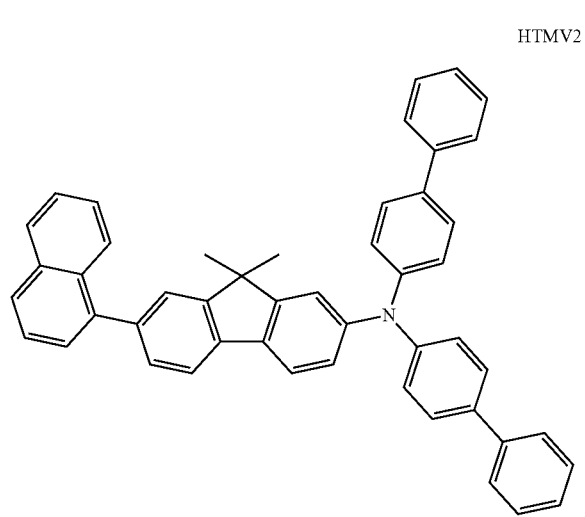
HTMV3
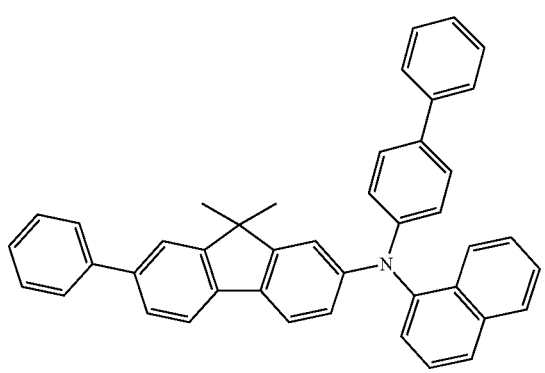
HTMV4
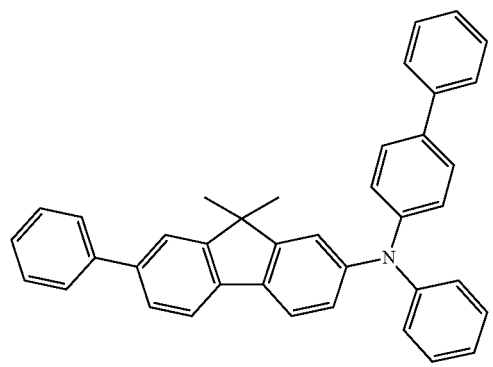
110
-continued
HTMV5
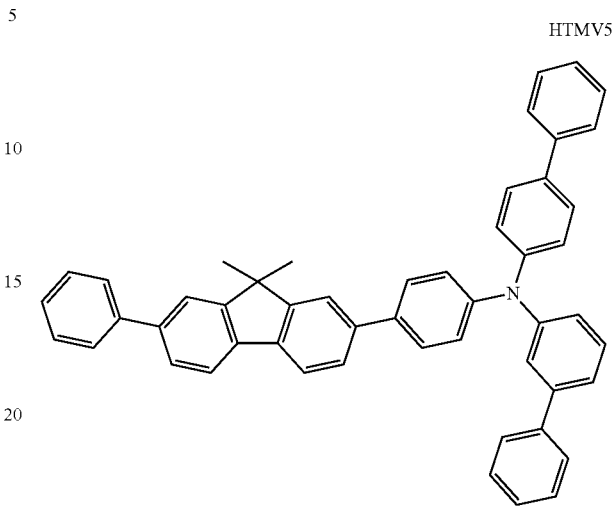
HTMV6
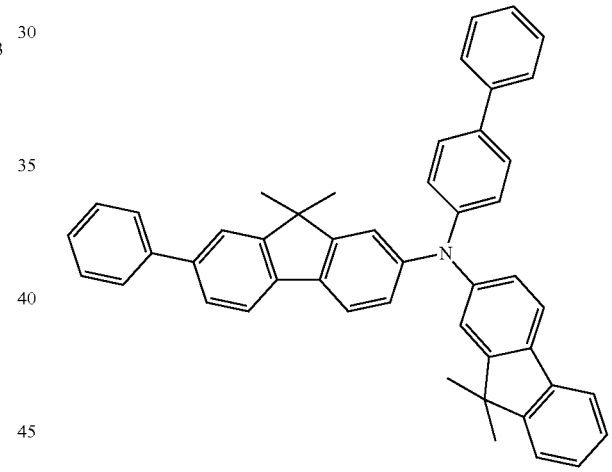
(303)

-continued

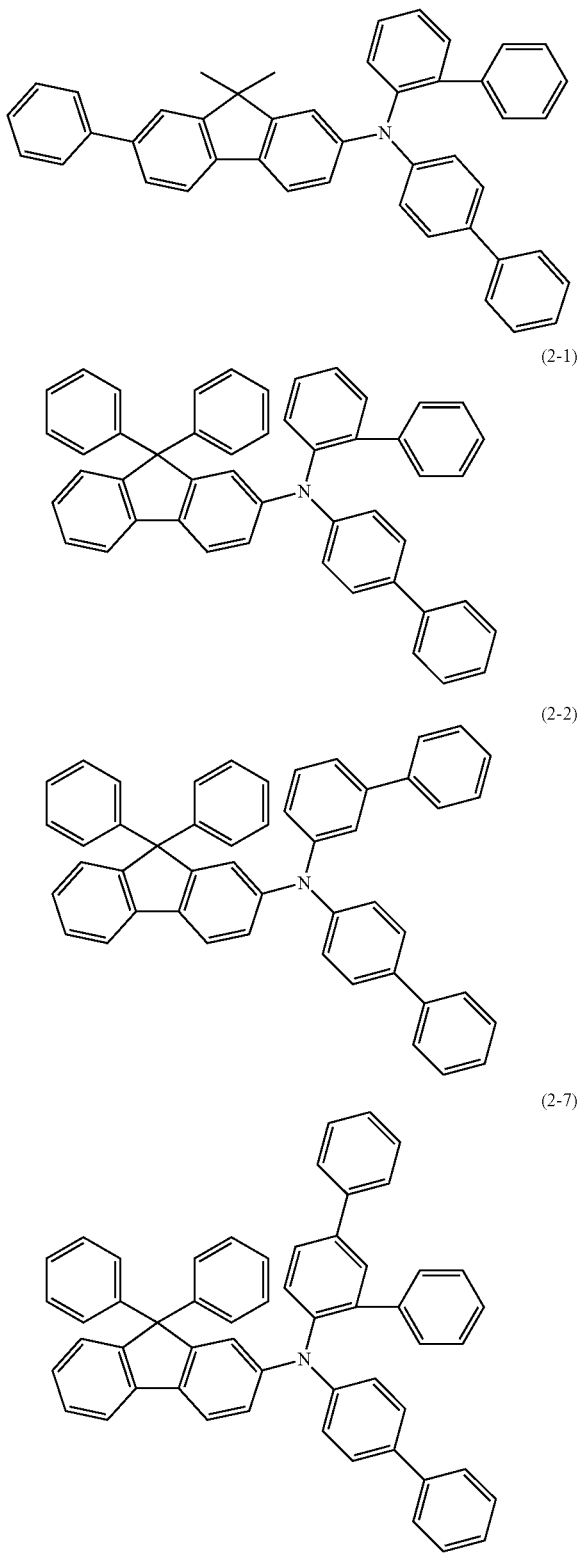

Materials HIL1, HIL2 (EP 0676461), H1 (WO 2008/145239), ETM1 (WO 2005/053055), SEB1 (WO 2008/006449), LiQ and NPB are well known to the person skilled in the art. Their properties and syntheses are known from the prior art. Compounds (3-3), (3-1), (2-1) and (2-2) and (2-7) are in accordance with the invention.

Example 1

Synthesis of the compound biphenyl-2-ylbiphenyl-4-yl-(9,9-dimethyl-9H-fluoren-2-yl)amine (1-1) and Compounds (1-2) to (1-5)

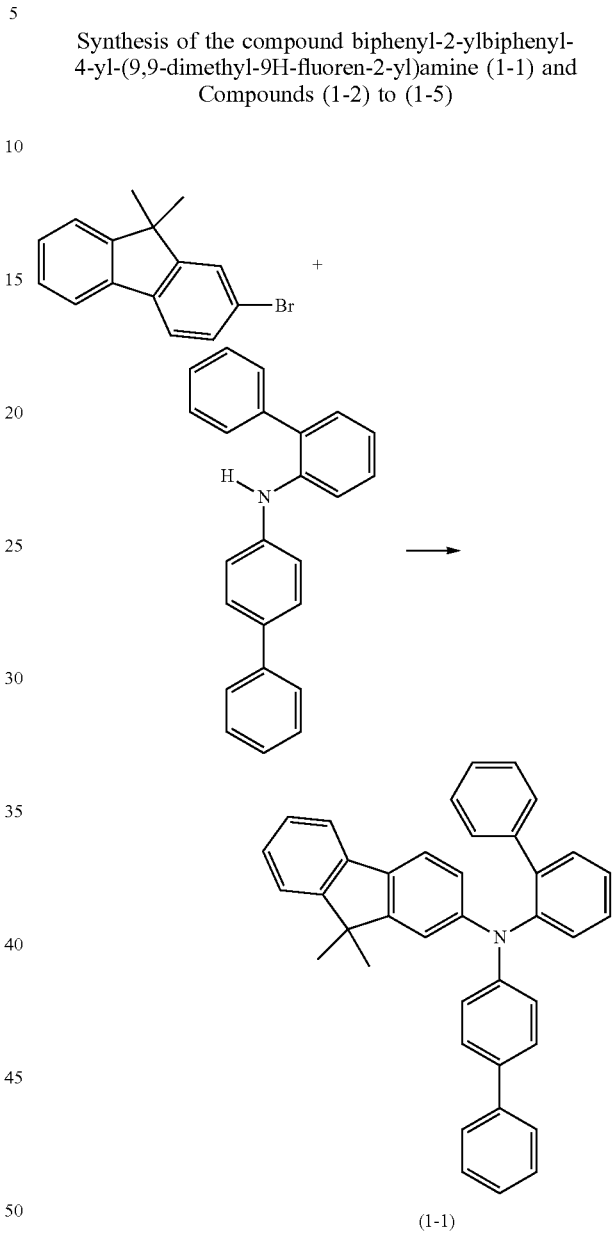

23.5 g of biphenyl-2-ylbiphenyl-4-ylamine (73 mmol) and 20.0 g of 2-bromofluorene (73 mmol) are dissolved in 500 ml of toluene: the solution is degassed and saturated with $N_2$. 2.52 g (2.93 mmol) of tri-tert-butylphosphine and 0.33 g (1.46 mmol) of palladium(II) acetate are then added. 10.8 g of sodium tert-butoxide (110 mmol) are subsequently added. The reaction mixture is heated at the boil for 6 h under a protective atmosphere. The mixture is subsequently partitioned between toluene and water, and the organic phase is washed three times with water, dried over $Na_2SO_4$ and evaporated in a rotary evaporator. After the crude product has been filtered through silica gel with toluene, the residue which remains is recrystallised from heptane/toluene and finally sublimed in a high vacuum. The purity is 99.9%. The yield is 32.0 g (85% of theory).

The following compounds (1-2) to (1-5) are prepared analogously:
| Starting material 1 | Starting material 2 | Product | Yield |
|---|---|---|---|
| 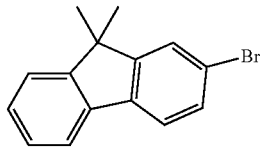 [SMILES: CC1(C)c2ccccc2-c2ccc(Br)cc21] | 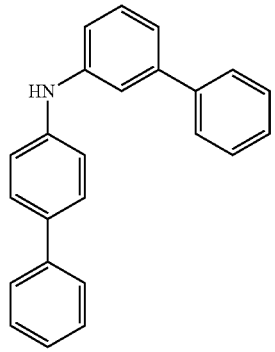 [SMILES: c1ccc(-c2ccc(Nc3cccc(-c4ccccc4)c3)cc2)cc1] | 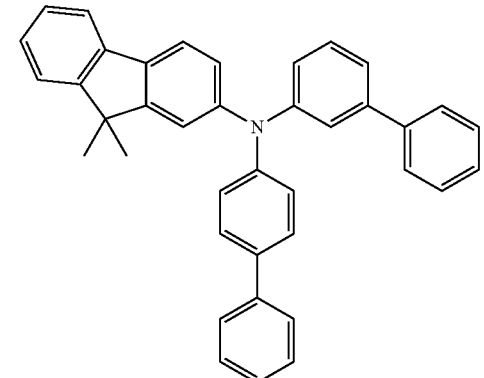<br>(1-2) | 78% |
| 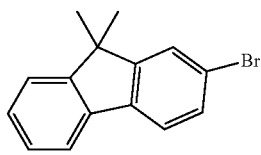 [SMILES: CC1(C)c2ccccc2-c2ccc(Br)cc21] | 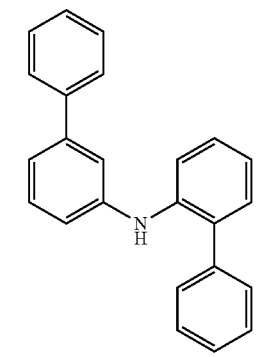 [SMILES: c1ccc(-c2cccc(Nc3ccccc3-c3ccccc3)c2)cc1] | 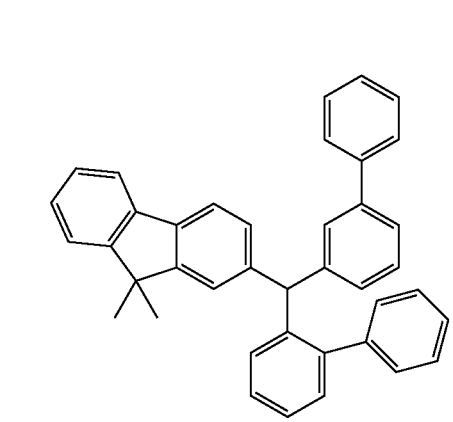<br>(1-3) | 92% |
| 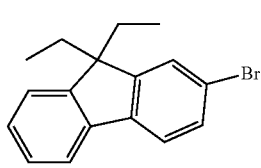 [SMILES: CCC1(CC)c2ccccc2-c2ccc(Br)cc21] | 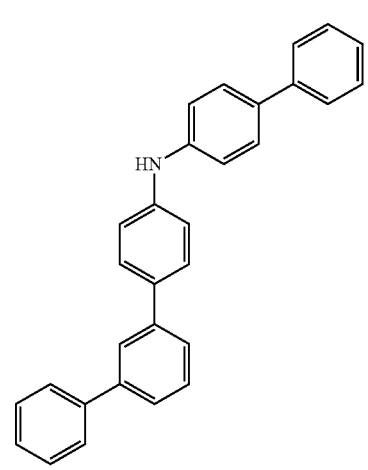 [SMILES: c1ccc(-c2ccc(Nc3ccc(-c4cccc(-c5ccccc5)c4)cc3)cc2)cc1] | 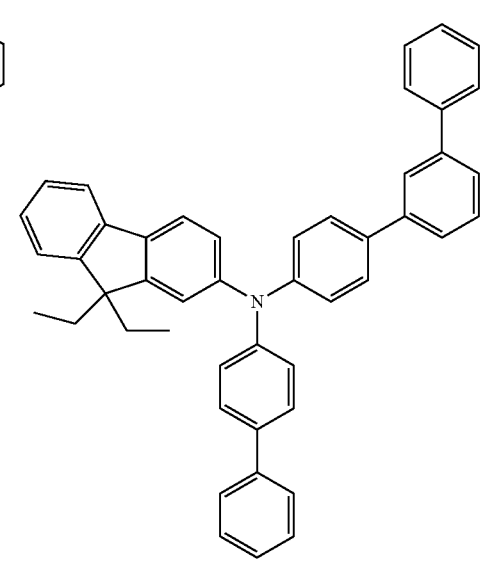<br>(1-4) | 88% |

-continued

| Starting material 1 | Starting material 2 | Product | Yield |
|---|---|---|---|
| | | | 77% |
| | | (1-5) | |

Example 2

Synthesis of the Compound biphenyl-2-ylbiphenyl-4-yl-(9,9-diphenyl-9H-fluoren-3-yl)amine (2-1) and Compounds (2-2) to (2-10)

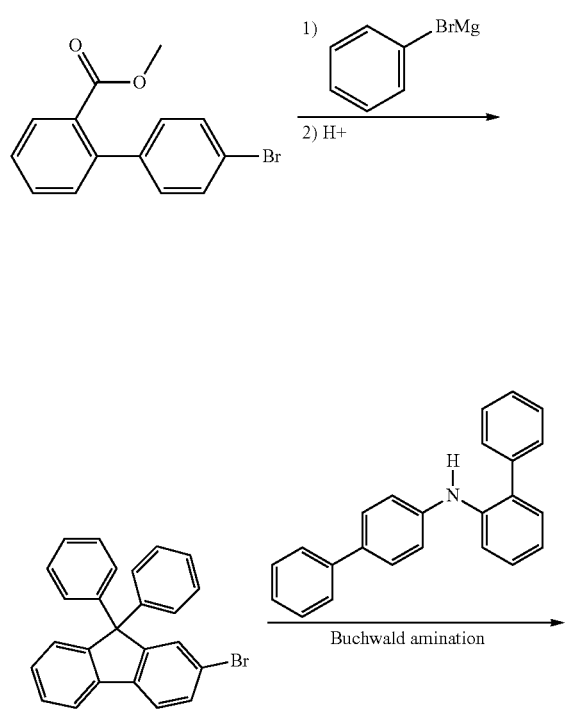

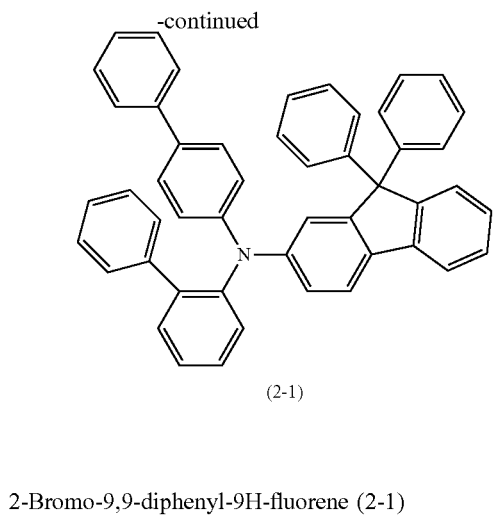

(2-1)

2-Bromo-9,9-diphenyl-9H-fluorene (2-1)

30 g (103 mmol) of methyl 4'-bromobiphenyl-2-carboxylate are dissolved in 500 ml of dried THF in a flask which has been dried by heating. The clear solution is cooled to −10° C., and 102 ml (307 mmol) of a freshly prepared 3 M 2-phenylmagnesium bromide solution are then added. The reaction mixture is slowly warmed to room temperature and then quenched using NH$_4$Cl (500 ml).

The mixture is subsequently partitioned between ethyl acetate and water, and the organic phase is washed three times with water, dried over Na$_2$SO$_4$ and evaporated in a rotary evaporator. 400 ml of acetic acid are carefully added to the residue. 80 ml of fuming HCl are subsequently added. The batch is heated to 75° C. and kept at this temperature for 5 h. A white solid precipitates out during this time. The batch is then cooled to room temperature, and the precipitated solid is filtered off with suction and rinsed with methanol. The residue is dried at 40° C. in vacuo. The yield is 29.4 g (74 mmol) (72% of theory).

The following brominated compounds are prepared analogously:

| Starting material 1 | Starting material 2 | Product | Yield |
|---|---|---|---|
| | | | 65% |
| | | | 70% |
| | | | 72% |
| | | | 80% |

Biphenyl-2-ylbiphenyl-4-yl-(9,9-diphenyl-9H-fluoren-3-yl)amine (2-1)

17 g of biphenyl-2-ylbiphenyl-4-ylamine (53 mmol) and 21 g of 2-bromo-9,9-diphenyl-9H-fluorene (53 mmol) are dissolved in 350 ml of toluene: the solution is degassed and saturated with $N_2$. 2.1 ml (2.1 mmol) of a 1 M solution of tri-tert-butylphosphine and 0.24 g (1.06 mmol) of palladium (II) acetate are then added, and 12.7 g of sodium tert-butoxide (132 mmol) are subsequently added. The reaction mixture is heated at the boil for 5 h under a protective atmosphere. The mixture is subsequently partitioned between toluene and water, and the organic phase is washed three times with water, dried over $Na_2SO_4$ and evaporated in a rotary evaporator. After the crude product has been filtered through silica gel with toluene, the residue which remains is recrystallised from heptane/toluene and finally sublimed in a high vacuum. The purity is 99.9%. The yield is 25 g (74% of theory).

The following compounds (2-2) to (2-10) can be prepared analogously.
| Starting material 1 | Starting material 2 | Product | Yield |
|---|---|---|---|
| 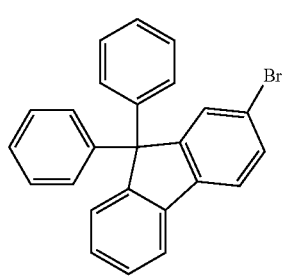 [SMILES: Brc1ccc2c(c1)C(c1ccccc1)(c1ccccc1)c1ccccc1-2] | 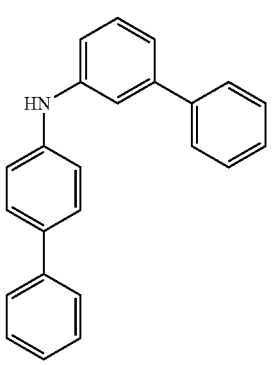 [SMILES: c1ccc(-c2ccc(Nc3cccc(-c4ccccc4)c3)cc2)cc1] | 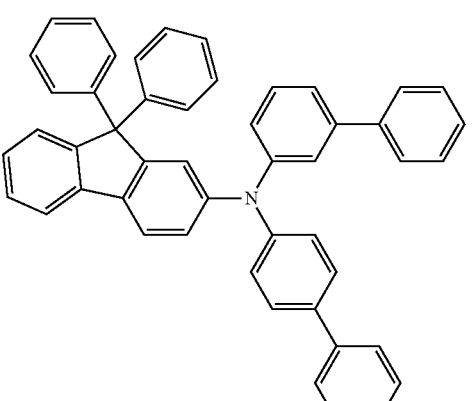<br>(2-2) | 72% |
| 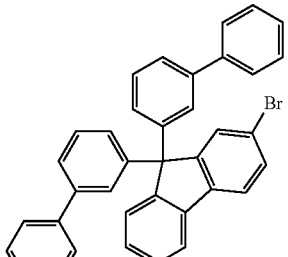 | 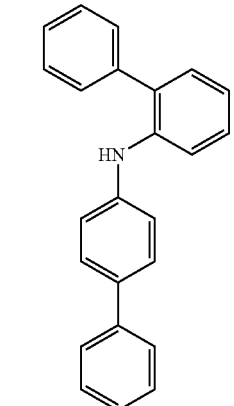 | 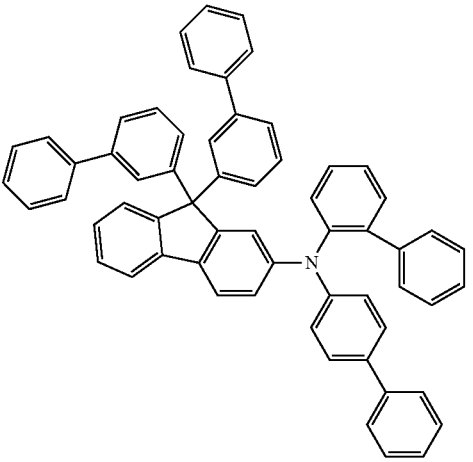<br>(2-3) | 78% |
| 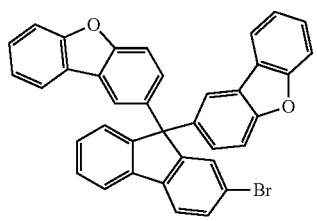 [SMILES: Brc1ccc2c(c1)C(c1ccc3oc4ccccc4c3c1)(c1ccc3oc4ccccc4c3c1)c1ccccc1-2] | 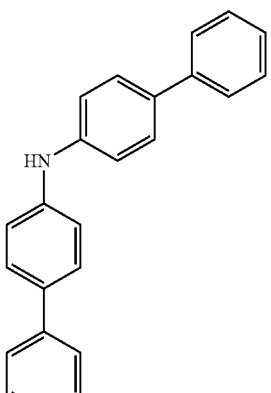 | 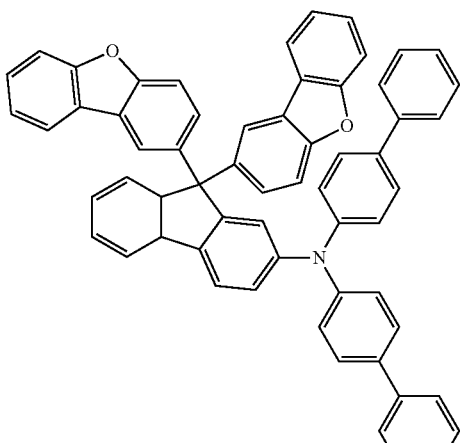<br>(2-4) | 81% |

-continued
| Starting material 1 | Starting material 2 | Product | Yield |
|---|---|---|---|
| | | | 75% |
| | | | 75% |
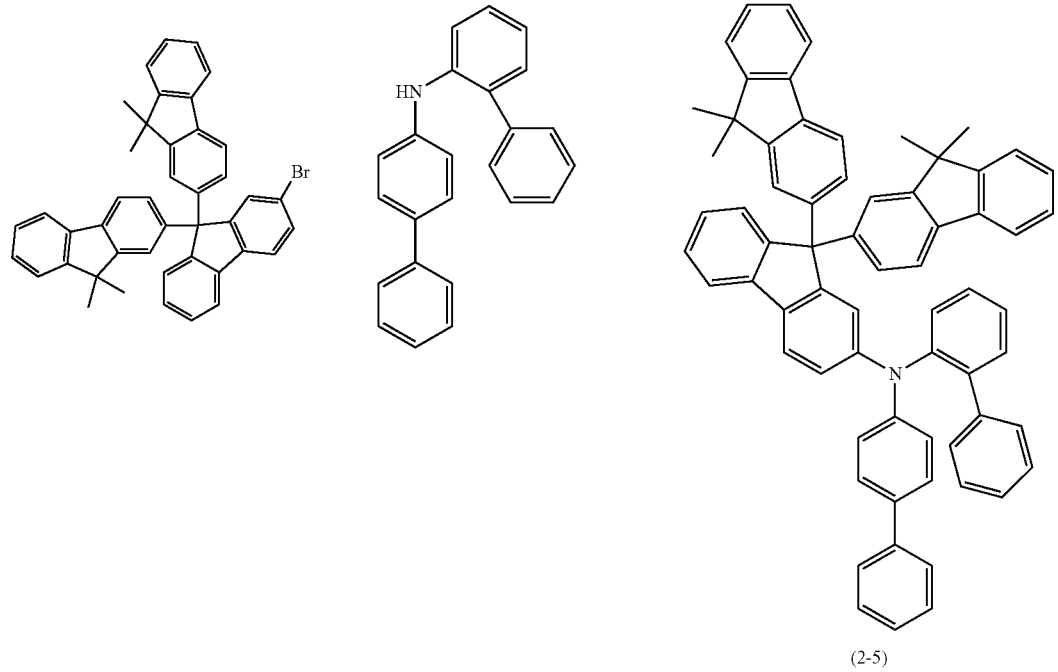
(2-5)
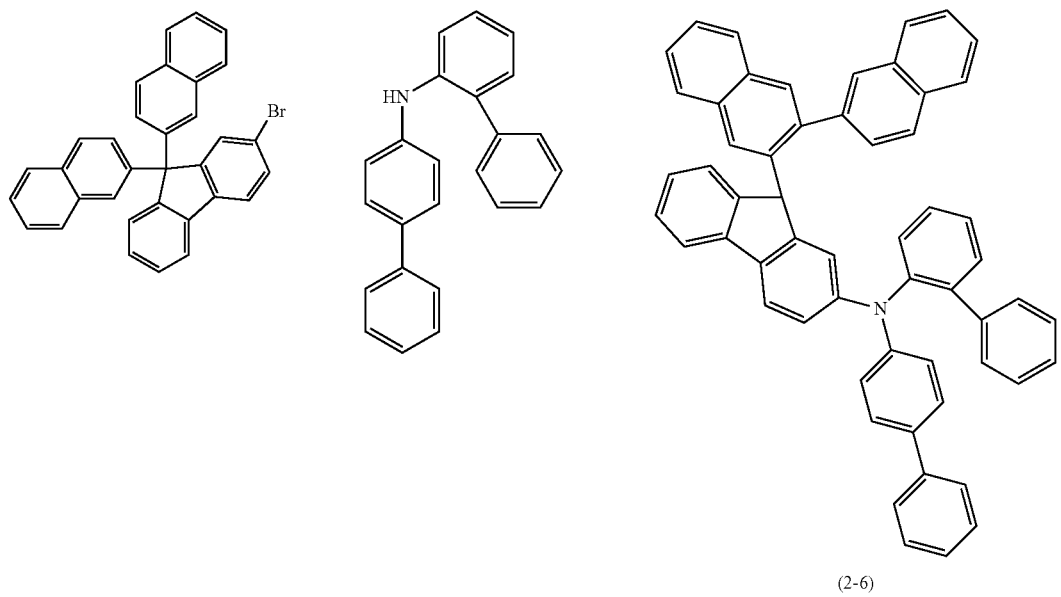
(2-6)

-continued
| Starting material 1 | Starting material 2 | Product | Yield |
|---|---|---|---|
| | | | 77% |
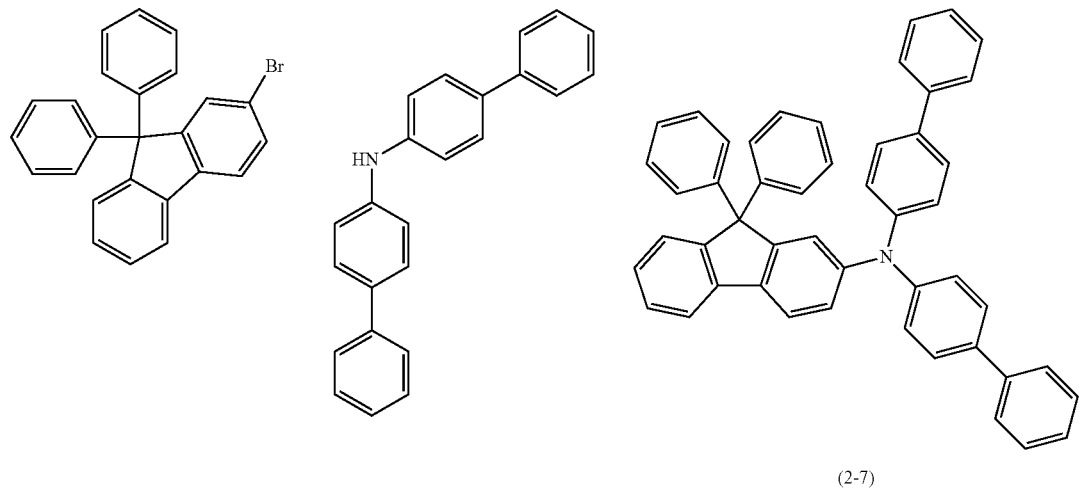
(2-7)
| | | | 65% |
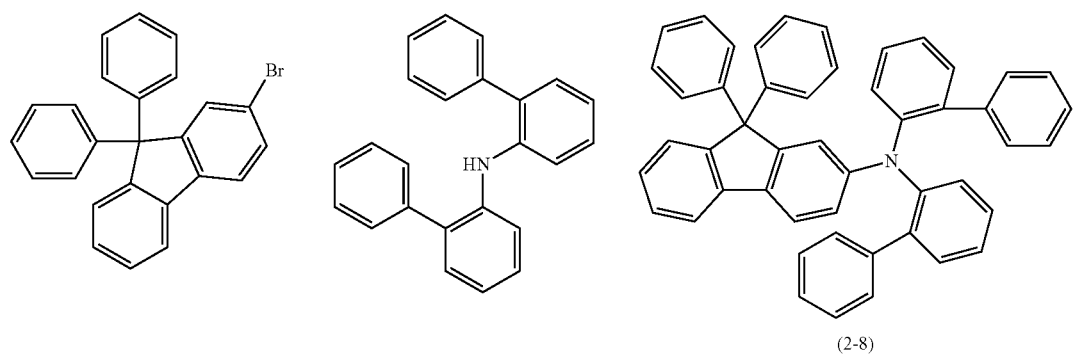
(2-8)
| | | | 62% |
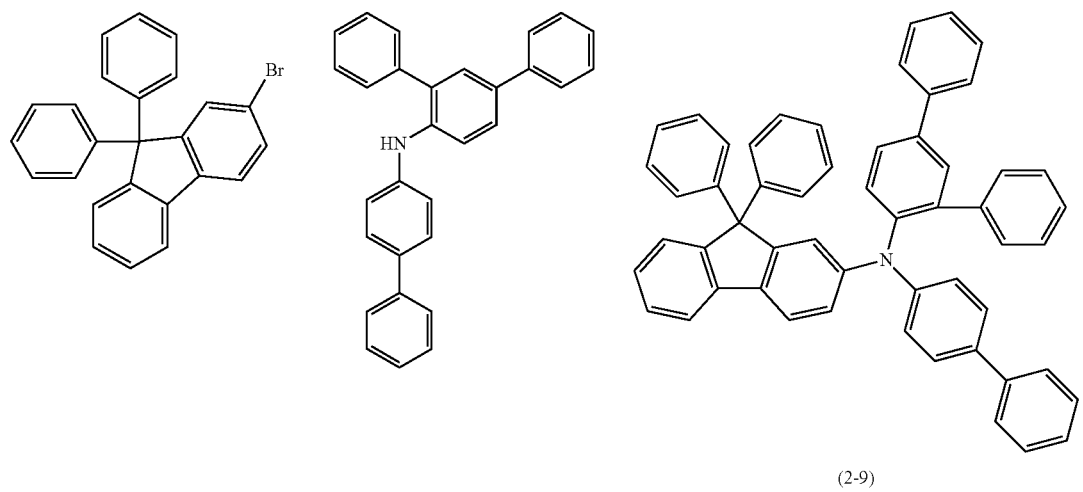
(2-9)

| Starting material 1 | Starting material 2 | Product | Yield |
|---|---|---|---|
| | | (2-10) | 70% |
Example 3
Synthesis of the Compound biphenyl-4-ylbiphenyl-2-yl-(9,9-dimethyl-7-phenyl-9H-fluoren-2-yl)amine (3-1) and Compounds (3-2) to (3-8)
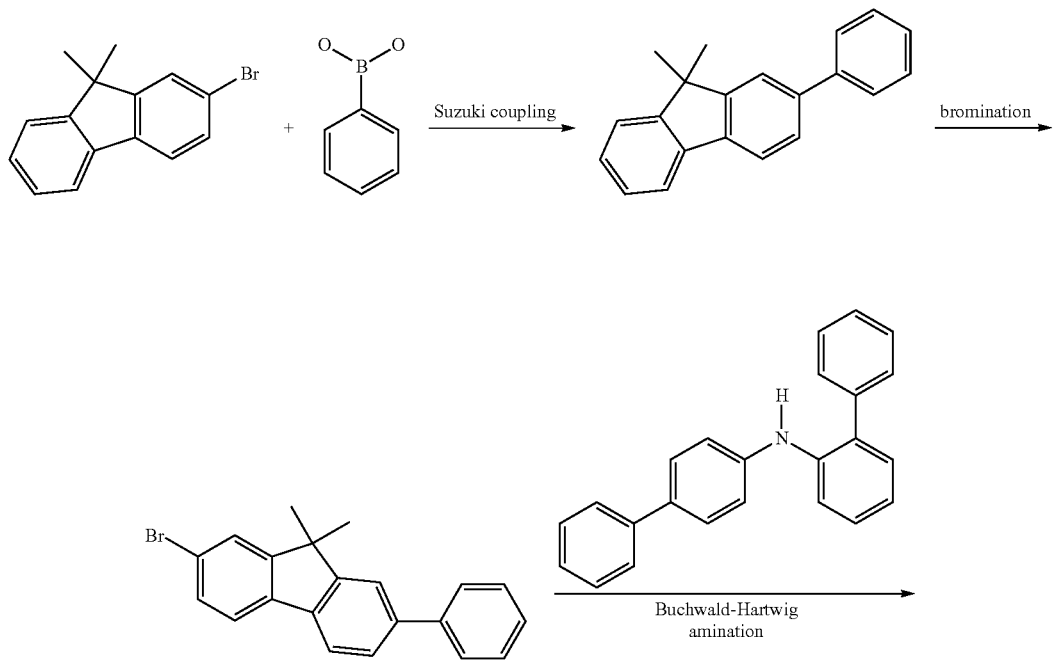

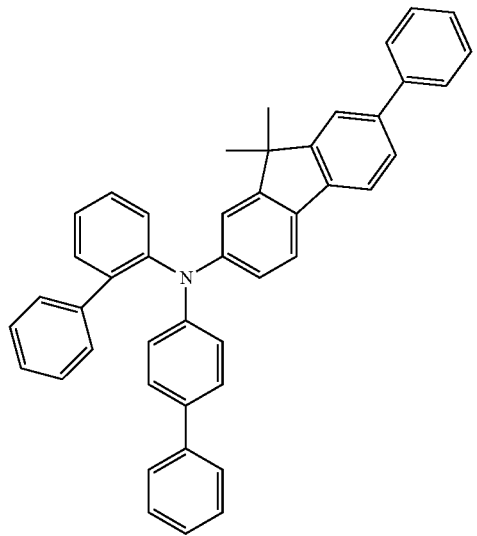

(3-1)

9,9-Dimethyl-7-phenyl-9H-fluorene 8.9 g (73 mmol) of benzeneboronic acid and 20 g (73 mmol) of 2-bromo-9,9'-dimethyl-9H-fluorene are suspended in 330 ml of dimethoxyethane and 110 ml of 2 M Na$_2$CO$_3$ solution. 2.54 g (2.0 mmol) of tetrakis(triphenyl-phosphine) palladium are added to this suspension. The reaction mixture is heated under reflux for 16 h. After cooling, the reaction mixture is diluted with ethyl acetate, and the organic phase is separated off, washed three times with 100 ml of water and subsequently evaporated to dryness. Filtration of the crude product through silica gel with heptane/ethyl acetate (20:1) gives 18.8 g (95%) of 9,9-dimethyl-7-phenyl-9H-fluorene.

The following fluorenes are prepared analogously.

| Starting material 1 | Starting material 2 | Product | Yield |
|---|---|---|---|
| 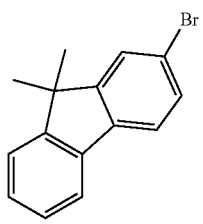 [SMILES: CC1(C)c2ccccc2-c2ccc(Br)cc21] | 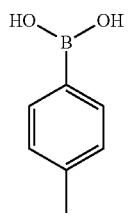 | 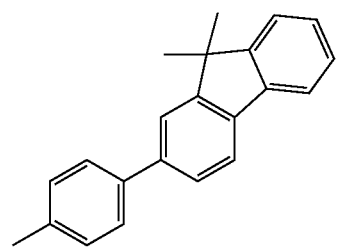 [SMILES: Cc1ccc(-c2ccc3c(c2)C(C)(C)c2ccccc2-3)cc1] | 90% |
| 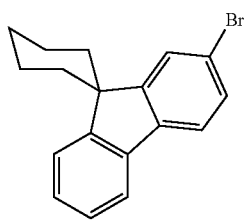 [SMILES: Brc1ccc2c(c1)C1(CCCCC1)c1ccccc1-2] | 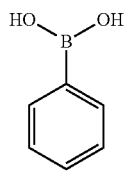 | 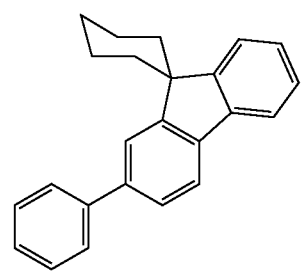 [SMILES: c1ccc(-c2ccc3c(c2)C2(CCCCC2)c2ccccc2-3)cc1] | 93% |

| Starting material 1 | Starting material 2 | Product | Yield |
|---|---|---|---|
| 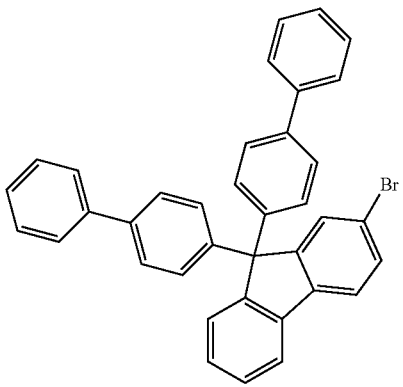 [SMILES: Brc1ccc2c(c1)C(c1ccc(-c3ccccc3)cc1)(c1ccc(-c3ccccc3)cc1)c1ccccc1-2] | 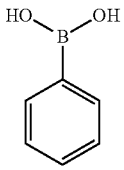 | 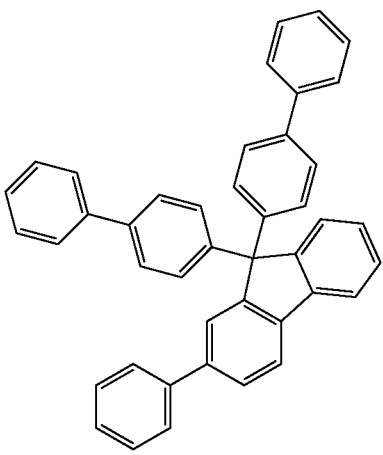 [SMILES: c1ccc(-c2ccc(C3(c4ccc(-c5ccccc5)cc4)c4ccccc4-c4ccc(-c5ccccc5)cc43)cc2)cc1] | 88% |
| 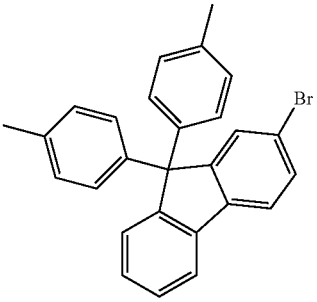 [SMILES: Cc1ccc(C2(c3ccc(C)cc3)c3ccccc3-c3ccc(Br)cc32)cc1] | 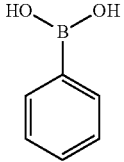 | 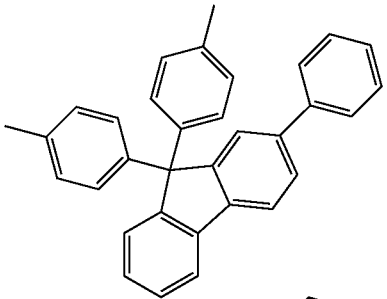 [SMILES: Cc1ccc(C2(c3ccc(C)cc3)c3ccccc3-c3ccc(-c4ccccc4)cc32)cc1] | 95% |
| 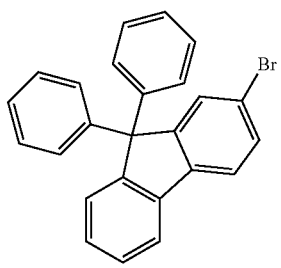 [SMILES: Brc1ccc2c(c1)C(c1ccccc1)(c1ccccc1)c1ccccc1-2] | 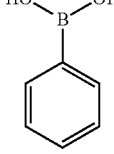 | 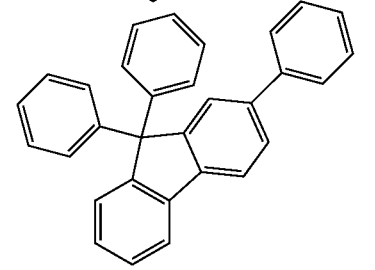 [SMILES: c1ccc(-c2ccc3c(c2)C(c2ccccc2)(c2ccccc2)c2ccccc2-3)cc1] | 80% |

2-Bromo-9,9-dimethyl-7-phenyl-9H-fluorene 29.0 g (107 mmol) of 9,9-dimethyl-2-phenyl-9H-fluorene are dissolved in 250 ml of CHCl$_3$, and 17.2 g (107 mmol) of bromine, dissolved in 50 ml of CHCl$_3$, are slowly added at −10° C. When the reaction is complete, water is added, and the organic phase is separated off, dried and evaporated. The crude product is subsequently washed a number of times by stirring with hot MeOH/heptane (1:1). The yield is 33.3 g (89% of theory) of the product as a white solid.

The following brominated compounds are prepared analogously.

| Starting material 1 | Product | Yield |
|---|---|---|
| 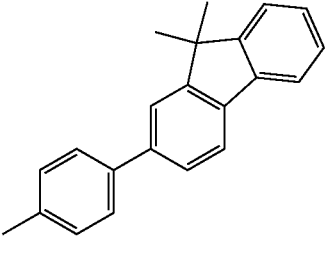 [SMILES: Cc1ccc(-c2ccc3c(c2)C(C)(C)c2ccccc2-3)cc1] | 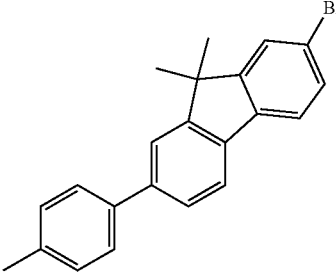 | 80% |

| Starting material 1 | Product | Yield |
|---|---|---|
| | | 75% |
| | | 72% |
| | | 65% |
| | | 80% |

Biphenyl-4-ylbiphenyl-2-yl-(9,9-dimethyl-7-phenyl-9H-fluoren-2-yl)amine (3-1)

19.9 g of biphenyl-2-ylbiphenyl-4-ylamine (62 mmol) and 21.6 g of 2-bromo-9,9-dimethyl-7-phenyl-9H-fluorene (62 mmol) are dissolved in 400 ml of toluene. The solution is degassed and saturated with $N_2$. 3 ml (3 mmol) of a 1 M tri-tert-butylphosphine solution and 0.57 g (2 mmol) of palladium(II) acetate are then added. 14.9 g of sodium Cert-butoxide (155 mmol) are subsequently added. The reaction mixture is heated at the boil for 5 h under a protective atmosphere. The mixture is subsequently partitioned between toluene and water, and the organic phase is washed three times with water, dried over $Na_2SO_4$ and evaporated in a rotary evaporator. After the crude product has been filtered through silica gel with toluene, the residue which remains is recrystallised from heptane/toluene and finally sublimed in a high vacuum. The purity is 99.9%. The yield is 29.7 g (82% of theory).
Compounds (3-2) to (3-8) are prepared analogously,
| Starting material 1 | Starting material 2 | Product | Yield |
|---|---|---|---|
| 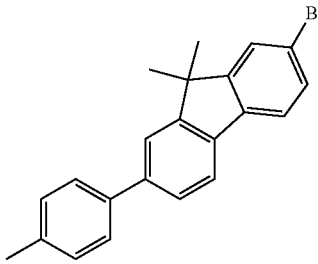 | 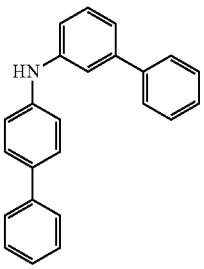 | 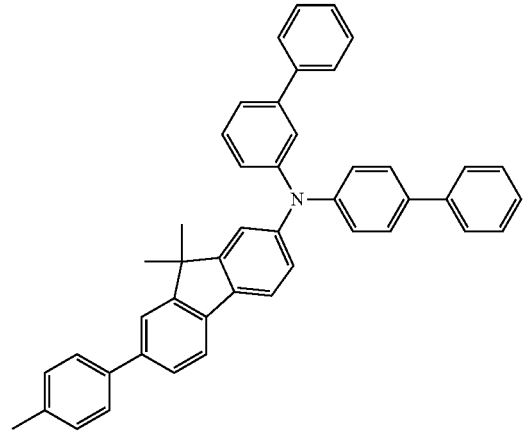 (3-2) | 77% |
| 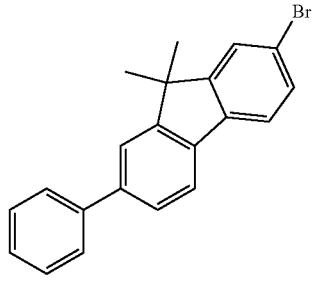 [SMILES: CC1(C)c2cc(Br)ccc2-c2ccc(-c3ccccc3)cc21] | 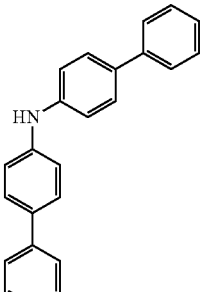 | 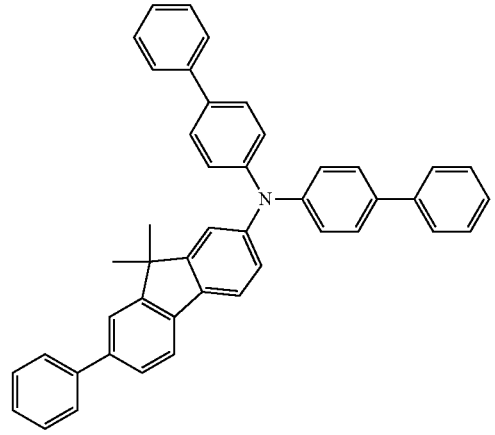 (3-3) | 87% |
| 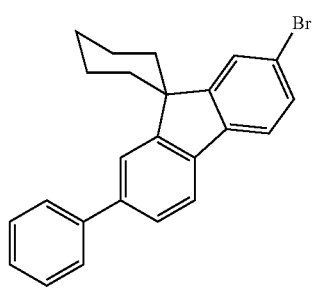 [SMILES: Brc1ccc2c(c1)C1(CCCCC1)c1cc(-c3ccccc3)ccc1-2] | 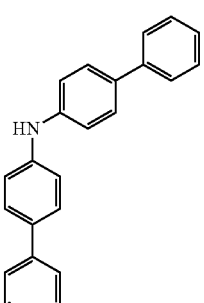 | 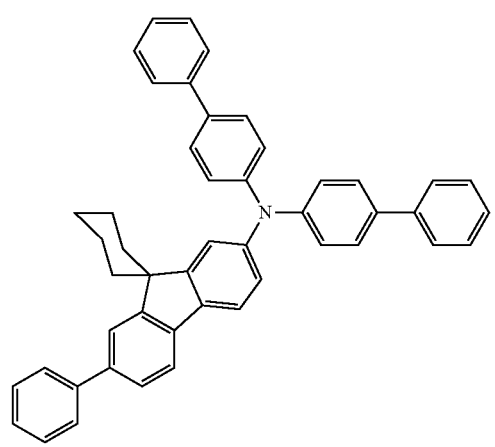 (3-4) | 84% |

-continued

| Starting material 1 | Starting material 2 | Product | Yield |
|---|---|---|---|
| (structure) | (structure) | (3-5) | 75% |
| (structure) | (structure) | (3-6) | 82% |
| (structure) | (structure) | (3-7) | 85% |

| Starting material 1 | Starting material 2 | Product | Yield |
|---|---|---|---|
| 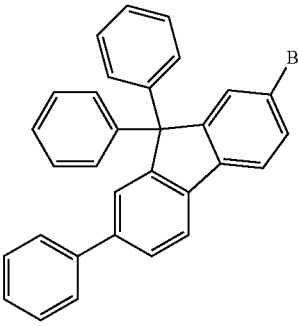 | 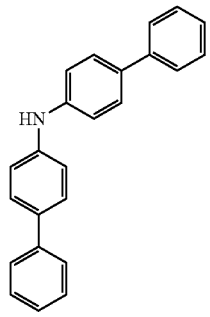 [SMILES: c1ccc(-c2ccc(Nc3ccc(-c4ccccc4)cc3)cc2)cc1] | 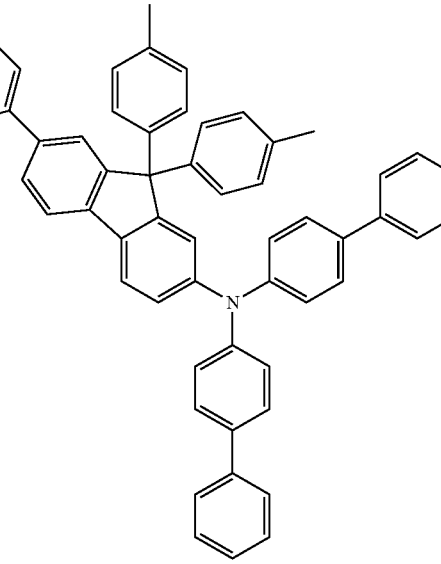(3-8) | 76% |
Example 4
Synthesis of Comparative Compounds HTMV1 to HTMV6
The following comparative compounds (HTMV1) to (HTMV6) are also prepared analogously to the synthesis of compound (3-1) described in Example 3.
| Starting material 1 | Starting material 2 | Product |
|---|---|---|
| 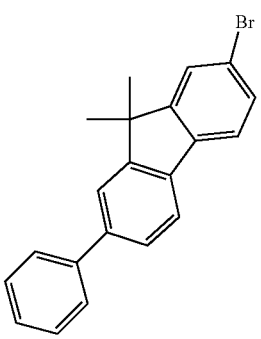 [SMILES: CC1(C)c2cc(Br)ccc2-c2ccc(-c3ccccc3)cc21] | 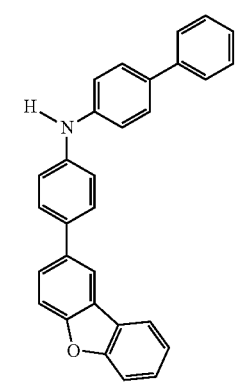 [SMILES: c1ccc(-c2ccc(Nc3ccc(-c4ccc5oc6ccccc6c5c4)cc3)cc2)cc1] | 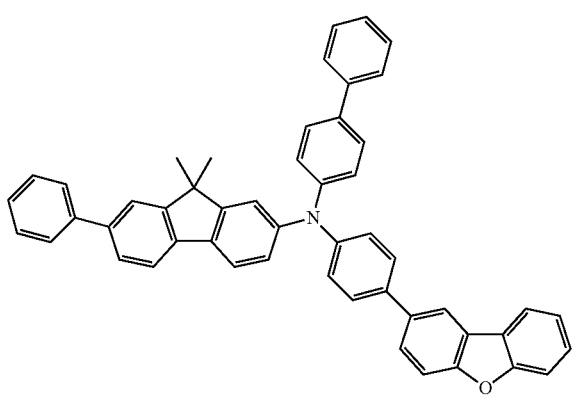HTMV1 |

| Starting material 1 | Starting material 2 | Product |
|---|---|---|
| 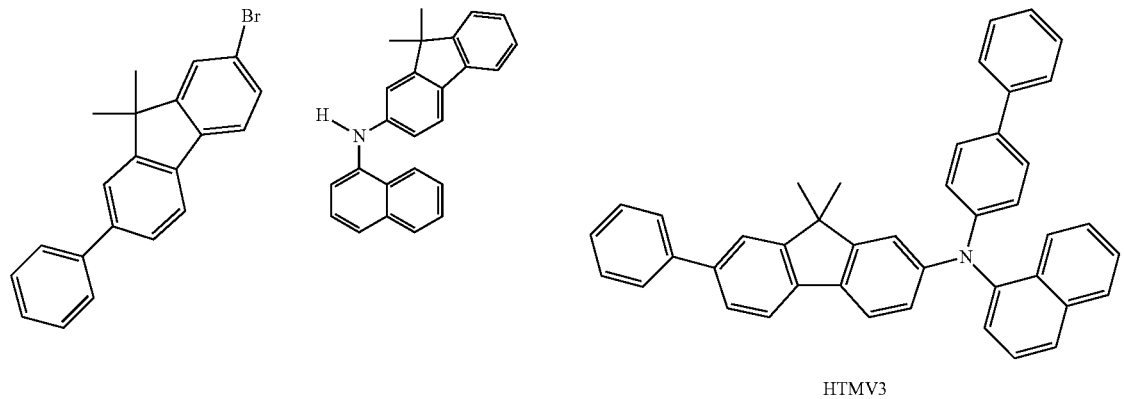 | | |
| 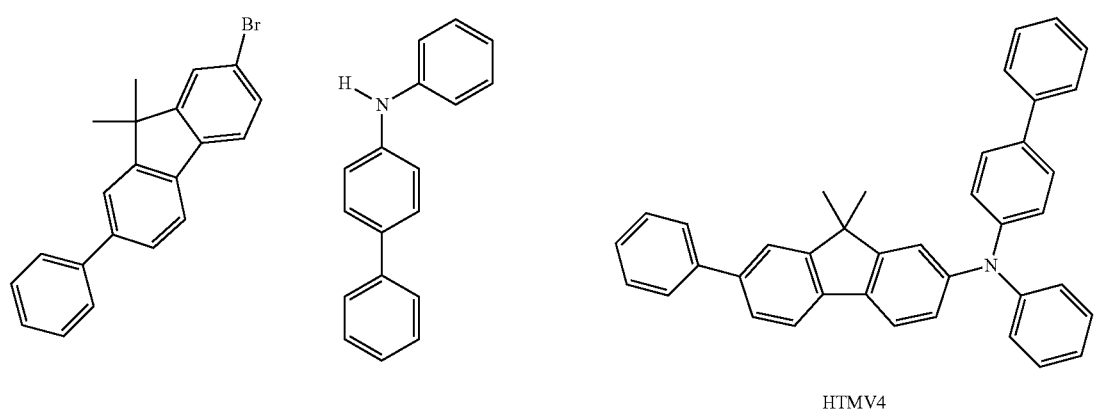 | | |
| 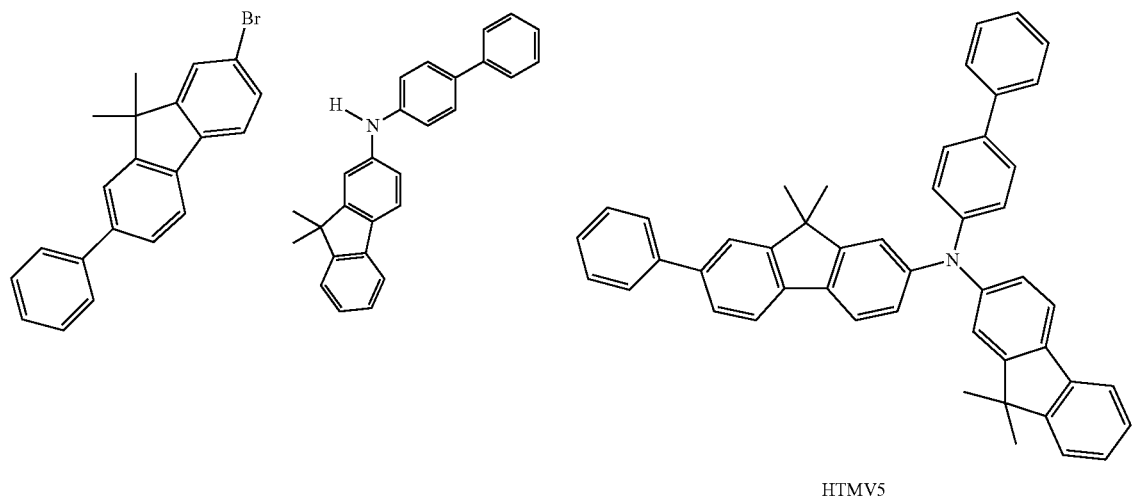 | | |

| Starting material 1 | Starting material 2 | Product |
|---|---|---|

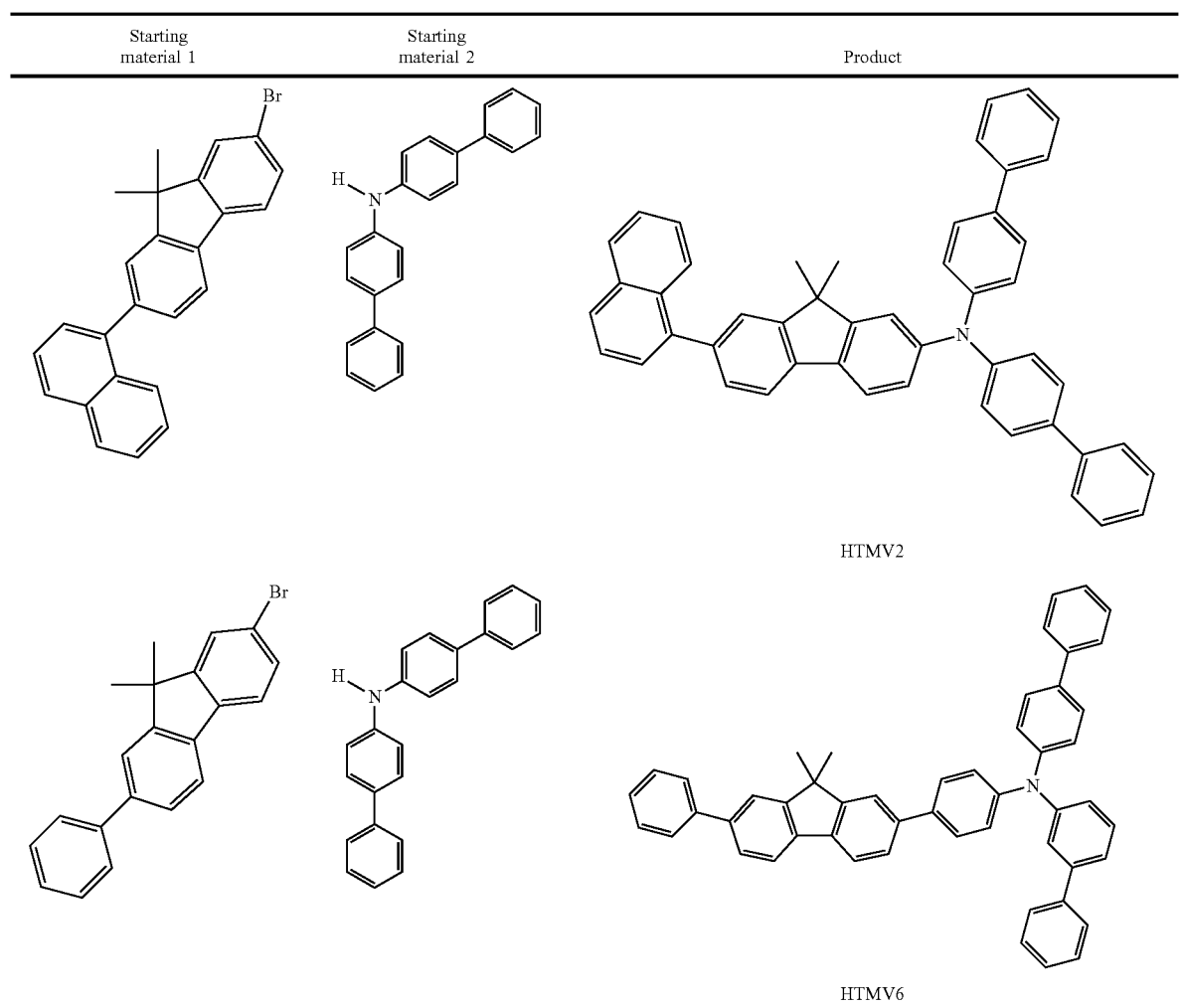

HTMV2

HTMV6

Example 5

Characterisation of the Compounds

OLEDs according to the invention and OLEDs in accordance with the prior art are produced by a general process in accordance with WO 04/058911, which is adapted to the circumstances described here (layer-thickness variation, materials).

The data for various OLEDs are presented in the following examples (see Tables 1, 3 and 2, 4). The substrates used are glass plates which have been coated with structured ITO (indium tin oxide) in a thickness of 50 nm. The OLEDs basically have the following layer structure: substrate/optional hole-injection layer (HIL1)/hole-transport layer (HTL)/hole-injection layer (HIL2)/electron-blocking layer (EBL)/emission layer (EML)/electron-transport layer (ETL)/optional electron-injection layer (EIL) and finally a cathode. The cathode is formed by an aluminium layer with a thickness of 100 nm. The precise structure of the OLEDs is shown in Tables 1 and 3. The materials required for the production of the OLEDs are indicated above.

All materials are applied by thermal vapour deposition in a vacuum chamber. The emission layer here always consists of at least one matrix material (host material) and an emitting dopant (emitter) with which the matrix material or matrix materials is (are) admixed in a certain proportion by volume by co-evaporation. An expression such as H1:SEB1 (95%:5%) here means that material H1 is present in the layer in a proportion by volume of 95% and SEB1 is present in the layer in a proportion of 5%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics, and the lifetime are determined. The electroluminescence spectra are determined at a luminous density of 1000 cd/m$^2$, and the CIE 1931 x and y colour coordinates are calculated therefrom. The expression EQE@1000 cd/m$^2$ denotes the external quantum efficiency at an operating luminous density of 1000 cd/m$^2$. LT80@6000 cd/m$^2$ is the lifetime by which the OLED has dropped from a luminance of 6000 cd/m$^2$ to 80% of the initial intensity, i.e. to 4800 cd/m$^2$. The data for the various OLEDs are summarised in Tables 2 and 4.

Use of Compounds According to the Invention as Hole-Transport Materials in Fluorescent and Phosphorescent OLEDs The compounds according to the invention are particularly suitable as HIL, HTL or EBL in OLEDs. They are suitable as a single layer, but also as a mixed component as HIL, HTL, EBL or within the EML.

Compared with NPB reference components (V1, V8), the samples comprising the compounds according to the invention, besides higher efficiencies, also exhibit significantly improved lifetimes both for singlet blue and for triplet green.

Compared with reference materials HTMV1-HTMV6 (V2-V10), the compounds according to the invention have the same or better efficiencies and improved lifetimes.

TABLE 1

Structure of the OLEDs
Layer structure: substrate/HIL1/HTL/HIL2/EBL/EML/ETL/EIL 1 nm LiQ/cathode

| Ex. | HIL1 Thickness/nm | HTL Thickness/nm | HIL2 Thickness/nm | EBL Thickness/nm | EML Thickness/nm | ETL Thickness/nm |
|---|---|---|---|---|---|---|
| V1 | HIL1 5 nm | HIL2 140 nm | HIL1 5 nm | NPB 20 nm | H1(95%):SEB1(5%) 20 nm | ETM1(50%):LiQ(50%) 30 nm |
| V2 | HIL1 5 nm | HIL2 140 nm | HIL1 5 nm | HTMV1 20 nm | H1(95%):SEB1(5%) 20 nm | ETM1(50%):LiQ(50%) 30 nm |
| V3 | HIL1 5 nm | HIL2 140 nm | HIL1 5 nm | HTMV2 20 nm | H1(95%):SEB1(5%) 20 nm | ETM1(50%):LiQ(50%) 30 nm |
| V4 | HIL1 5 nm | HIL2 140 nm | HIL1 5 nm | HTMV3 20 nm | H1(95%):SEB1(5%) 20 nm | ETM1(50%):LiQ(50%) 30 nm |
| V5 | HIL1 5 nm | HIL2 140 nm | HIL1 5 nm | HTMV4 20 nm | H1(95%):SEB1(5%) 20 nm | ETM1(50%):LiQ(50%) 30 nm |
| V6 | HIL1 5 nm | HIL2 140 nm | HIL1 5 nm | HTMV5 20 nm | H1(95%):SEB1(5%) 20 nm | ETM1(50%):LiQ(50%) 30 nm |
| V7 | HIL1 5 nm | HIL2 140 nm | HIL1 5 nm | HTMV6 20 nm | H1(95%):SEB1(5%) 20 nm | ETM1(50%):LiQ(50%) 30 nm |
| E1 | HIL1 5 nm | HIL2 140 nm | HIL1 5 nm | (3-3) 20 nm | H1(95%):SEB1(5%) 20 nm | ETM1(50%):LiQ(50%) 30 nm |
| E2 | HIL1 5 nm | HIL2 140 nm | HIL1 5 nm | (3-1) 20 nm | H1(95%):SEB1(5%) 20 nm | ETM1(50%):LiQ(50%) 30 nm |
| E3 | HIL1 5 nm | HIL2 140 nm | HIL1 5 nm | (2-1) 20 nm | H1(95%):SEB1(5%) 20 nm | ETM1(50%):LiQ(50%) 30 nm |
| E4 | HIL1 5 nm | HIL2 140 nm | HIL1 5 nm | (2-2) 20 nm | H1(95%):SEB1(5%) 20 nm | ETM1(50%):LiQ(50%) 30 nm |
| E5 | HIL1 5 nm | HIL2 140 nm | HIL1 5 nm | (2-7) 20 nm | H1(95%):SEB1(5%) 20 nm | ETM1(50%):LiQ(50%) 30 nm |

TABLE 2

Data for the OLEDs

| Ex. | EQE @ 1000 cd/m² % | LT80 @ 6000 cd/m² [h] | CIE x | CIE y |
|---|---|---|---|---|
| V1 | 4.8 | 70 | 0.14 | 0.17 |
| V2 | 6.9 | 120 | 0.13 | 0.14 |
| V3 | 7.0 | 115 | 0.13 | 0.15 |
| V4 | 6.8 | 105 | 0.13 | 0.15 |
| V5 | 6.6 | 105 | 0.13 | 0.15 |
| V6 | 6.6 | 120 | 0.13 | 0.14 |
| V7 | 7.3 | 15 | 0.14 | 0.15 |
| E1 | 7.2 | 140 | 0.13 | 0.15 |
| E2 | 7.0 | 135 | 0.13 | 0.14 |
| E3 | 6.6 | 150 | 0.13 | 0.15 |
| E4 | 6.4 | 145 | 0.13 | 0.15 |
| E5 | 6.6 | 155 | 0.13 | 0.15 |

TABLE 3

Structure of the OLEDs
Layer structure: substrate/HTL/HIL2/EBL/EML/ETL/cathode

| Ex | HTL Thickness/nm | HIL2 Thickness/nm | EBL Thickness/nm | EML Thickness/nm | ETL Thickness/nm |
|---|---|---|---|---|---|
| V8 | HIL2 70 nm | HIL1 5 nm | NPB 20 nm | H2(88%): Irpy(12%) 30 nm | ETM1(50%): LiQ(50%) 40 nm |

TABLE 3-continued

Structure of the OLEDs
Layer structure: substrate/HTL/HIL2/EBL/EML/ETL/cathode

| Ex | HTL Thickness/ nm | HIL2 Thickness/ nm | EBL Thickness/ nm | EML Thickness/ nm | ETL Thickness/ nm |
|---|---|---|---|---|---|
| V9 | HIL2 70 nm | HIL1 5 nm | HTMV5 20 nm | H2(88%): Irpy(12%) 30 nm | ETM1(50%): LiQ(50%) 40 nm |
| V10 | HIL2 70 nm | HIL1 5 nm | HTMV6 20 nm | H2(88%): Irpy(12%) 30 nm | ETM1(50%): LiQ(50%) 40 nm |
| E6 | HIL2 70 nm | HIL1 5 nm | (2-1) 20 nm | H2(88%): Irpy(12%) 30 nm | ETM1(50%): LiQ(50%) 40 nm |
| E7 | HIL2 70 nm | HIL1 5 nm | (2-2) 20 nm | H2(88%): Irpy(12%) 30 nm | ETM1(50%): LiQ(50%) 40 nm |
| E8 | HIL2 70 nm | HIL1 5 nm | (2-7) 20 nm | H2(88%): Irpy(12%) 30 nm | ETM1(50%): LiQ(50%) 40 nm |

TABLE 4

Data for the OLEDs

| Ex. | Efficiency @ 1000 cd/m² % | LT80 @ 8000 cd/m² [h] | CIE x | CIE y |
|---|---|---|---|---|
| V8 | 13.4 | 85 | 0.32 | 0.63 |
| V9 | 17.0 | 155 | 0.37 | 0.61 |
| V10 | 18.1 | 65 | 0.37 | 0.61 |
| E6 | 17.6 | 195 | 0.37 | 0.61 |
| E7 | 17.1 | 185 | 0.37 | 0.61 |
| E8 | 17.5 | 200 | 0.37 | 0.61 |

The invention claimed is:

1. An electroluminescent device comprising at least one compound of the general formula (1)

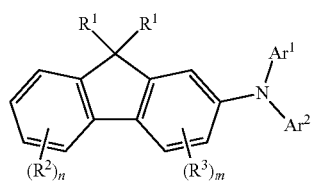

formula (1)

where the following applies to the symbols and indices occurring:

$Ar^1$ and $Ar^2$ are on each occurrence, identically or differently, an aromatic or heteroaromatic group having two or more aromatic or heteroaromatic rings and having 10 to 60 ring atoms in said aromatic or heteroaromatic group, which is optionally substituted by one or more radicals $R^4$, which are identical to or different from one another, wherein either $Ar^1$ or $Ar^2$ comprises at least one heteroaromatic group having 6 to 60 aromatic ring atoms, which is optionally substituted by one or more radicals $R^4$, which are identical to or different from one another;

wherein at least one $Ar^1$ or $Ar^2$ is selected from the group consisting of radicals having the formulae (43)-(54) and (55):

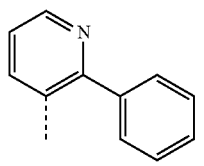

formula (43)

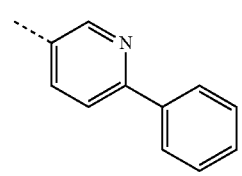

formula (44)

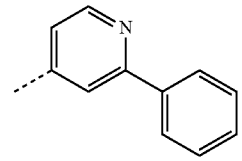

formula (45)

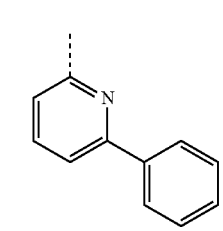

formula (46)

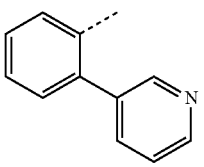

formula (47)

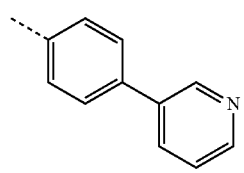

formula (48)

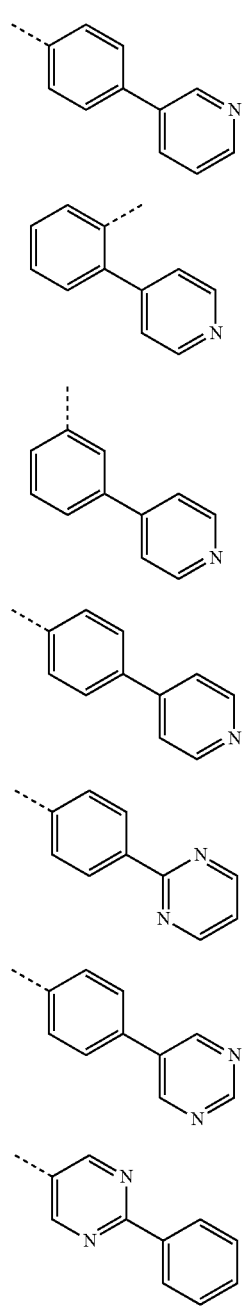

formula (49)
formula (50)
formula (51)
formula (52)
formula (53)
formula (54)
formula (55)

wherein the radicals having the formulas (43) to (55) may be substituted, by one or more radicals $R^4$, which are identical to or different from one another;

$R^1$
is on each occurrence, identically or differently, H, D, F, Cl, Br, I, C(=O)$R^5$, CN, Si($R^5$)$_3$, NO$_2$, P(=O)($R^5$)$_2$, S(=O)$R^5$, S(=O)$_2R^5$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^5$ and where one or more CH$_2$ groups in the above-mentioned groups is optionally replaced by —$R^5$C=C$R^5$—, —C≡C—, Si($R^5$)$_2$, C=O, C=S, C=N$R^5$, —C(=O)O—, —C(=O)N$R^5$—, P(=O)($R^5$), —O—, —S—, SO or SO$_2$ and where one or more H atoms in the above-mentioned groups is optionally replaced by D, F, Cl, Br, I, CN or NO$_2$, or an aromatic or heteroaromatic ring system having 6 to 30 ring atoms, which may in each case be substituted by one or more radicals $R^5$, or a condensed ring system having 9 to 30 ring atoms, which may in each case be substituted by one or more radicals $R^5$, where, in the case of aromatic or heteroaromatic condensed rings, not more than 10 ring atoms is optionally present; the two radicals $R^1$ may also form a ring closure with one another, so that a spiro compound forms, where no aromatic or heteroaromatic rings are condensed onto the ring formed by the two radicals $R^1$;

$R^2$, $R^3$ and $R^4$
are on each occurrence, identically or differently, H, D, F, Cl, Br, I, C(=O)$R^5$, CN, Si($R^5$)$_3$, NO$_2$, P(=O)($R^5$)$_2$, S(=O)$R^5$, S(=O)$_2R^5$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^5$ and where one or more CH$_2$ groups in the above-mentioned groups is optionally replaced by —$R^5$C=C$R^5$—, —C≡C—, Si($R^5$)$_2$, C=O, C=S, C=N$R^5$, —C(=O)O—, —C(=O)N$R^5$—, P(=O)($R^5$), —O—, —S—, SO or SO$_2$ and where one or more H atoms in the above-mentioned groups is optionally replaced by D, F, Cl, Br, I, CN or NO$_2$, or an aromatic or heteroaromatic ring system having 6 to 30 ring atoms, which may in each case be substituted by one or more radicals $R^5$;

$R^5$
is on each occurrence, identically or differently, H, D, F, Cl, Br, I, C(=O)$R^6$, CN, Si($R^6$)$_3$, NO$_2$, P(=O)($R^6$)$_2$, S(=O)$R^6$, S(=O)$_2R^6$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^6$ and where one or more CH$_2$ groups in the above-mentioned groups is optionally replaced by —$R^6$C=C$R^6$—, —C≡C—, Si($R^6$)$_2$, C=O, C=S, C=N$R^6$, —C(=O)O—, —C(=O)N$R^6$—, P(=O)($R^6$), —O—, —S—, SO or SO$_2$ and where one or more H atoms in the above-mentioned groups is optionally replaced by D, F, Cl, Br, I, CN or NO$_2$, or an aromatic or heteroaromatic ring system having 5 to 30 aromatic ring atoms, which may in each case be substituted by one or more radicals $R^6$, or an aryloxy or heteroaryloxy group having 5 to 30 aromatic ring atoms, which is optionally substituted by one or more radicals $R^6$;

$R^6$
is on each occurrence, identically or differently, H, D, F or an aliphatic, aromatic or heteroaromatic organic radical having 1 to 20 C atoms, in which, in addition, one or more H atoms is optionally replaced by D or F;

n is 0, 1, 2, 3 or 4;
m is 0, 1, 2 or 3;
with the proviso that the compound of the formula (1), besides the one fluorene group and besides the possible condensed or polycyclic groups in position 9 of the fluorene, contains no further polycyclic or condensed groups or
the compound of formula (1) is selected from the group consisting of formula (94)-(96), (138)-(140) and (201)-(203):
formula (94)
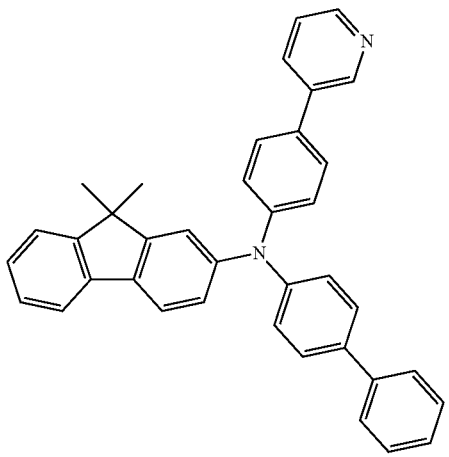
formula (95)
formula (96)
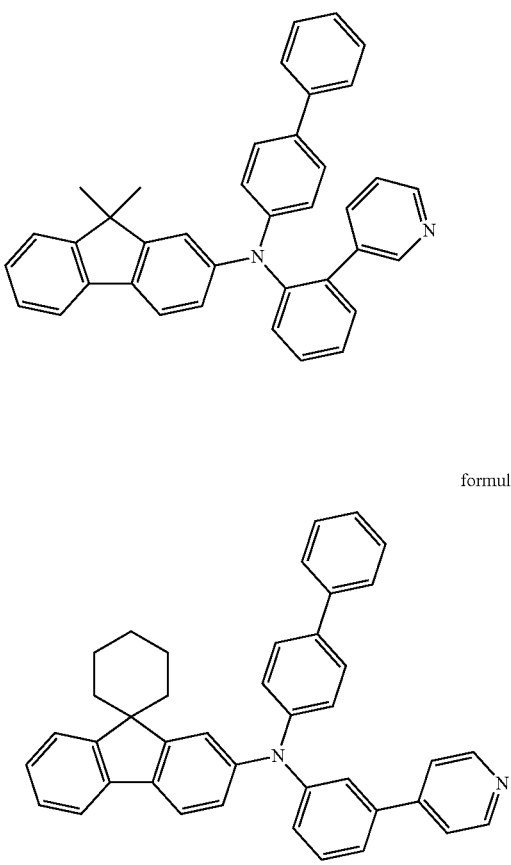
formula (138)
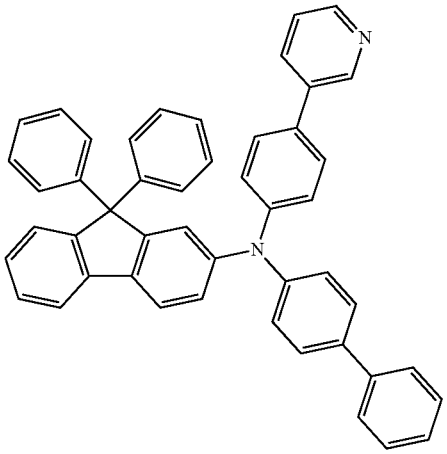
formula (139)
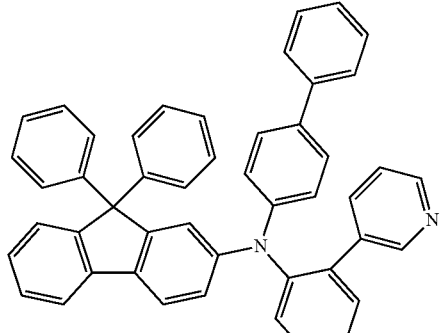
formula (140)
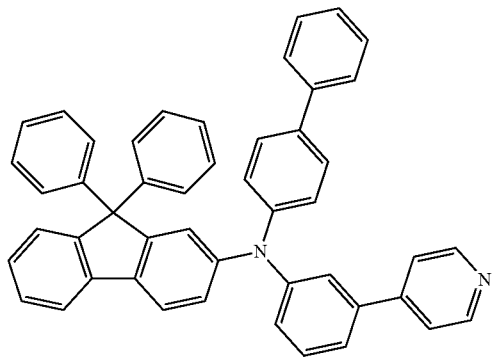

-continued

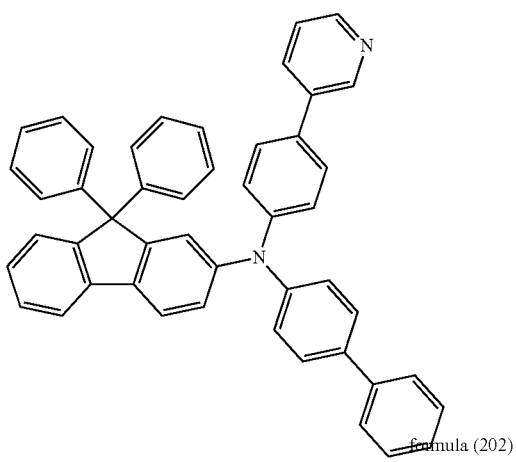

formula (201)

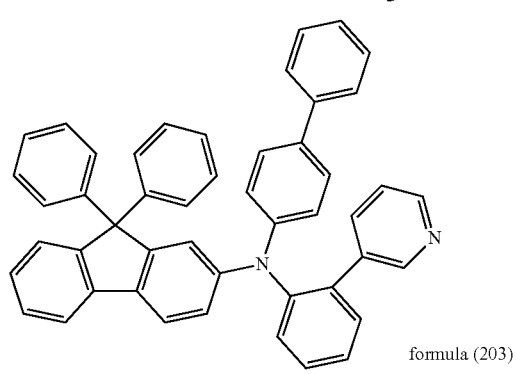

formula (202)

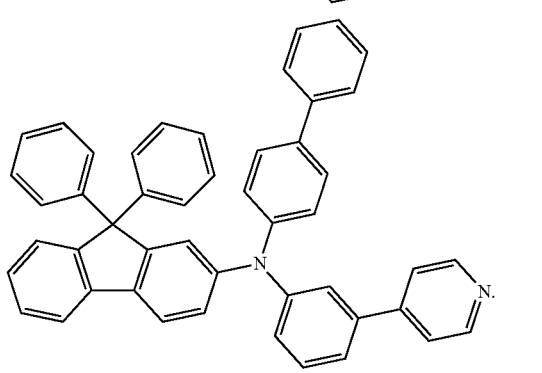

formula (203)

2. The device according to claim 1, wherein the two radicals $R^1$ in the compound of the formula (1) are identical.

3. The device according to claim 1, wherein m is equal to 1 and n is equal to 0, 1 or 2.

4. The device according to claim 1, wherein it comprises at least one compound of the general formula (2)

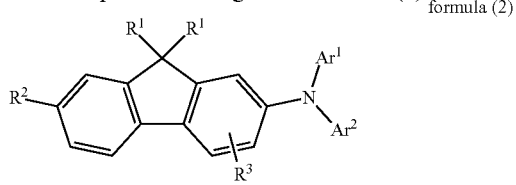

formula (2)

where the definitions from claim 1 apply to the symbols.

5. The device according to claim 1, wherein $R^3$ is equal to H.

6. The device according to claim 1, wherein $Ar^1$ and $Ar^2$ are identical or different and are selected from a biphenyl, terphenyl or quaterphenyl group, each of which is optionally substituted by one or more radicals $R^4$.

7. The device according to claim 1, wherein the two radicals $R^1$ are identical and are selected from an aromatic or heteroaromatic ring system having 6 to 30 ring atoms, which may in each case be substituted by one or more radicals $R^5$, or a condensed ring system having 9 to 30 ring atoms, which may in each case be substituted by one or more radicals $R^5$, where, in the case of aromatic or heteroaromatic condensed rings, not more than 10 ring atoms is optionally present and where $R^2$ is equal to H.

8. The device according to claim 1, wherein the two radicals $R^1$ are identical and are selected from a straight-chain alkyl group having 1 to 20 C atoms or a branched or cyclic alkyl group having 3 to 20 C atoms, where the groups may each be substituted by one or more radicals $R^5$ and where one or more H atoms in the above-mentioned groups is optionally replaced by D, F, Cl, Br, I, CN or $NO_2$ and where $R^2$ is an aromatic or heteroaromatic ring system having 6 to 30 aromatic ring atoms, which may in each case be substituted by one or more radicals $R^5$.

9. The device according to claim 1, wherein it is an organic light-emitting transistor (OLET), an organic field-quench device (OFQD), an organic light-emitting electrochemical cell (OLEC, LEC or LEEC), an organic laser diode (O-laser) or an organic light-emitting diode (OLED).

10. The device according to claim 1, wherein the device is an organic light-emitting diode (OLED), wherein the compound is employed in one of the following functions: as hole-transport material in a hole-transport or hole-injection layer, as matrix material in an emitting layer, as electron-blocking material or as exciton-blocking material.

11. A compound of the general formula (167)

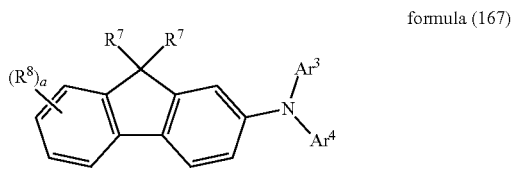

formula (167)

where the following applies to the symbols used in formula (167):

$Ar^3$ and $Ar^4$ are on each occurrence, identically or differently, an aromatic or heteroaromatic group having two or more aromatic or heteroaromatic rings and having 10 to 60 ring atoms in said aromatic or heteroaromatic group, which is optionally substituted by one or more radicals $R^5$, which are identical to or different from one another, wherein either $Ar^3$ or $Ar^4$ comprises at least one heteroaromatic group having 6 to 60 aromatic ring atoms, which is optionally substituted by one or more radicals $R^5$, which are identical to or different from one another;

wherein at least one $Ar^3$ or $Ar^4$ is selected from the group consisting of radicals having the formulae (43)-(54) and (55):

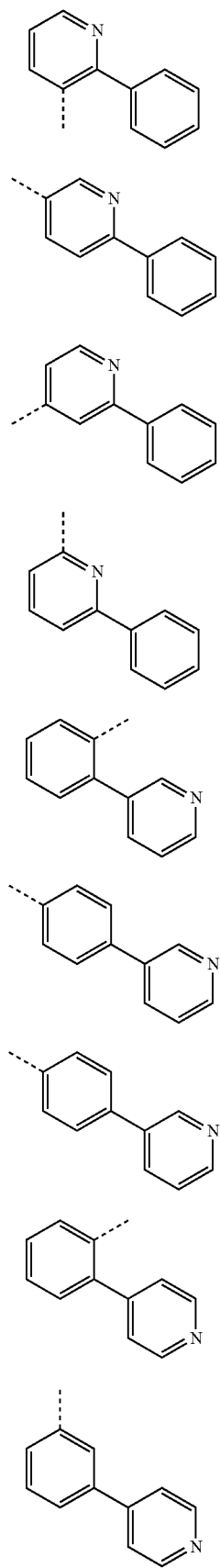

formula (43)
formula (44)
formula (45)
formula (46)
formula (47)
formula (48)
formula (49)
formula (50)
formula (51)

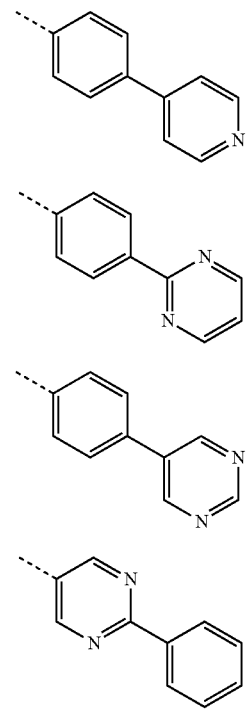

formula (52)
formula (53)
formula (54)
formula (55)

wherein the radicals having the formulas (43) to (55) may be substituted, by one or more radicals $R^4$, which are identical to or different from one another;

$R^7$ is identical on each occurrence and is selected from the group consisting of a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^5$ and where one or more H atoms in the above-mentioned groups is optionally replaced by D, CN or $NO_2$, or an aromatic or heteroaromatic ring system having 6 to 30 ring atoms, which may in each case be substituted by one or more radicals $R^5$, where $R^5$ is defined as indicated above, or a condensed ring system having 9 to 30 ring atoms, which may in each case be substituted by one or more radicals $R^5$, where, in the case of aromatic or heteroaromatic condensed rings, not more than 10 ring atoms is optionally present in the condensed ring system; the two radicals $R^7$ may also form a ring closure with one another, so that a spiro compound forms, where no aromatic or heteroaromatic rings are condensed onto the ring formed by the two radicals $R^7$, and where, if $R^7$ is a straight-chain or branched alkyl group, $R^8$ is an aromatic or heteroaromatic ring system having 6 to 30 ring atoms, which may in each case be substituted by one or more radicals $R^5$, and where $R^5$ is defined as indicated above;

$R^8$ is H, D or an aromatic or heteroaromatic ring system having 6 to 30 ring atoms, which may in each case be substituted by one or more radicals $R^5$, where $R^5$ is defined as indicated above and where, if $R^8$ is equal to H, $R^7$ is an aromatic or heteroaromatic ring system having 6 to 30 aromatic ring atoms, which may in each case be substituted by one or more radicals R⁵, where R⁵ is defined as indicated above;

a
is either 1, 2, 3 or 4;

with the proviso that the compound of the formula (167), besides the one fluorene group and besides the possible condensed or polycyclic groups in position 9 of the fluorene, contains no further polycyclic or condensed groups and with the proviso that the compound contains no halogens the compound of formula (167) is selected from the group consisting of formula (94)-(96), (138)-(140) and (201)-(203):

formula (94)
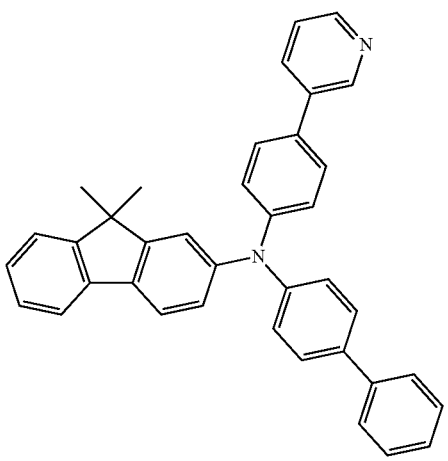

formula (95)
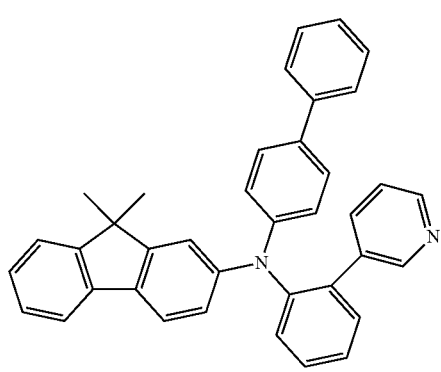

formula (96)
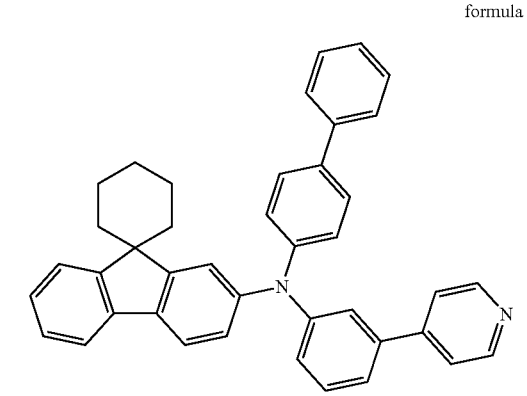

formula (138)
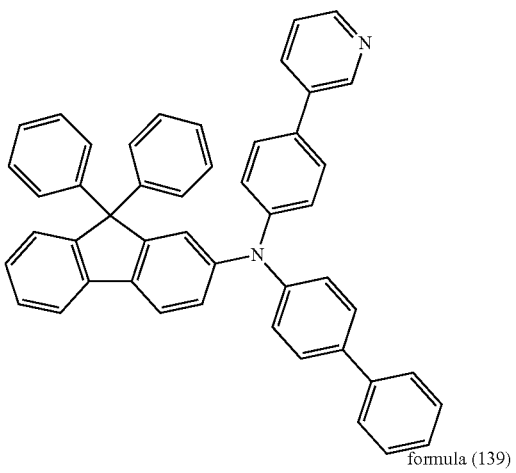

formula (139)
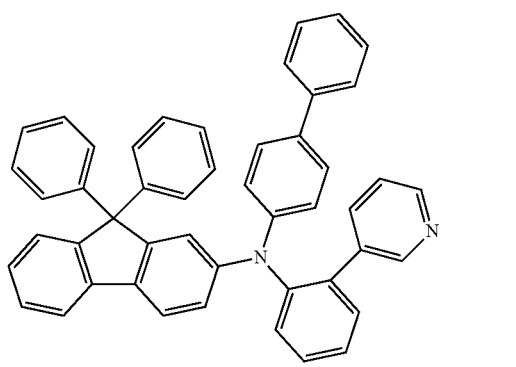

formula (140)
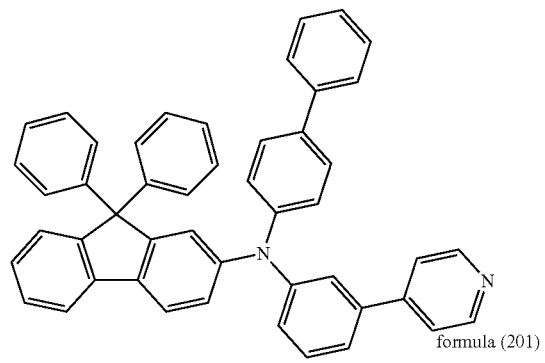

formula (201)
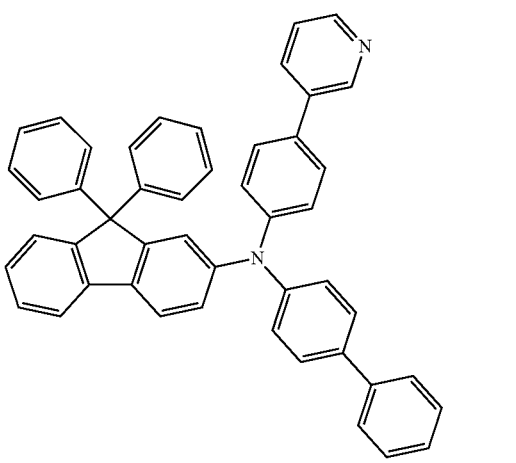

formula (202)

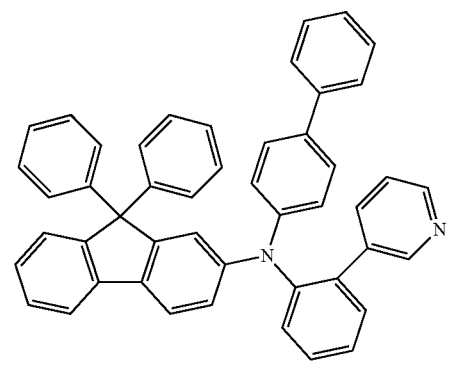

formula (203)

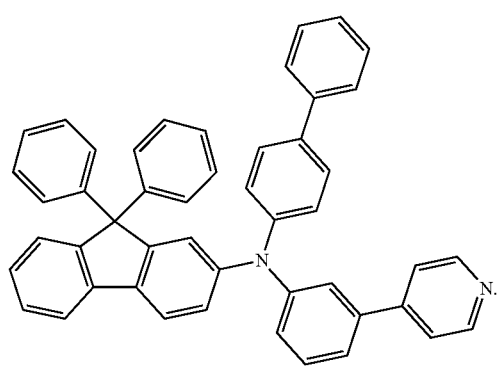

12. The compound according to claim 11, wherein the compound has the general formula (168)

formula (168)

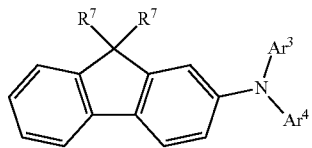

where, for the symbols used,

Ar³ and Ar⁴
are identical or different on each occurrence and are selected from a biphenyl, terphenyl or quaterphenyl group, which is optionally substituted by one or more radicals $R^5$;

wherein at least one Ar³ or Ar⁴ is selected from the group consisting of radicals having the formulae (43)-(54) and (55):

formula (43)

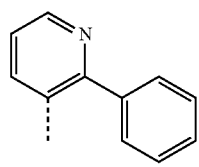

formula (44)

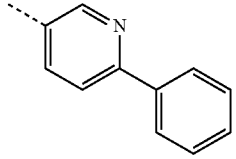

formula (45)

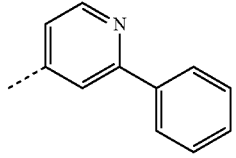

formula (46)

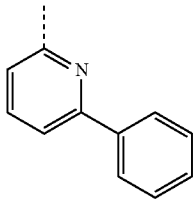

formula (47)

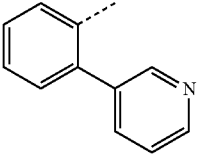

formula (48)

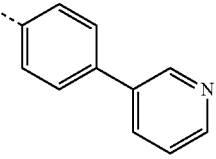

formula (49)

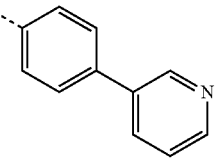

formula (50)

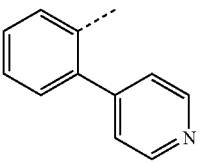

formula (51)

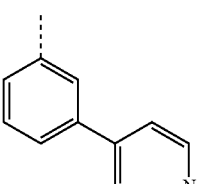

formula (52)

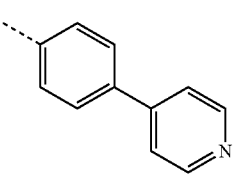

formula (53)
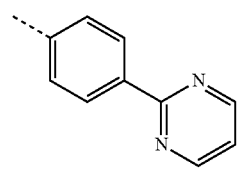

formula (54)
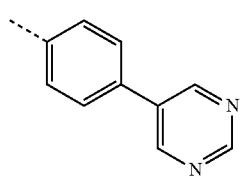

formula (55)
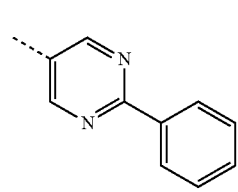

wherein the radicals having the formulas (43) to (55) may be substituted, by one or more radicals R, which are identical to or different from one another;

$R^7$
is identical on each occurrence and is selected from an aromatic or heteroaromatic ring system having 6 to 30 ring atoms, which may in each case be substituted by one or more radicals $R^5$, where $R^5$ is defined as indicated above, or a condensed ring system having 9 to 30 ring atoms, which may in each case be substituted by one or more radicals $R^5$, where, in the case of aromatic or heteroaromatic condensed rings, not more than 10 ring atoms is optionally present in the condensed ring system or the compound of formula (168) is selected from the group consisting of formula (94)-(96), (138)-(140) and (201)-(203):

formula (94)
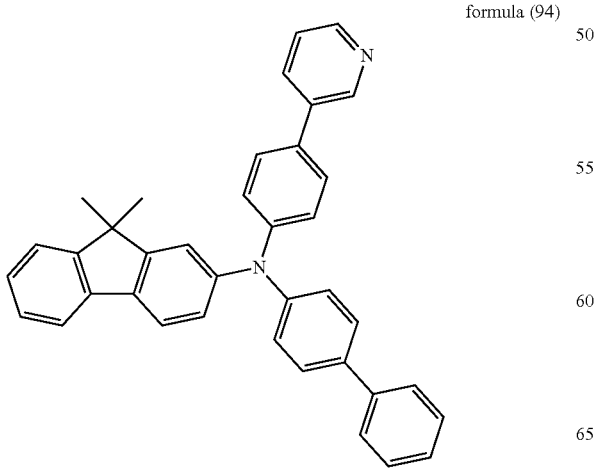

formula (95)
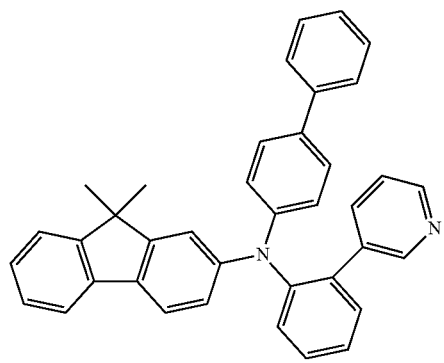

formula (96)
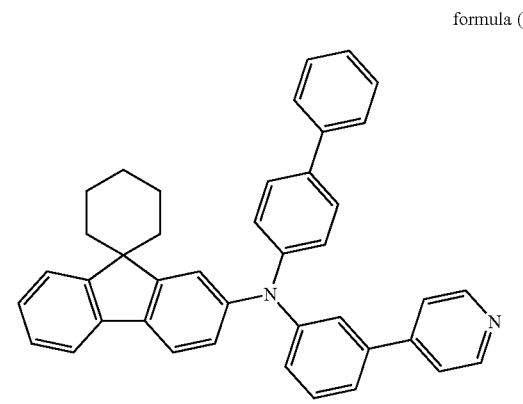

formula (138)
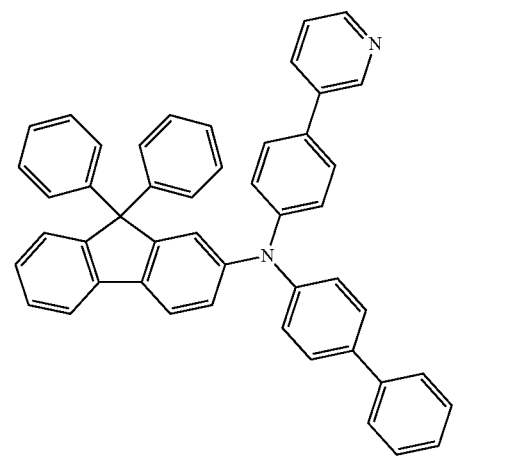

formula (139)
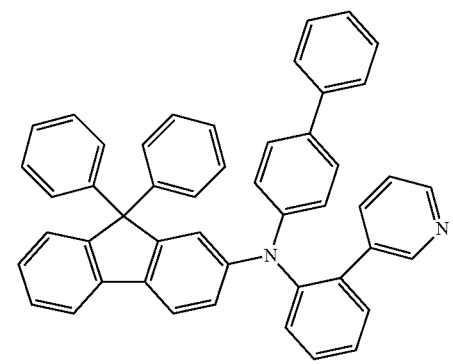

-continued formula (140)

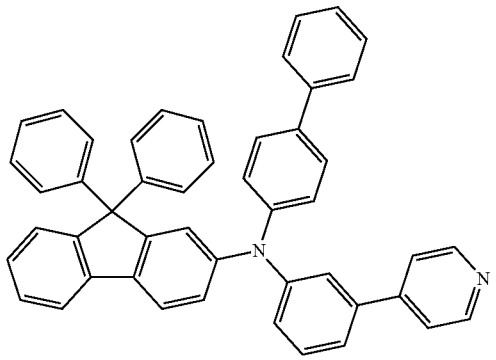

formula (201)

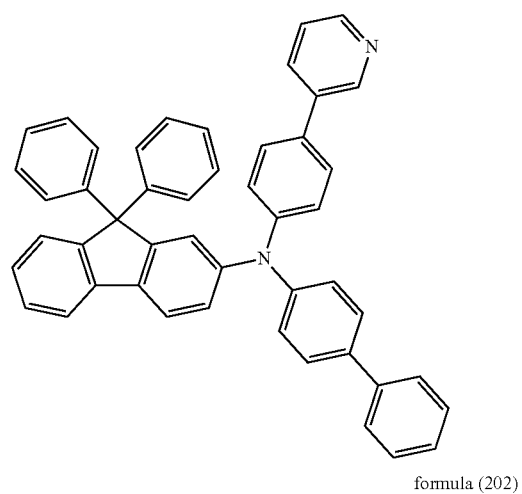

formula (202)

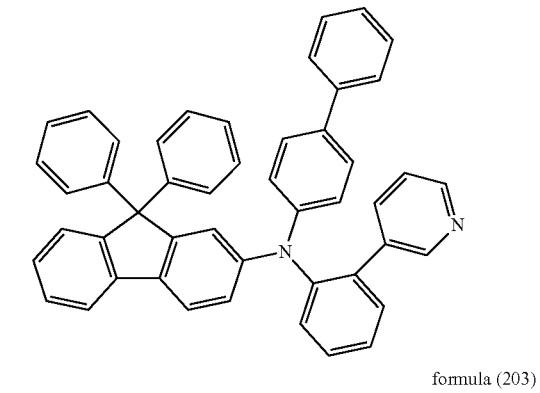

formula (203)

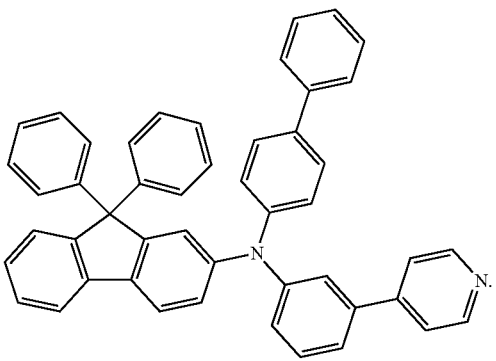

13. The compound according to claim 11, wherein the compound has the general formula (169)

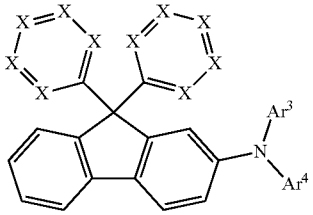

formula (169)

where, for the symbols used,

X
  is, identically or differently on each occurrence, N or $CR^5$, preferably X is equal to $CR^5$;

$Ar^3$ and $Ar^4$
  are identical or different on each occurrence and are selected from a biphenyl, terphenyl and quaterphenyl group, each of which is optionally substituted by one or more radicals $R^5$; and wherein at least one $Ar^3$ or $Ar^4$ is selected from the group consisting of radicals having the formulae (43)-(54) and (55)

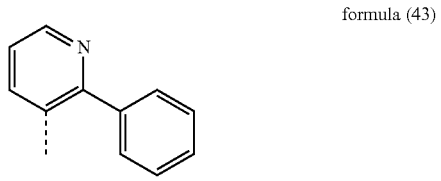

formula (43)

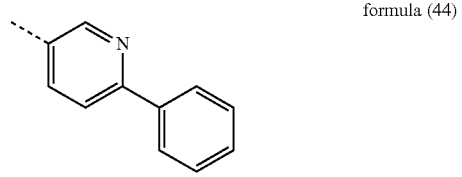

formula (44)

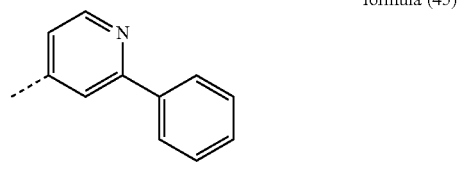

formula (45)

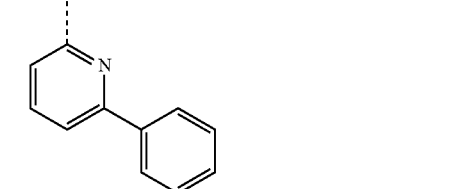

formula (46)

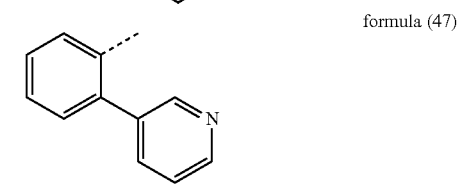

formula (47)

-continued

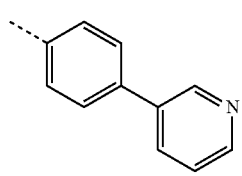
formula (48)

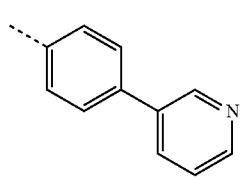
formula (49)

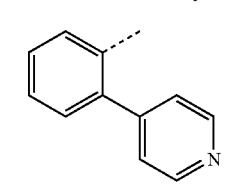
formula (50)

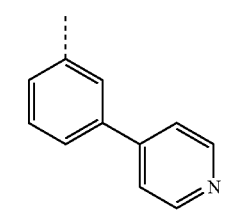
formula (51)

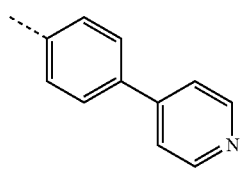
formula (52)

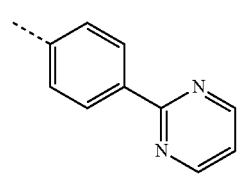
formula (53)

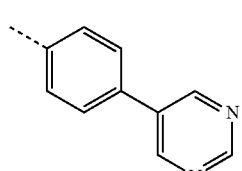
formula (54)

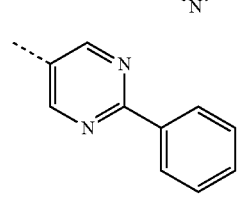
formula (55)

wherein the radicals having the formulas (43) to (55) may be substituted, by one or more radicals R⁴, which are identical to or different from one another;

R⁵
is on each occurrence, identically or differently, H, D, F, Cl, Br, I, C(=O)R⁶, CN, Si(R⁶)₃, NO₂, P(=O)(R⁶)₂, S(=O)R⁶, S(=O)₂R⁶, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals R⁶ and where one or more CH₂ groups in the above-mentioned groups is optionally replaced by —R⁶C=CR⁶—, —C≡C—, Si(R')₂, C=O, C=S, C=NR⁶, —C(=O)O—, —C(=O)NR⁶—, P(=O)(R⁶), —O—, —S—, SO or SO₂ and where one or more H atoms in the above-mentioned groups is optionally replaced by D, F, Cl, Br, I, CN or NO₂, or an aromatic or heteroaromatic ring system having 5 to 30 aromatic ring atoms, which may in each case be substituted by one or more radicals R⁶, or an aryloxy or heteroaryloxy group having 5 to 30 aromatic ring atoms, which is optionally substituted by one or more radicals R⁶;

R⁶
is on each occurrence, identically or differently, H, D, F or an aliphatic, aromatic or heteroaromatic organic radical having 1 to 20 C atoms, in which, in addition, one or more H atoms is optionally replaced by D or F or the compound of formula (169) is selected from the group consisting of formula (94)-(96), (138)-(140) and (201)-(203):

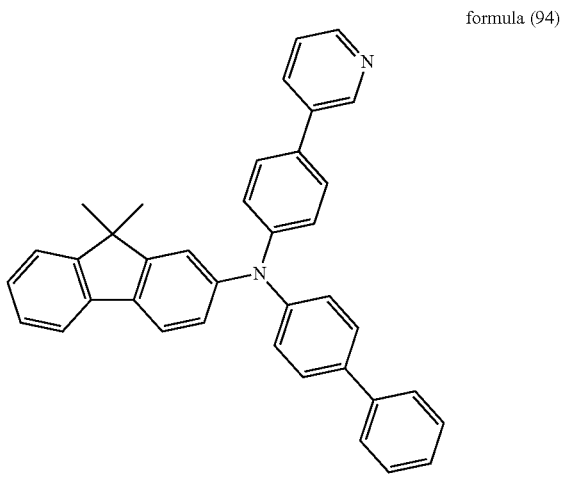
formula (94)

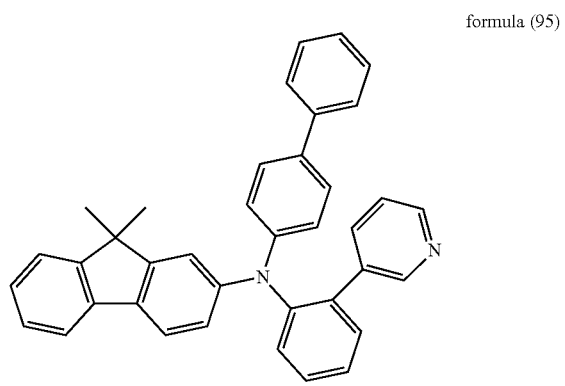
formula (95)

formula (96)

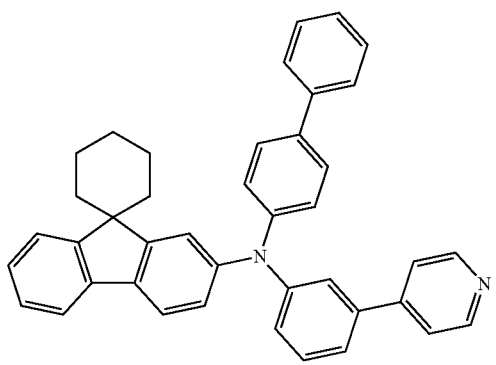

formula (138)

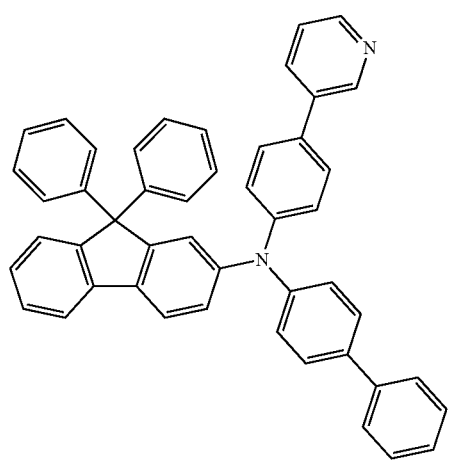

formula (139)

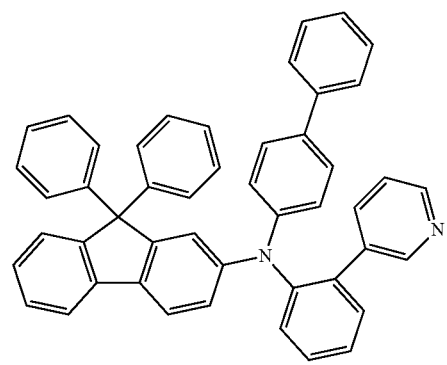

formula (140)

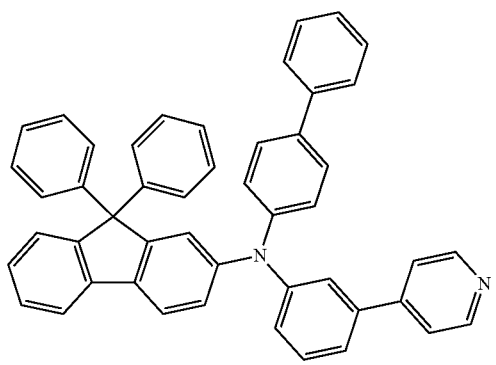

formula (201)

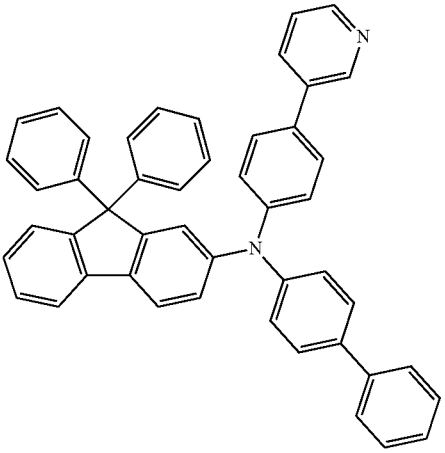

formula (202)

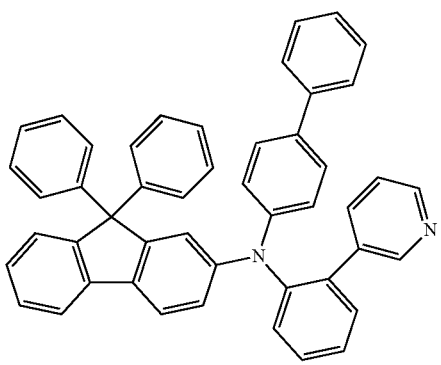

formula (203)

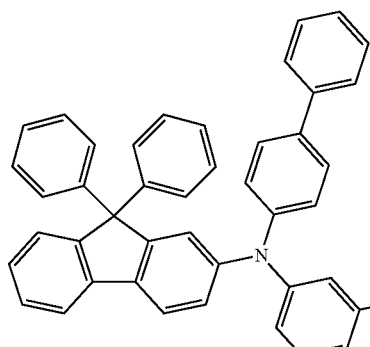

14. A process for the preparation of the compound according to claim 11 by means of one-step Buchwald coupling by reacting a fluorene derivative containing a leaving group with $Ar^3$—NH—$Ar^4$.

15. A process for the preparation of the compound according to claim 11 by means of two-step Buchwald coupling by stepwise reacting a phenanthrene derivative containing a leaving group with (1) $Ar^3$—$NH_2$ and (2) $NH_2$—$Ar^4$.

16. An oligomer, polymer or dendrimer containing one or more compounds of the general formula (167)

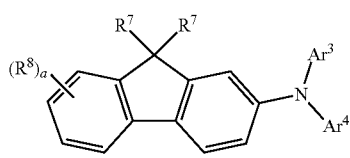

formula (167)

where the following applies to the symbols used in formula (167):

Ar³ and Ar⁴ are on each occurrence, identically or differently, an aromatic or heteroaromatic group having two or more aromatic or heteroaromatic rings and having 10 to 60 ring atoms in said aromatic or heteroaromatic group, which is optionally substituted by one or more radicals $R^5$, which are identical to or different from one another, wherein either Ar³ or Ar⁴ comprises at least one heteroaromatic group having 6 to 60 aromatic ring atoms, which is optionally substituted by one or more radicals $R^5$, which are identical to or different from one another;

$R^7$ is identical on each occurrence and is selected from the group consisting of a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^5$ and where one or more H atoms in the above-mentioned groups is optionally replaced by D, CN or $NO_2$, or an aromatic or heteroaromatic ring system having 6 to 30 ring atoms, which may in each case be substituted by one or more radicals $R^5$, where $R^5$ is defined as indicated above, or a condensed ring system having 9 to 30 ring atoms, which may in each case be substituted by one or more radicals $R^5$, where, in the case of aromatic or heteroaromatic condensed rings, not more than 10 ring atoms is optionally present in the condensed ring system; the two radicals $R^7$ may also form a ring closure with one another, so that a spiro compound forms, where no aromatic or heteroaromatic rings are condensed onto the ring formed by the two radicals $R^7$, and where, if $R^7$ is a straight-chain or branched alkyl group, $R^8$ is an aromatic or heteroaromatic ring system having 6 to 30 ring atoms, which may in each case be substituted by one or more radicals $R^5$, and where $R^5$ is defined as indicated above;

$R^8$ is H, D or an aromatic or heteroaromatic ring system having 6 to 30 ring atoms, which may in each case be substituted by one or more radicals $R^5$, where $R^5$ is defined as indicated above and where, if $R^8$ is equal to H, $R^7$ is an aromatic or heteroaromatic ring system having 6 to 30 aromatic ring atoms, which may in each case be substituted by one or more radicals $R^5$, where $R^5$ is defined as indicated above;

a is either 1, 2, 3 or 4;

with the proviso that the compound of the formula (167), besides the one fluorene group and besides the possible condensed or polycyclic groups in position 9 of the fluorene, contains no further polycyclic or condensed groups and with the proviso that the compound contains no halogens, where the bond(s) to the polymer, oligomer or dendrimer is optionally localised at any positions.

17. A composition comprising one or more compounds according to claim 11 and at least one further organically functional material selected from the group consisting of fluorescent emitters, phosphorescent emitters, host materials, matrix materials, electron-transport materials, electron-injection materials, hole-conductor materials, hole-injection materials, electron-blocking materials and hole-blocking materials.

18. A formulation comprising at least one compound according to claim 11 and at least one solvent.

19. An electronic device comprising at least one compound according to claim 11.

20. The electronic device according to claim 19, wherein the device is selected from the group consisting of organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and organic electroluminescent devices (OLEDs).

21. An organic electroluminescent device which comprises the compound according to claim 11 is employed in one or more of the following functions: as hole-transport material in a hole-transport or hole-injection layer, as matrix material in an emitting layer, as electron-blocking material or as exciton-blocking material.

22. The device according to claim 1, wherein at least one $Ar^1$ or $Ar^2$ is selected from the group consisting of radicals having the formulae (43)-(53) and (54):

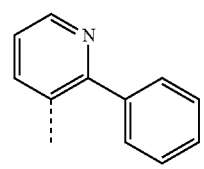

formula (43)

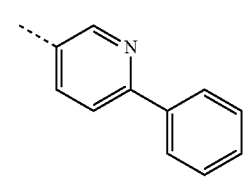

formula (44)

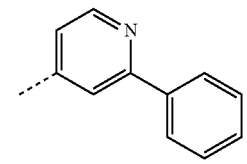

formula (45)

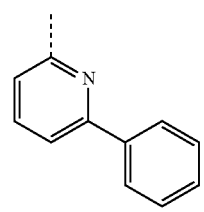

formula (46)

-continued
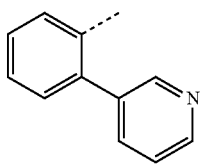 formula (47)
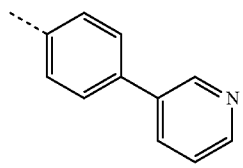 formula (48)
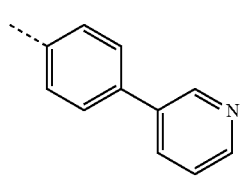 formula (49)
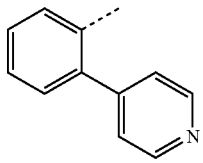 formula (50)
-continued
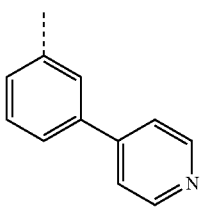 formula (51)
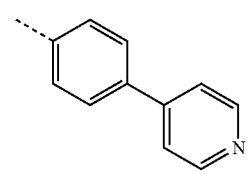 formula (52)
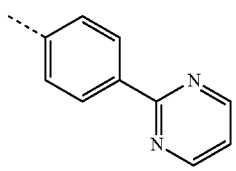 formula (53)
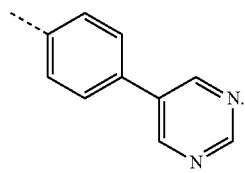 formula (54)
* * * * *